US012043669B2

(12) United States Patent
Ursø et al.

(10) Patent No.: US 12,043,669 B2
(45) Date of Patent: Jul. 23, 2024

(54) IL-1 RECEPTOR ACCESSORY PROTEIN-INHIBITING ANTIBODIES AND ANTIGEN-BINDING FRAGMENTS THEREOF

(71) Applicant: LEO Pharma A/S, Ballerup (DK)

(72) Inventors: Birgitte Ursø, Hellerup (DK); Waseem Sajid, Taastrup (DK); Paola Lovato, Copenhagen (DK); Heidi Westh Bagger, Copenhagen (DK); Christoph Erkel, Planegg (DE); Petra Nussbaumer, Planegg (DE); Simon Schuster, Neuenburg am Rhein (DE)

(73) Assignee: LEO Pharma A/S, Ballerup (DK)

( * ) Notice: Subject to any disclaimer, the term of this patent is extended or adjusted under 35 U.S.C. 154(b) by 0 days.

(21) Appl. No.: 18/507,579

(22) Filed: Nov. 13, 2023

(65) Prior Publication Data

US 2024/0190977 A1 Jun. 13, 2024

Related U.S. Application Data

(62) Division of application No. 17/664,349, filed on May 20, 2022.

(30) Foreign Application Priority Data

May 21, 2021 (EP) .................................. 21175216
Aug. 24, 2021 (EP) .................................. 21192805

(51) Int. Cl.
*C07K 16/28* (2006.01)
*A61K 39/00* (2006.01)

(52) U.S. Cl.
CPC .... *C07K 16/2866* (2013.01); *A61K 2039/505* (2013.01); *C07K 2317/21* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| CN | 110041428 | | 7/2019 |
|---|---|---|---|
| CN | 114835799 | A | 8/2022 |
| CN | 116143926 | | 5/2023 |
| CN | 116284401 | | 6/2023 |
| CN | 116574189 | A | 8/2023 |
| WO | WO 2003/048731 | A2 | 6/2003 |
| WO | WO 2014/100772 | A1 | 6/2014 |
| WO | WO 2015/132602 | A1 | 9/2015 |
| WO | WO 2015132602 | A1 | 9/2015 |
| WO | WO 2016/020502 | A1 | 2/2016 |
| WO | WO 2016020502 | A1 | 2/2016 |
| WO | WO 2016207304 | A1 | 12/2016 |
| WO | WO 2017/191325 | A1 | 11/2017 |
| WO | WO 2017191325 | A1 | 11/2017 |
| WO | WO 2018/071910 | A2 | 4/2018 |
| WO | WO 2018206565 | A1 | 11/2018 |
| WO | WO 2018/231827 | A1 | 12/2018 |
| WO | WO 2018/231827 | A9 | 12/2018 |
| WO | WO 2018231827 | A1 | 12/2018 |
| WO | WO 2019/028190 | A1 | 2/2019 |
| WO | WO 2019224717 | A1 | 11/2019 |
| WO | WO 2019230866 | A1 | 12/2019 |
| WO | WO 2020/037154 | A1 | 2/2020 |
| WO | WO 2020035577 | A1 | 2/2020 |
| WO | WO 2020037154 | A1 | 2/2020 |
| WO | WO 2020261097 | A1 | 12/2020 |
| WO | WO 2022053715 | A1 | 3/2022 |
| WO | WO 2022136569 | A1 | 6/2022 |
| WO | WO 2022170008 | A1 | 8/2022 |

OTHER PUBLICATIONS

Abraham et al., (1996) "Determination of Binding Constants of Diabodies Directed against Prostate-specific Antigen using Electrochemiluminescence-based Immunoassays," Journal of Molecular Recognition, vol. 9, 456-461.
Boraschi et al., (2018) "The family of the interleukin-1 receptors," Immunol. Rev. 281:197-232.
Buhl et al., (2019) "Interleukin-36 in Infectious and Inflammatory Skin Diseases," Front. Immunol. 2019, vol. 10 (11 pgs.).
Dinarello et al., (2012) "Treating inflammation by blocking interleukin-1 in a broad spectrum of diseases," Nat. Rev. Drug Discov. 11:633-652.
Ducata et al., (2015) "Solution Equilibrium Titration for High-Throughput Affinity Estimation of Unpurified Antibodies and Antibody Fragments," J. Biomol. Screen 20:1256-67.
Friguet et al., (1985) "Measurements of the true affinity constant in solution of antigen-antibody complexes by enzyme-linked immunosorbent assay," J. Immunol. Methods. 77:305-19.
Graham et al., (1977) "Characteristics of a human cell line transformed by DNA from human adenovirus type 5, "J. Gen. Virol. 36:59-74.
Haener et al., (2005) "Characterization of high-affinity antibodies by electrochemiluminescence-based equilibrium titration," Anal. Biochem. 339:182-4.
Jensen et al., (2010) "Targeting the IL-1 family members in skin inflammation," Curr. Opin. Inve. Drugs 11:1211-1220.
Khazim et al., (2018) "Interleukin 1 gene polymorphism and susceptibility to disease," Immunological Reviews, 281, 40-56.

(Continued)

*Primary Examiner* — Christine J Saoud

(74) *Attorney, Agent, or Firm* — FINNEGAN, HENDERSON, FARABOW, GARRETT & DUNNER, LLP

(57) ABSTRACT

The present disclosure provides novel antibodies and fragments thereof targeting IL-1RAcP (Interleukin-1 receptor accessory protein). Use of IL-1RAcP inhibitors are also provided herein.

9 Claims, 25 Drawing Sheets

Specification includes a Sequence Listing.

(56) References Cited

OTHER PUBLICATIONS

Maccallum et al., (1996) "Antibody-antigen Interactions: Contact Analysis and Binding Site Topography" J. Mol. Biol. 262, 732-745.
Machura et al., (2013), "Interleukin 1-B, Interleukin-1 Receptor Antagonist, and Interleukin 18 in Children with Acute Spontaneous Urticaria," BioMed Research International 2013:605262, (7 pgs.).
Mather, (1980) "Establishment and Characterization of Two Distinct Mouse Testicular Epithelial Cell Lines," Biol. Reprod. 23:243-251.
Morea et al., (2000) "Antibody Modeling: Implications for Engineering and Design," Methods 20, 267-279.
Palomo et al., (2015) "The interleukin (IL)-1 cytokine family—Balance between agonists and antagonists in inflammatory diseases," Cytokine 76:25-37.
Piehler et al., (1997) "Assessment of affinity conatants by rapid solid phase detection of equilibrium binding in a flow system," Journal of Immnological Methods 201, pp. 189-206.
Striz, (2017) "Cytokines of the IL-1 family: recognized targets in chronic inflammation underrated in organ transplantations," Clinical Science 131, 2241-2256.
Tatusova et al., "Blast 2 sequences—a new tool for comparing protein and nucleotide sequences", FEMS Microbiol Lett. 174:247-250.
Tavakolpour et al., (2020) "Pathogenic and protective roles of cytokines in pemphigus: A systematic review," Cytokine 129, 8 pgs.
Tiller et al., (2013) "A fully synthetic human Fab antibody library based on fixed VH/VL framework pairings with favorable biophysical properties," mAbs 5:3, 445-470.
Tramontano et al., (1990) "Framework residue 71 is a major determinant of the position and conformation of the second hypervariable region in the VH domains of immunoglobulins," J. Mol. Biol, 215:175-182.
Tsang et al., (2020) "The Role of New IL-1 Family Members (IL-36 and IL-38) in Atopic Dermatitis, Allergic Asthma, and Allergic Rhinitis," Cur. Alergy Asthma Rep. 20:40 (8 pgs.).
Urlaub et al., (1980) "Isolation of Chinese hamster cell mutants deficient in dihydrofolate reductase activity.", Proc. Natl. Acad. Sci. USA 77:4216-4220.
Van Den Brulle et al., (2008) "A novel solid phase technology for high-throughput gene synthesis" Biotechniques 45 (3), pp. 340-343.
Wang et al., (2006) "Antibody Structure, Instability, and Formulation," Journal of Pharmaceutical Sciences, vol. 96, pp. 1-26.
Wolk et al., (2020) "Aetiology and pathogenesis of hidradenitis suppurativa," Br. J. Deramtol. 183:999-1010.
Xu et al., (2019) "The Roles of IL-1 Family Cytokines in the Pathogenesis of Systemic Sclerosis," Front. Immunol. 10. (8 pgs.).
Boraschi et al., "The interleukin-1 receptor family", Seminars in Immunology 2013, vol. 25, pp. 394-407.
Mather et al., "Culture of Testicular Cells in Hormone-Supplemented Serum-Free Medium" 1982, Annals of the New York Academy of Sciences, vol. 383, Issue 1 p. 44-68.

INHIBITION OF IL-33 SIGNALING IN PERIPHERAL BLOOD MONONUCLEAR CELLS (PBMC) IN THE PRESENCE OF sIL-1RAcP

SEQUENCE LISTING

```
Sequence total quantity: 76
SEQ ID NO: 1            moltype = AA  length = 11
FEATURE                 Location/Qualifiers
REGION                  1..11
                        note = Y024128 LCDR1
source                  1..11
                        mol_type = protein
                        organism = synthetic construct
SEQUENCE: 1
RASQSISSWL A                                                            11

SEQ ID NO: 2            moltype = AA  length = 7
FEATURE                 Location/Qualifiers
REGION                  1..7
                        note = Y024148 LCDR2
source                  1..7
                        mol_type = protein
                        organism = synthetic construct
SEQUENCE: 2
DASSLES                                                                 7

SEQ ID NO: 3            moltype = AA  length = 9
FEATURE                 Location/Qualifiers
REGION                  1..9
                        note = Y024148 LCDR3
source                  1..9
                        mol_type = protein
                        organism = synthetic construct
SEQUENCE: 3
HQLLIYPHT                                                               9

SEQ ID NO: 4            moltype = AA  length = 5
FEATURE                 Location/Qualifiers
REGION                  1..5
                        note = Y024148 HCDR1
source                  1..5
                        mol_type = protein
                        organism = synthetic construct
SEQUENCE: 4
GSAVH                                                                   5

SEQ ID NO: 5            moltype = AA  length = 17
FEATURE                 Location/Qualifiers
REGION                  1..17
                        note = Y024148 HCDR2
source                  1..17
```

```
                              mol_type = protein
                              organism = synthetic construct
SEQUENCE: 5
RILTYSSTTQ YAESVKG                                                        17

SEQ ID NO: 6                  moltype = AA  length = 10
FEATURE                       Location/Qualifiers
REGION                        1..10
                              note = Y024148 HCDR3
source                        1..10
                              mol_type = protein
                              organism = synthetic construct
SEQUENCE: 6
GSSEYPKFDI                                                                10

SEQ ID NO: 7                  moltype = AA  length = 119
FEATURE                       Location/Qualifiers
REGION                        1..119
                              note = Y024148 VH
source                        1..119
                              mol_type = protein
                              organism = synthetic construct
SEQUENCE: 7
EVQLVESGGG LVQPGGSLRL SCAASGGTIG GSAVHWVRQA PGKGLVWVSR ILTYSSTTQY          60
AESVKGRFTI SRDNAKNTLY LQMNSLRAED TAVYYCARGS SEYPKFDIWG QGTLVTVSS          119

SEQ ID NO: 8                  moltype = AA  length = 109
FEATURE                       Location/Qualifiers
REGION                        1..109
                              note = Y024148 VL
source                        1..109
                              mol_type = protein
                              organism = synthetic construct
SEQUENCE: 8
DIQMTQSPST LSASVGDRVT ITCRASQSIS SWLAWYQQKP GKAPKLLIYD ASSLESGVPS          60
RFSGSGSGTE FTLTISSLQP EDFATYYCHQ LLIYPHTFGQ GTKVEIKRT                    109

SEQ ID NO: 9                  moltype = AA  length = 11
FEATURE                       Location/Qualifiers
REGION                        1..11
                              note = Y024149 LCDR1
source                        1..11
                              mol_type = protein
                              organism = synthetic construct
SEQUENCE: 9
RASQSISSWL A                                                              11

SEQ ID NO: 10                 moltype = AA  length = 7
FEATURE                       Location/Qualifiers
REGION                        1..7
                              note = Y024149 LCDR2
source                        1..7
                              mol_type = protein
                              organism = synthetic construct
SEQUENCE: 10
DASSLES                                                                    7

SEQ ID NO: 11                 moltype = AA  length = 9
FEATURE                       Location/Qualifiers
REGION                        1..9
                              note = Y024149 LCDR3
source                        1..9
                              mol_type = protein
                              organism = synthetic construct
SEQUENCE: 11
HQLLIYPHT                                                                  9

SEQ ID NO: 12                 moltype = AA  length = 5
FEATURE                       Location/Qualifiers
REGION                        1..5
                              note = Y024149 HCDR1
source                        1..5
                              mol_type = protein
                              organism = synthetic construct
SEQUENCE: 12
GSAMH                                                                      5

SEQ ID NO: 13                 moltype = AA  length = 17
FEATURE                       Location/Qualifiers
```

```
REGION                  1..17
                        note = Y024149 HCDR2
source                  1..17
                        mol_type = protein
                        organism = synthetic construct
SEQUENCE: 13
RILTYGGIAT YAESVKG                                                  17

SEQ ID NO: 14           moltype = AA  length = 10
FEATURE                 Location/Qualifiers
REGION                  1..10
                        note = Y024149 HCDR3
source                  1..10
                        mol_type = protein
                        organism = synthetic construct
SEQUENCE: 14
GSSEYPKFDI                                                          10

SEQ ID NO: 15           moltype = AA  length = 119
FEATURE                 Location/Qualifiers
REGION                  1..119
                        note = Y024149 VH
source                  1..119
                        mol_type = protein
                        organism = synthetic construct
SEQUENCE: 15
EVQLVESGGG LVQPGGSLRL SCAASGGTFG GSAMHWVRQA PGKGLVWVSR ILTYGGIATY   60
AESVKGRFTI SRDNAKNTLY LQMNSLRAED TAVYYCARGS SEYPKFDIWG QGTLVTVSS    119

SEQ ID NO: 16           moltype = AA  length = 109
FEATURE                 Location/Qualifiers
REGION                  1..109
                        note = Y024149 VL
source                  1..109
                        mol_type = protein
                        organism = synthetic construct
SEQUENCE: 16
DIQMTQSPST LSASVGDRVT ITCRASQSIS SWLAWYQQKP GKAPKLLIYD ASSLESGVPS   60
RFSGSGSGTE FTLTISSLQP EDFATYYCHQ LLIYPHTFGQ GTKVEIKRT              109

SEQ ID NO: 17           moltype = AA  length = 449
FEATURE                 Location/Qualifiers
REGION                  1..449
                        note = Y024148 HC
source                  1..449
                        mol_type = protein
                        organism = synthetic construct
SEQUENCE: 17
EVQLVESGGG LVQPGGSLRL SCAASGGTIG GSAVHWVRQA PGKGLVWVSR ILTYSSTTQY   60
AESVKGRFTI SRDNAKNTLY LQMNSLRAED TAVYYCARGS SEYPKFDIWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAEGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PSSIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 18           moltype = AA  length = 214
FEATURE                 Location/Qualifiers
REGION                  1..214
                        note = Y024148 LC
source                  1..214
                        mol_type = protein
                        organism = synthetic construct
SEQUENCE: 18
DIQMTQSPST LSASVGDRVT ITCRASQSIS SWLAWYQQKP GKAPKLLIYD ASSLESGVPS   60
RFSGSGSGTE FTLTISSLQP EDFATYYCHQ LLIYPHTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 19           moltype = AA  length = 449
FEATURE                 Location/Qualifiers
REGION                  1..449
                        note = Y024149 HC
source                  1..449
                        mol_type = protein
                        organism = synthetic construct
SEQUENCE: 19
EVQLVESGGG LVQPGGSLRL SCAASGGTFG GSAMHWVRQA PGKGLVWVSR ILTYGGIATY   60
```

```
AESVKGRFTI SRDNAKNTLY LQMNSLRAED TAVYYCARGS SEYPKFDIWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDKTHTCPP CPAPEAEGAP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PSSIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                     449

SEQ ID NO: 20           moltype = AA   length = 214
FEATURE                 Location/Qualifiers
REGION                  1..214
                        note = Y024149 LC
source                  1..214
                        mol_type = protein
                        organism = synthetic construct
SEQUENCE: 20
DIQMTQSPST LSASVGDRVT ITCRASQSIS SWLAWYQQKP GKAPKLLIYD ASSLESGVPS     60
RFSGSGSGTE FTLTISSLQP EDFATYYCHQ LLIYPHTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 21           moltype = DNA   length = 357
FEATURE                 Location/Qualifiers
misc_feature            1..357
                        note = Y024148 VH
source                  1..357
                        mol_type = other DNA
                        organism = synthetic construct
SEQUENCE: 21
gaagtgcagc tggtggaaag cggcggtggc ctggtgcagc caggtggtag cctgcgcctg     60
agctgcgccg ccagcggcgg caccatcggg ggcagcgccg tgcattgggt tcgccaggcc    120
ccaggcaaag gcctggtttg ggttagtcgc atacttactt actctagcac aactcaatat    180
gccgagagcg tgaaaggccg ctttaccatt agccgcgata cgccaaaaa cacccctgtat   240
ctgcaaatga cagcctgcg ggccgaagat accgccgtgt attattgcgc gcgtggttcc    300
agcgagtacc ctaaatttga tatttggggc cagggcaccc tggttactgt ctcgagc      357

SEQ ID NO: 22           moltype = DNA   length = 320
FEATURE                 Location/Qualifiers
misc_feature            1..320
                        note = Y024148 VL
source                  1..320
                        mol_type = other DNA
                        organism = synthetic construct
SEQUENCE: 22
gatattcaga tgacccagag cccgagcacc ctgagcgcaa gcgtgggcga tcgcgtgacc     60
attacctgcc gcgccagtca gagcattagc agctggctgg cctggtatca gcagaaaccg    120
ggcaaagccc cgaaactgct gatctatgat gccagcagtc tggaaagcgg cgtgccgagc    180
cgctttagcg gcagcggtag cggcaccgag ttcaccctga ccattagcag cctgcaaccg    240
gaagactttg ccacctatta ttgccaccag ctgctgatct acccgcatac cttcggccag    300
ggtaccaaag tggaaatcaa                                                320

SEQ ID NO: 23           moltype = DNA   length = 1347
FEATURE                 Location/Qualifiers
misc_feature            1..1347
                        note = Y024148 HC
source                  1..1347
                        mol_type = other DNA
                        organism = synthetic construct
SEQUENCE: 23
gaagtgcagc tggtggaaag cggcggtggc ctggtgcagc caggtggtag cctgcgcctg     60
agctgcgccg ccagcggcgg caccatcggg ggcagcgccg tgcattgggt tcgccaggcc    120
ccaggcaaag gcctggtttg ggttagtcgc atacttactt actctagcac aactcaatat    180
gccgagagcg tgaaaggccg ctttaccatt agccgcgata cgccaaaaa cacccctgtat   240
ctgcaaatga cagcctgcg ggccgaagat accgccgtgt attattgcgc gcgtggttcc    300
agcgagtacc ctaaatttga tatttggggc cagggcaccc tggttactgt ctcgagcgcg    360
tcgaccaaag gcccagcgt gttccctctg gccccagca gcaagagcac ctctggcgga    420
acagccgccc tgggctgcct ggtcaaggac tacttcccg agcccgtgac cgtgtcctgg    480
aactctggcg ccctgaccag cggcgtgcac accttccag ccgtgctcca gagcagcggc    540
ctgtacagcc tgagcagcgt cgtgaccgtg cccagcagca gcctgggcac ccagacctac    600
atctgcaacg tgaaccacaa gcccagcaac acaaaggtgg acaagcgggt ggaacccaag    660
agctgcgaca gacccacac ctgtcccccc tgccctgccc ctgaagcgga gggagccccc    720
tccgtgttcc tgttcccccc aaagcctaag gacaccctga tcagccgg accccgaa      780
gtgacctgcg tggtggtgga cgtgtcccac gaggaccctg aagtgaagtt taattggtac    840
gtggacggcg tggaagtgca caacgccaag accaagcca gagaggaaca gtacaacagc    900
acctaccggg tggtgtccgt gctgaccgtg ctgcaccagg actggctgaa cggcaaagag    960
tacaagtgca aggtctccaa caaggccctg ccttcctcca tcgagaaaac catcagcaag   1020
gccaaaggcc agccccgcga gccccaggtg tacacactgc ccctagccg ggaagagatg   1080
accaagaacc aggtgtccct gacctgcctc gtgaagggct tctacccag cgacattgcc   1140
gtggaatggg agagcaacgg ccagcccgag aacaactaca agaccacccc cctgtgctg   1200
```

|  |  |  |
|---|---|---|
| gacagcgacg | gctcattctt cctgtacagc aagctgaccg tggacaagag ccggtggcag | 1260 |
| cagggcaacg | tgttcagctg ctccgtgatg cacgaggccc tgcacaacca ctacacccag | 1320 |
| aagtccctga | gcctgagccc cggcaag | 1347 |

```
SEQ ID NO: 24            moltype = DNA   length = 642
FEATURE                  Location/Qualifiers
misc_feature             1..642
                         note = Y024148 LC
source                   1..642
                         mol_type = other DNA
                         organism = synthetic construct
SEQUENCE: 24
```

|  |  |  |
|---|---|---|
| gatattcaga | tgacccagag cccgagcacc ctgagcgcaa gcgtgggcga tcgcgtgacc | 60 |
| attacctgcc | gcgccagtca gagcattagc agctggctgg cctggtatca gcagaaaccg | 120 |
| ggcaaagccc | cgaaactgct gatctatgat gccagcagcc tggaaagcgg cgtgccgagc | 180 |
| cgctttagcg | gcagcggtag cggcaccgag ttcaccctga ccattagcag cctgcaaccg | 240 |
| gaagactttg | ccacctatta ttgccaccag ctgctgatct acccgcatac cttcggccag | 300 |
| ggtaccaaag | tggaaatcaa gcggaccgtg gccgctccct ccgtgttcat cttcccaccc | 360 |
| agcgacgagc | agctgaagtc cggcacagcc agcgtcgtgt gcctgctgaa caacttctac | 420 |
| ccccgcgagg | ccaaagtgca gtggaaggtg gacaacgccc tccagagcgg caacagccag | 480 |
| gaaagcgtca | ccgagcagga cagcaaggac tccacctaca gcctgagcag caccctgacc | 540 |
| ctgagcaagg | ccgactacga aagcacaaag gtgtacgcct gcgaagtgac ccaccagggc | 600 |
| ctgtccagcc | ccgtgaccaa gagcttcaac cggggcgagt gt | 642 |

```
SEQ ID NO: 25            moltype = DNA   length = 357
FEATURE                  Location/Qualifiers
misc_feature             1..357
                         note = Y024149 VH
source                   1..357
                         mol_type = other DNA
                         organism = synthetic construct
SEQUENCE: 25
```

|  |  |  |
|---|---|---|
| gaagtgcagc | tggtggaaag cggcggtggc ctggtgcagc caggtggtag cctgcgcctg | 60 |
| agctgcgccg | ccagcggggg gacattcggg ggcagcgcca tgcactgggt cgccaggcc | 120 |
| ccaggcaaag | gcctggtttg ggttagtcgc atacttacat acggaggtat cgcaacctat | 180 |
| gcggagagcg | tgaaaggccg ctttaccatt agccgcgata cgccaaaaa caccctgtat | 240 |
| ctgcaaatga | acagcctgcg ggccgaagat accgccgtgt attattgcgc gcgtggttcc | 300 |
| agcgagtacc | ctaaatttga tatttggggc cagggcaccc tggttactgt ctcgagc | 357 |

```
SEQ ID NO: 26            moltype = DNA   length = 327
FEATURE                  Location/Qualifiers
misc_feature             1..327
                         note = Y024149 VL
source                   1..327
                         mol_type = other DNA
                         organism = synthetic construct
SEQUENCE: 26
```

|  |  |  |
|---|---|---|
| gatattcaga | tgacccagag cccgagcacc ctgagcgcaa gcgtgggcga tcgcgtgacc | 60 |
| attacctgcc | gcgccagtca gagcattagc agctggctgg cctggtatca gcagaaaccg | 120 |
| ggcaaagccc | cgaaactgct gatctatgat gccagcagcc tggaaagcgg cgtgccgagc | 180 |
| cgctttagcg | gcagcggtag cggcaccgag ttcaccctga ccattagcag cctgcaaccg | 240 |
| gaagactttg | ccacctatta ttgccaccag ctgctgatct acccgcatac cttcggccag | 300 |
| ggtaccaaag | tggaaatcaa gcggacc | 327 |

```
SEQ ID NO: 27            moltype = DNA   length = 1347
FEATURE                  Location/Qualifiers
misc_feature             1..1347
                         note = Y024149 HC
source                   1..1347
                         mol_type = other DNA
                         organism = synthetic construct
SEQUENCE: 27
```

|  |  |  |
|---|---|---|
| gaagtgcagc | tggtggaaag cggcggtggc ctggtgcagc caggtggtag cctgcgcctg | 60 |
| agctgcgccg | ccagcggggg gacattcggg ggcagcgcca tgcactgggt cgccaggcc | 120 |
| ccaggcaaag | gcctggtttg ggttagtcgc atacttacat acggaggtat cgcaacctat | 180 |
| gcggagagcg | tgaaaggccg ctttaccatt agccgcgata cgccaaaaa caccctgtat | 240 |
| ctgcaaatga | acagcctgcg ggccgaagat accgccgtgt attattgcgc gcgtggttcc | 300 |
| agcgagtacc | ctaaatttga tatttggggc cagggcaccc tggttactgt ctcgagcgcg | 360 |
| tcgaccaaag | gcccctctg gcccccagca ccaagagcac ctctggcgga | 420 |
| acagccgccc | tgggctgcct ggtcaaggac tacttcccg agcccgtgac cgtgtcctgg | 480 |
| aactctggcg | ccctgaccag cggcgtgcac acctttccag ccgtgctcca gagcagcggc | 540 |
| ctgtacagcc | tgagcagcgt cgtgaccgtg cccagcagca gcctgggcac ccagacctac | 600 |
| atctgcaacg | tgaaccacaa gcccagcaac acaaaggtgg acaagcgggt ggaacccaag | 660 |
| agctgcgaca | agacccacac ctgtccccc tgccctgccc ctgaagcgga gggagcccaa | 720 |
| tccgtgttcc | tgttcccccc aaagcctaag gacaccctga tgatcagccg gacccccgaa | 780 |
| gtgacctgcg | tggtggtgga cgtgtcccac gaggaccctg aagtgaagtt taattggtac | 840 |
| gtggacggcg | tggaagtgca caacgccaag accaagccca gagaggaaca gtacaacagc | 900 |
| acctaccggg | tggtgtccgt gctgaccgtg ctgcaccagg actggctgaa cggcaaagag | 960 |
| tacaagtgca | aggtgtccaa caaggccctg ccttcctcca tcgagaaaac catcagcaag | 1020 |

```
gccaaaggcc agccccgcga gccccaggtg tacacactgc ccctagccg gaagagatg    1080
accaagaacc aggtgtccct gacctgcctc gtgaagggct tctacccag cgacattgcc    1140
gtggaatggg agagcaacgg ccagcccgag aacaactaca agaccacccc ccctgtgctg    1200
gacagcgacg gctcattctt cctgtacagc aagctgaccg tggacaagag ccggtggcag    1260
cagggcaacg tgttcagctg ctccgtgatg cacgaggccc tgcacaacca ctacacccag    1320
aagtccctga gcctgagccc cggcaag                                        1347
```

| SEQ ID NO: 28 | moltype = DNA length = 642 |
|---|---|
| FEATURE | Location/Qualifiers |
| misc_feature | 1..642 |
| | note = Y024149 LC |
| source | 1..642 |
| | mol_type = other DNA |
| | organism = synthetic construct |

```
SEQUENCE: 28
gatattcaga tgacccagag cccgagcacc ctgagcgcaa gcgtgggcga tcgcgtgacc    60
attacctgcc gcgccagtca gagcattagc agctggctgg cctggtatca gcagaaaccg    120
ggcaaagccc cgaaactgct gatctatgat gccagcagcc tggaaagcgg cgtgccgagc    180
cgctttagcg gcagcggtag cggcaccgag ttcaccctga ccattagcag cctgcaaccg    240
gaagactttg ccacctatta ttgccaccag ctgctgatct acccgcatac cttcggccag    300
ggtaccaaag tggaaatcaa gcggaccgtg gccgctccct ccgtgttcat cttcccaccc    360
agcgacgagc agctgaagtc cggcacagcc agcgtcgtgt gcctgctgaa caacttctac    420
ccccgcgagg ccaaagtgca gtggaaggtg gacaacgccc tccagagcgg caacagccag    480
gaaagcgtca ccgagcagga cagcaaggac tccacctaca gcctgagcag caccctgacc    540
ctgagcaagg ccgactacga gaagcacaag gtgtacgcct gcgaagtgac ccaccagggc    600
ctgtccagcc ccgtgaccaa gagcttcaac cggggcgagt gt                       642
```

| SEQ ID NO: 29 | moltype = AA length = 448 |
|---|---|
| FEATURE | Location/Qualifiers |
| REGION | 1..448 |
| | note = Y024084 VH |
| source | 1..448 |
| | mol_type = protein |
| | organism = synthetic construct |

```
SEQUENCE: 29
QVQLVQSGAE VKKPGASVKV SCKASGYTFT SYYMHWVRQA PGQGLEWMGI INPSGGSTSY    60
AQKFQGRVTM TRDTSTSTVY MELSSLRSED TAVYYCARGF VTSGIDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKRVEPKS CDKTHTCPPC PAPEAEGAPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP SSIEKTISKA KGQPREPQVY TLPPSREEMT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGK                                        448
```

| SEQ ID NO: 30 | moltype = AA length = 217 |
|---|---|
| FEATURE | Location/Qualifiers |
| REGION | 1..217 |
| | note = Y024084 VL |
| source | 1..217 |
| | mol_type = protein |
| | organism = synthetic construct |

```
SEQUENCE: 30
QSVLTQPPSV SAAPGQKVTI SCSGSSSNIG NNYVSWYQQL PGTAPKLLIY DNNKRPSGIP    60
DRFSGSKSGT SATLGITGLQ TEDEADYYCQ TWTYTGRLWI FGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                              217
```

| SEQ ID NO: 31 | moltype = AA length = 448 |
|---|---|
| FEATURE | Location/Qualifiers |
| REGION | 1..448 |
| | note = h11C5 YKD HC |
| source | 1..448 |
| | mol_type = protein |
| | organism = synthetic construct |

```
SEQUENCE: 31
EVQLVESGGG LVQPGGSLRL SCAASGFTFS NYAMSWVRQA PGKGLEWVAT VTEGGDYNYY    60
LDDVKGRFTI SRDNAKNSLY LQMNSLRAED TAVYYCARDD WPYFFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKRVEPKS CDKTHTCPPC PAPEAEGAPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP SSIEKTISKA KGQPREPQVY TLPPSREEMT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGK                                        448
```

| SEQ ID NO: 32 | moltype = AA length = 213 |
|---|---|
| FEATURE | Location/Qualifiers |
| REGION | 1..213 |
| | note = h11C5 YKD LC |
| source | 1..213 |

```
                            mol_type = protein
                            organism = synthetic construct
SEQUENCE: 32
DIQMTQSPSS LSASVGDRVT ITCRASENIY SNLAWYQQKP GKSPKLLVYG YKNLADVPSR        60
FSGSGSGTDY TLTISSLQPE DFATYYCQHF KTTPRTFGGG TKVEIKRTVA APSVFIFPPS       120
DEQLKSGTAS VVCLLNNFYP REAKVQWKVD NALQSGNSQE SVTEQDSKDS TYSLSSTLTL       180
SKADYEKHKV YACEVTHQGL SSPVTKSFNR GEC                                    213

SEQ ID NO: 33               moltype = AA  length = 118
FEATURE                     Location/Qualifiers
REGION                      1..118
                            note = h11C5 YKD VH
source                      1..118
                            mol_type = protein
                            organism = synthetic construct
SEQUENCE: 33
EVQLVESGGG LVQPGGSLRL SCAASGFTFS NYAMSWVRQA PGKGLEWVAT VTEGGDYNYY        60
LDDVKGRFTI SRDNAKNSLY LQMNSLRAED TAVYYCARDD WPYFFDYWGQ GTLVTVSS         118

SEQ ID NO: 34               moltype = AA  length = 108
FEATURE                     Location/Qualifiers
REGION                      1..108
                            note = h11C5 YKD VL
source                      1..108
                            mol_type = protein
                            organism = synthetic construct
SEQUENCE: 34
DIQMTQSPSS LSASVGDRVT ITCRASENIY SNLAWYQQKP GKSPKLLVYG YKNLADVPSR        60
FSGSGSGTDY TLTISSLQPE DFATYYCQHF KTTPRTFGGG TKVEIKRT                    108

SEQ ID NO: 35               moltype = AA  length = 453
FEATURE                     Location/Qualifiers
REGION                      1..453
                            note = 1A05 HC
source                      1..453
                            mol_type = protein
                            organism = synthetic construct
SEQUENCE: 35
QQLEQSGGGA EGGLVKPGGS LELCCKASGF SLSTSYWRCW VRQAPGKGLE WIGCIYAGSG        60
DVTYYANWVN GRFTLSRDID QSTGCLQLNS LTAADTAMYY CASGVGFGYF NLWGQGTLVT       120
VSSASTKGPS VFPLAPSSKS TSGGTAALGC LVKDYFPEPV TVSWNSGALT SGVHTFPAVL       180
QSSGLYSLSS VVTVPSSSLG TQTYICNVNH KPSNTKVDKR VEPKSCDKTH TCPPCPAPEA       240
EGAPSVFLFP PKPKDTLMIS RTPEVTCVVV DVSHEDPEVK FNWYVDGVEV HNAKTKPREE       300
QYNSTYRVVS VLTVLHQDWL NGKEYKCKVS NKALPSSIEK TISKAKGQPR EPQVYTLPPS       360
REEMTKNQVS LTCLVKGFYP SDIAVEWESN GQPENNYKTT PPVLDSDGSF FLYSKLTVDK       420
SRWQQGNVFS CSVMHEALHN HYTQKSLSLS PGK                                    453

SEQ ID NO: 36               moltype = AA  length = 217
FEATURE                     Location/Qualifiers
REGION                      1..217
                            note = 1A05 LC
source                      1..217
                            mol_type = protein
                            organism = synthetic construct
SEQUENCE: 36
ALVMTQTPSP VSAAVGGTVT INCQASEDIY SNLAWFQQKP GQPPKLLIYD ASTLASGVPS        60
RFSGSGSGTE FTLTISGLQS DDAATYYCLG VYTHISADNA FGGGTEVVVK RTVAAPSVFI       120
FPPSDEQLKS GTASVVCLLN NFYPREAKVQ WKVDNALQSG NSQESVTEQD SKDSTYSLSS       180
TLTLSKADYE KHKVYACEVT HQGLSSPVTK SFNRGEC                                217

SEQ ID NO: 37               moltype = AA  length = 123
FEATURE                     Location/Qualifiers
REGION                      1..123
                            note = 1A05 VH
source                      1..123
                            mol_type = protein
                            organism = synthetic construct
SEQUENCE: 37
QQLEQSGGGA EGGLVKPGGS LELCCKASGF SLSTSYWRCW VRQAPGKGLE WIGCIYAGSG        60
DVTYYANWVN GRFTLSRDID QSTGCLQLNS LTAADTAMYY CASGVGFGYF NLWGQGTLVT       120
VSS                                                                    123

SEQ ID NO: 38               moltype = AA  length = 112
FEATURE                     Location/Qualifiers
REGION                      1..112
                            note = 1A05 VL
source                      1..112
                            mol_type = protein
                            organism = synthetic construct
```

```
SEQUENCE: 38
ALVMTQTPSP VSAAVGGTVT INCQASEDIY SNLAWFQQKP GQPPKLLIYD ASTLASGVPS    60
RFSGSGSGTE FTLTISGLQS DDAATYYCLG VYTHISADNA FGGGTEVVVK RT           112

SEQ ID NO: 39           moltype = AA  length = 446
FEATURE                 Location/Qualifiers
REGION                  1..446
                        note = 4G9 HC
source                  1..446
                        mol_type = protein
                        organism = synthetic construct
SEQUENCE: 39
QVQLQQSGTE LVRPGASVKL SCKASGYTFT DYEMHWVKQT PVHGLEWIGA IDPGTGGIAY    60
NQKFKGKATL TADKSSSTAY MELRSLTSED SAVYYCTLYD YDLAYWGQGT LVTVSAASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKRVEPKSCD KTHTCPPCPA PEAEGAPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPSS IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 40           moltype = AA  length = 219
FEATURE                 Location/Qualifiers
REGION                  1..219
                        note = 4G9 LC
source                  1..219
                        mol_type = protein
                        organism = synthetic construct
SEQUENCE: 40
DVLMTQTPLS LPVSLGDQAS ISCRSSQSIV HSNGNTYLEW FLQKPGQSPK LLIYTVSNRF    60
SGVPDRFSGS GSGTDFTLKI SRVEAEDLGV YYCFQGSHVP PTFGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 41           moltype = AA  length = 116
FEATURE                 Location/Qualifiers
REGION                  1..116
                        note = 4G9 VH
source                  1..116
                        mol_type = protein
                        organism = synthetic construct
SEQUENCE: 41
QVQLQQSGTE LVRPGASVKL SCKASGYTFT DYEMHWVKQT PVHGLEWIGA IDPGTGGIAY    60
NQKFKGKATL TADKSSSTAY MELRSLTSED SAVYYCTLYD YDLAYWGQGT LVTVSA       116

SEQ ID NO: 42           moltype = AA  length = 114
FEATURE                 Location/Qualifiers
REGION                  1..114
                        note = 4G9 VL
source                  1..114
                        mol_type = protein
                        organism = synthetic construct
SEQUENCE: 42
DVLMTQTPLS LPVSLGDQAS ISCRSSQSIV HSNGNTYLEW FLQKPGQSPK LLIYTVSNRF    60
SGVPDRFSGS GSGTDFTLKI SRVEAEDLGV YYCFQGSHVP PTFGGGTKLE IKRT         114

SEQ ID NO: 43           moltype = AA  length = 450
FEATURE                 Location/Qualifiers
REGION                  1..450
                        note = Can01 HC
source                  1..450
                        mol_type = protein
                        organism = synthetic construct
SEQUENCE: 43
QVQLQQSGTE LMKPGASVKI SCKATGYTVS SYWIDWVKQT PGHGLEWIGE ILPGSAINNY    60
NEKFKGKATF TADTSSNTAY MQLSSLTSED SAVYYCASGD YFDSTFVYYW GQGTTLTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAEGA   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPSSIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 44           moltype = AA  length = 219
FEATURE                 Location/Qualifiers
REGION                  1..219
                        note = Can01 LC
source                  1..219
                        mol_type = protein
```

```
                        organism = synthetic construct
SEQUENCE: 44
DVLMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YYCFQGSHVP RTFGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 45           moltype = AA  length = 120
FEATURE                 Location/Qualifiers
REGION                  1..120
                        note = Can01 VH
source                  1..120
                        mol_type = protein
                        organism = synthetic construct
SEQUENCE: 45
QVQLQQSGTE LMKPGASVKI SCKATGYTVS SYWIDWVKQT PGHGLEWIGE ILPGSAINNY    60
NEKFKGKATF TADTSSNTAY MQLSSLTSED SAVYYCASGD YFDSTFVYYW GQGTTLTVSS   120

SEQ ID NO: 46           moltype = AA  length = 114
FEATURE                 Location/Qualifiers
REGION                  1..114
                        note = Can01 VL
source                  1..114
                        mol_type = protein
                        organism = synthetic construct
SEQUENCE: 46
DVLMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YYCFQGSHVP RTFGGGTKLE IKRT         114

SEQ ID NO: 47           moltype = AA  length = 449
FEATURE                 Location/Qualifiers
REGION                  1..449
                        note = Can03 HC
source                  1..449
                        mol_type = protein
                        organism = synthetic construct
SEQUENCE: 47
DVKLVESGGG LVKPGGSLKL SCAASGFTFS IYTMSWVRQT PEKRLEWVAT ISIGGSYINY    60
PDSVKGRFTI SRDNAKNTLY LQMSSLKSED TAIYYCSREV DGSYAMDYWG QGTSVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEAEGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PSSIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 48           moltype = AA  length = 214
FEATURE                 Location/Qualifiers
REGION                  1..214
                        note = Can03 LC
source                  1..214
                        mol_type = protein
                        organism = synthetic construct
SEQUENCE: 48
DILLTQSPAI LSVSPGERVS FSCRASQSIG TSIHWYQRRT NGSPRLLIKS ASESISGIPS    60
RFSGSGSGTD FTLSINSVES EDIADYYCQQ SNSWPTTFGA GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 49           moltype = AA  length = 119
FEATURE                 Location/Qualifiers
REGION                  1..119
                        note = Can03 VH
source                  1..119
                        mol_type = protein
                        organism = synthetic construct
SEQUENCE: 49
DVKLVESGGG LVKPGGSLKL SCAASGFTFS IYTMSWVRQT PEKRLEWVAT ISIGGSYINY    60
PDSVKGRFTI SRDNAKNTLY LQMSSLKSED TAIYYCSREV DGSYAMDYWG QGTSVTVSS   119

SEQ ID NO: 50           moltype = AA  length = 109
FEATURE                 Location/Qualifiers
REGION                  1..109
                        note = Can03 VL
source                  1..109
                        mol_type = protein
                        organism = synthetic construct
SEQUENCE: 50
DILLTQSPAI LSVSPGERVS FSCRASQSIG TSIHWYQRRT NGSPRLLIKS ASESISGIPS    60
```

```
RFSGSGSGTD FTLSINSVES EDIADYYCQQ SNSWPTTFGA GTKLELKRT            109

SEQ ID NO: 51          moltype = AA   length = 447
FEATURE                Location/Qualifiers
REGION                 1..447
                       note = Can04 HC
source                 1..447
                       mol_type = protein
                       organism = synthetic construct
SEQUENCE: 51
QVQLVQSGAE VKKPGSSVKV SCKASGYAFS SSWMNWVRQA PGQGLEWMGR IYPGDGNTHY  60
AQKFQGRVTL TADKSTSTAY MELSSLRSED TAVYYCGEGY LDPMDYWGQG TLVTVSSAST 120
KGPSVFPLAP SSKSTSGGTA ALGCLVKDYF PEPVTVSWNS GALTSGVHTF PAVLQSSGLY 180
SLSSVVTVPS SSLGTQTYIC NVNHKPSNTK VDKRVEPKSC DKTHTCPPCP APEAEGAPSV 240
FLFPPKPKDT LMISRTPEVT CVVVDVSHED PEVKFNWYVD GVEVHNAKTK PREEQYNSTY 300
RVVSVLTVLH QDWLNGKEYK CKVSNKALPS SIEKTISKAK GQPREPQVYT LPPSREEMTK 360
NQVSLTCLVK GFYPSDIAVE WESNGQPENN YKTTPPVLDS DGSFFLYSKL TVDKSRWQQG 420
NVFSCSVMHE ALHNHYTQKS LSLSPGK                                   447

SEQ ID NO: 52          moltype = AA   length = 214
FEATURE                Location/Qualifiers
REGION                 1..214
                       note = Can04 LC
source                 1..214
                       mol_type = protein
                       organism = synthetic construct
SEQUENCE: 52
DIQMTQSPSS LSASVGDRVT ITCSASQGIN NYLNWYQQKP GKAPKLLIHY TSGLHAGVPS  60
RFSGSGSGTD YTLTISSLQP EDVATYYCQQ YSILPWTFGG GTKVEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                           214

SEQ ID NO: 53          moltype = AA   length = 117
FEATURE                Location/Qualifiers
REGION                 1..117
                       note = Can04 VH
source                 1..117
                       mol_type = protein
                       organism = synthetic construct
SEQUENCE: 53
QVQLVQSGAE VKKPGSSVKV SCKASGYAFS SSWMNWVRQA PGQGLEWMGR IYPGDGNTHY  60
AQKFQGRVTL TADKSTSTAY MELSSLRSED TAVYYCGEGY LDPMDYWGQG TLVTVSS    117

SEQ ID NO: 54          moltype = AA   length = 109
FEATURE                Location/Qualifiers
REGION                 1..109
                       note = Can04 VL
source                 1..109
                       mol_type = protein
                       organism = synthetic construct
SEQUENCE: 54
DIQMTQSPSS LSASVGDRVT ITCSASQGIN NYLNWYQQKP GKAPKLLIHY TSGLHAGVPS  60
RFSGSGSGTD YTLTISSLQP EDVATYYCQQ YSILPWTFGG GTKVEIKRT            109

SEQ ID NO: 55          moltype = AA   length = 531
FEATURE                Location/Qualifiers
REGION                 1..531
                       note = cyIL-1RAP(1-367)_F-chLys_Avi protein sequence
                          (including leader sequence and AVI tag)
source                 1..531
                       mol_type = protein
                       organism = synthetic construct
SEQUENCE: 55
MTLLWCVVSL YFYGILQSDA SERCDDWGLD TMRQIQVFED EPARIKCPLF EHFLKFNYST  60
AHSAGLTLIW YWTRQDRDLE EPINFRLPEN RISKEKDVLW FRPTLLNDTG NYTCMLRNTT 120
YCSKVAPPLE VVQKDSCFNS PMKLPVHKLY IEYGIQRITC PNVDGYFPSS VKPTITWYMG 180
CYKIQNFNNV IPEGMNLSFL IAFISNNGNY TCVVTYPENG RTFHLTRTLT VKVVGSPKNA 240
VPPVIHSPND HVVYEKEPGE ELLIPCTVYF SFLMDSRNEV WWTIDGKKPD DIPIDVTINE 300
SISHSRTEDE TRTQILSIKK VTSEDLKRSY VCHARSAKGE VAKAATVKQK VPAPRYTVEL 360
ACGFGATDID YKDDDDKIEG RMDKVFGRCE LAAAMKRHGL DNYRGYSLGN WVCAAKFESN 420
FNTQATNRNT DGSTDYGILQ INSRWWCNDG RTPGSRNLCN IPCSALLSSD ITASVNCAKK 480
IVSDGNGMNA WVAWRNRCKG TDVQAWIRGC RLVNSRGLND IFEAQKIEWH E         531

SEQ ID NO: 56          moltype = AA   length = 570
FEATURE                Location/Qualifiers
source                 1..570
                       mol_type = protein
                       organism = Macaca fascicularis
SEQUENCE: 56
```

```
MTLLWCVVSL YFYGILQSDA SERCDDWGLD TMRQIQVFED EPARIKCPLF EHFLKFNYST    60
AHSAGLTLIW YWTRQDRDLE EPINFRLPEN RISKEKDVLW FRPTLLNDTG NYTCMLRNTT   120
YCSKVAFPLE VVQKDSCFNS PMKLPVHKLY IEYGIQRITC PNVDGYFPSS VKPTITWYMG   180
CYKIQNFNNV IPEGMNLSFL IAFISNNGNY TCVVTYPENG RTFHLTRTLT VKVVGSPKNA   240
VPPVIHSPND HVVYEKEPGE ELLIPCTVYF SFLMDSRNEV WWTIDGKKPD DIPIDVTINE   300
SISHSRTEDE TRTQILSIKK VTSEDLKRSY VCHARSAKGE VAKAATVKQK VPAPRYTVEL   360
ACGFGATVLL VVILIVVYHV YWLEMVLFYR AHFGTDETIL DGKEYDIYVS YARNAEEEEF   420
VLLTLRGVLE NEFGYKLCIF DRDSLPGGIV TDETLSFIQK SRRLLVVLSP NYVLQGTQAL   480
LELKAGLENM ASQGNINVIL VQYKAVKETK VKELKRAKTV LTVIKWKGEK SKYPQGRFWK   540
QLQVAMPVKK SPRRSSSDEQ GLSYSSLKNV                                    570

SEQ ID NO: 57          moltype = AA  length = 478
FEATURE                Location/Qualifiers
source                 1..478
                       mol_type = protein
                       organism = Homo sapiens
SEQUENCE: 57
MTLLWCVVSL YFYGILQSDA SERCDDWGLD TMRQIQVFED EPARIKCPLF EHFLKFNYST    60
AHSAGLTLIW YWTRQDRDLE EPINFRLPEN RISKEKDVLW FRPTLLNDTG NYTCMLRNTT   120
YCSKVAFPLE VVQKDSCFNS PMKLPVHKLY IEYGIQRITC PNVDGYFPSS VKPTITWYMG   180
CYKIQNFNNV IPEGMNLSFL IALISNNGNY TCVVTYPENG RTFHLTRTLT VKVVGSPKNA   240
VPPVIHSPND HVVYEKEPGE ELLIPCTVYF SFLMDSRNEV WWTIDGKKPD DIPIDVTINE   300
SISHSRTEDE TRTQILSIKK VTSEDLKRSY VCHARSAKGE VAKAAKVKQK VPAPRYTVEL   360
ACGFGATDID YKDDDDKIEG RMDKVFGRCE LAAAMKRHGL DNYRGYSLGN WVCAAKFESN   420
FNTQATNRNT DGSTDYGILQ INSRWWCNDG RTPGSRNLCN IPCSALLSSD ITASVNCA     478

SEQ ID NO: 58          moltype = AA  length = 159
FEATURE                Location/Qualifiers
REGION                 1..159
                       note = domain 1 sequence of IL-1RacP (including leader
                         sequence and AVI and His tags)
source                 1..159
                       mol_type = protein
                       organism = synthetic construct
SEQUENCE: 58
MTLLWCVVSL YFYGILQSDA SERCDDWGLD TMRQIQVFED EPARIKCPLF EHFLKFNYST    60
AHSAGLTLIW YWTRQDRDLE EPINFRLPEN RISKEKDVLW FRPTLLNDTG NYTCMLRNTT   120
YCSKVAFPLE VVQKDISRGL NDIFEAQKIE WHEHHHHHH                          159

SEQ ID NO: 59          moltype = AA  length = 261
FEATURE                Location/Qualifiers
REGION                 1..261
                       note = domain 1/2 sequence of IL-1RacP (including leader
                         sequence and AVI and His tags)
source                 1..261
                       mol_type = protein
                       organism = synthetic construct
SEQUENCE: 59
MTLLWCVVSL YFYGILQSDA SERCDDWGLD TMRQIQVFED EPARIKCPLF EHFLKFNYST    60
AHSAGLTLIW YWTRQDRDLE EPINFRLPEN RISKEKDVLW FRPTLLNDTG NYTCMLRNTT   120
YCSKVAFPLE VVQKDSCFNS PMKLPVHKLY IEYGIQRITC PNVDGYFPSS VKPTITWYMG   180
CYKIQNFNNV IPEGMNLSFL IALISNNGNY TCVVTYPENG RTFHLTRTLT VKVVGSDISR   240
GLNDIFEAQK IEWHEHHHHH H                                             261

SEQ ID NO: 60          moltype = AA  length = 155
FEATURE                Location/Qualifiers
REGION                 1..155
                       note = domain 3 sequence of IL-1RacP (including leader
                         sequence and AVI and His tags)
source                 1..155
                       mol_type = protein
                       organism = synthetic construct
SEQUENCE: 60
MVLQTQVFIS LLLWISGAYG DGTPPVIHSP NDHVVYEKEP GEELLIPCTV YFSFLMDSRN    60
EVWWTIDGKK PDDITIDVTI NESISHSRTE DETRTQILSI KKVTSEDLKR SYVCHARSAK   120
GEVAKAAKVK DISRGLNDIF EAQKIEWHEH HHHHH                              155

SEQ ID NO: 61          moltype = AA  length = 531
FEATURE                Location/Qualifiers
REGION                 1..531
                       note = cynomolgus IL-1RacP (including leader sequence and
                         AVI tag)
source                 1..531
                       mol_type = protein
                       organism = synthetic construct
SEQUENCE: 61
MTLLWCVVSL YFYGILQSDA SERCDDWGLD TMRQIQVFED EPARIKCPLF EHFLKFNYST    60
AHSAGLTLIW YWTRQDRDLE EPINFRLPEN RISKEKDVLW FRPTLLNDTG NYTCMLRNTT   120
YCSKVAFPLE VVQKDSCFNS PMKLPVHKLY IEYGIQRITC PNVDGYFPSS VKPTITWYMG   180
```

```
CYKIQNFNNV IPEGMNLSFL IAFISNNGNY TCVVTYPENG RTFHLTRTLT VKVVGSPKNA    240
VPPVIHSPND HVVYEKEPGE ELLIPCTVYF SFLMDSRNEV WWTIDGKKPD DIPIDVTINE    300
SISHSRTEDE TRTQILSIKK VTSEDLKRSY VCHARSAKGE VAKAATVKQK VPAPRYTVEL    360
ACGFGATDID YKDDDDKIEG RMDKVFGRCE LAAAMKRHGL DNYRGYSLGN WVCAAKFESN    420
FNTQATNRNT DGSTDYGILQ INSRWWCNDG RTPGSRNLCN IPCSALLSSD ITASVNCAKK    480
IVSDGNGMNA WVAWRNRCKG TDVQAWIRGC RLVNSRGLND IFEAQKIEWH E             531

SEQ ID NO: 62              moltype = AA  length = 463
FEATURE                    Location/Qualifiers
REGION                     1..463
                           note = YKD-YTE h11C5
source                     1..463
                           mol_type = protein
                           organism = synthetic construct
SEQUENCE: 62
MPLLLLLPLL WAGALAEVQL VESGGGLVQP GGSLRLSCAA SGFTFSNYAM SWVRQAPGKG     60
LEWVATVTEG GDYNYYLDDV KGRFTISRDN AKNSLYLQMN SLRAEDTAVY YCARDDWPYF    120
FDYWGQGTLV TVSSASTKGP SVFPLAPSSK STSGGTAALG CLVKDYFPEP VTVSWNSGAL    180
TSGVHTFPAV LQSSGLYSLS SVVTVPSSSL GTQTYICNVN HKPSNTKVDK KVEPKSCDKT    240
HTCPPCPAPE LLGGPSVFLF PPKPKDTLYI TREPEVTCVV VDVSHEDPEV KFNWYVDGVE    300
VHNAKTKPRE EQYGSTYRVV SVLTVLHQDW LNGKEYKCKV SNKALPAPIE KTISKAKGQP    360
REPQVYTLPP SRDELTKNQV SLTCLVKGFY PSDIAVEWES NGQPENNYKT TPPVLDSDGS    420
FFLYSKLTVD KSRWQQGNVF SCSVMHEALH NHYTQKSLSL SPG                      463

SEQ ID NO: 63              moltype = AA  length = 230
FEATURE                    Location/Qualifiers
REGION                     1..230
                           note = YKD h11C5 h kappa
source                     1..230
                           mol_type = protein
                           organism = synthetic construct
SEQUENCE: 63
MPLLLLLPLL WAGALADIQM TQSPSSLSAS VGDRVTITCR ASENIYSNLA WYQQKPGKSP     60
KLLVYGYKNL ADGVPSRFSG SGSGTDYTLT ISSLQPEDFA TYYCQHFKTT PRTFGGGTKV    120
EIKRTVAAPS VFIFPPSDEQ LKSGTASVVC LLNNFYPREA KVQWKVDNAL QSGNSQESVT    180
EQDSKDSTYS LSSTLTLSKA DYEKHKVYAC EVTHQGLSSP VTKSFNRGEC                230

SEQ ID NO: 64              moltype = AA  length = 447
FEATURE                    Location/Qualifiers
REGION                     1..447
                           note = YKD-YTE h11C5 without leader sequence
source                     1..447
                           mol_type = protein
                           organism = synthetic construct
SEQUENCE: 64
EVQLVESGGG LVQPGGSLRL SCAASGFTFS NYAMSWVRQA PGKGLEWVAT VTEGGDYNYY     60
LDDVKGRFTI SRDNAKNSLY LQMNSLRAED TAVYYCARDD WPFYTIDYWGQ GTLVTVSSAS   120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLYITREPEV TCVVVDVSHE DPEVKFNWYV DGVEVHNAKT KPREEQYGST    300
YRVVSVLTVL HQDWLNGKEY KCKVSNKALP APIEKTISKA KGQPREPQVY TLPPSRDELT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPG                                        447

SEQ ID NO: 65              moltype = AA  length = 214
FEATURE                    Location/Qualifiers
REGION                     1..214
                           note = YKD h11C5 h kappa without leader sequence
source                     1..214
                           mol_type = protein
                           organism = synthetic construct
SEQUENCE: 65
DIQMTQSPSS LSASVGDRVT ITCRASENIY SNLAWYQQKP GKSPKLLVYG YKNLADGVPS     60
RFSGSGSGTD YTLTISSLQP EDFATYYCQH FKTTPRTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 66              moltype = AA  length = 108
FEATURE                    Location/Qualifiers
source                     1..108
                           mol_type = protein
                           organism = Homo sapiens
SEQUENCE: 66
SERCDDWGLD TMRQIQVFED EPARIKCPLF EHFLKFNYST AHSAGLTLIW YWTRQDRDLE     60
EPINFRLPEN RISKEKDVLW FRPTLLNDTG NYTCMLRNTT YCSKVAFP                  108

SEQ ID NO: 67              moltype = AA  length = 90
FEATURE                    Location/Qualifiers
source                     1..90
```

```
                        mol_type = protein
                        organism = Homo sapiens
SEQUENCE: 67
PMKLPVHKLY IEYGIQRITC PNVDGYFPSS VKPTITWYMG CYKIQNFNNV IPEGMNLSFL    60
IALISNNGNY TCVVTYPENG RTFHLTRTLT                                    90

SEQ ID NO: 68           moltype = AA   length = 107
FEATURE                 Location/Qualifiers
source                  1..107
                        mol_type = protein
                        organism = Homo sapiens
SEQUENCE: 68
PPVIHSPNDH VVYEKEPGEE LLIPCTVYFS FLMDSRNEVW WTIDGKKPDD ITIDVTINES    60
ISHSRTEDET RTQILSIKKV TSEDLKRSYV CHARSAKGEV AKAAKVK                 107

SEQ ID NO: 69           moltype = AA   length = 458
FEATURE                 Location/Qualifiers
source                  1..458
                        mol_type = protein
                        organism = Homo sapiens
SEQUENCE: 69
SERCDDWGLD TMRQIQVFED EPARIKCPLF EHFLKFNYST AHSAGLTLIW YWTRQDRDLE    60
EPINFRLPEN RISKEKDVLW FRPTLLNDTG NYTCMLRNTT YCSKVAFPLE VVQKDSCFNS   120
PMKLPVHKLY IEYGIQRITC PNVDGYFPSS VKPTITWYMG CYKIQNFNNV IPEGMNLSFL   180
IALISNNGNY TCVVTYPENG RTFHLTRTLT VKVVGSPKNA VPPVIHSPND HVVYEKEPGE   240
ELLIPCTVYF SFLMDSRNEV WWTIDGKKPD DITIDVTINE SISHSRTEDE TRTQILSIKK   300
VTSEDLKRSY VCHARSAKGE VAKAAKVKQK VPAPRYTVEL ACGFGATDID YKDDDDKIEG   360
RMDKVFGRCE LAAAMKRHGL DNYRGYSLGN WVCAAKFESN FNTQATNRNT DGSTDYGILQ   420
INSRWWCNDG RTPGSRNLCN IPCSALLSSD ITASVNCA                          458

SEQ ID NO: 70           moltype = AA   length = 496
FEATURE                 Location/Qualifiers
source                  1..496
                        mol_type = protein
                        organism = Macaca fascicularis
SEQUENCE: 70
SERCDDWGLD TMRQIQVFED EPARIKCPLF EHFLKFNYST AHSAGLTLIW YWTRQDRDLE    60
EPINFRLPEN RISKEKDVLW FRPTLLNDTG NYTCMLRNTT YCSKVAFPLE VVQKDSCFNS   120
PMKLPVHKLY IEYGIQRITC PNVDGYFPSS VKPTITWYMG CYKIQNFNNV IPEGMNLSFL   180
IAFISNNGNY TCVVTYPENG RTFHLTRTLT VKVVGSPKNA VPPVIHSPND HVVYEKEPGE   240
ELLIPCTVYF SFLMDSRNEV WWTIDGKKPD DIPIDVTINE SISHSRTEDE TRTQILSIKK   300
VTSEDLKRSY VCHARSAKGE VAKAATVKQK VPAPRYTVEL ACGFGATDID YKDDDDKIEG   360
RMDKVFGRCE LAAAMKRHGL DNYRGYSLGN WVCAAKFESN FNTQATNRNT DGSTDYGILQ   420
INSRWWCNDG RTPGSRNLCN IPCSALLSSD ITASVNCAKK IVSDGNGMNA WVAWRNRCKG   480
TDVQAWIRGC RLVNSR                                                  496

SEQ ID NO: 71           moltype = AA   length = 15
FEATURE                 Location/Qualifiers
REGION                  1..15
                        note = AVI tag
source                  1..15
                        mol_type = protein
                        organism = synthetic construct
SEQUENCE: 71
GLNDIFEAQK IEWHE                                                    15

SEQ ID NO: 72           moltype = AA   length = 6
FEATURE                 Location/Qualifiers
REGION                  1..6
                        note = His tag
source                  1..6
                        mol_type = protein
                        organism = synthetic construct
SEQUENCE: 72
HHHHHH                                                               6

SEQ ID NO: 73           moltype = AA   length = 5
FEATURE                 Location/Qualifiers
VARIANT                 4
                        note = Any amino acid
source                  1..5
                        mol_type = protein
                        organism = synthetic construct
SEQUENCE: 73
GSAXH                                                                5

SEQ ID NO: 74           moltype = AA   length = 17
FEATURE                 Location/Qualifiers
VARIANT                 6..10
```

```
                        note = Any amino acid
source                  1..17
                        mol_type = protein
                        organism = synthetic construct
SEQUENCE: 74
RILTYXXXXX YAESVKG                                                      17

SEQ ID NO: 75           moltype = AA  length = 5
FEATURE                 Location/Qualifiers
VARIANT                 4
                        note = V or M
source                  1..5
                        mol_type = protein
                        organism = synthetic construct
SEQUENCE: 75
GSAXH                                                                   5

SEQ ID NO: 76           moltype = AA  length = 17
FEATURE                 Location/Qualifiers
VARIANT                 6
                        note = S or G
VARIANT                 7
                        note = S or G
VARIANT                 8
                        note = T or I
VARIANT                 9
                        note = T or A
VARIANT                 10
                        note = Q or T
source                  1..17
                        mol_type = protein
                        organism = synthetic construct
SEQUENCE: 76
RILTYXXXXX YAESVKG                                                      17
```

IL-1 RECEPTOR ACCESSORY PROTEIN-INHIBITING ANTIBODIES AND ANTIGEN-BINDING FRAGMENTS THEREOF

RELATED APPLICATIONS

This application is a divisional of U.S. application Ser. No. 17/664,349 filed May 20, 2022, which claims the benefit of and priority to European patent applications 21175216.7 filed May 21, 2021, and 21192805.6 filed Aug. 24, 2021, each entitled "Anti IL-1 Receptor Accessory Protein Antibodies." The contents of each of these applications are expressly incorporated herein by reference in their entirety.

SEQUENCE LISTING

The instant application contains a Sequence Listing which has been submitted electronically in XML format and is hereby incorporated by reference in its entirety. The XML copy, created on Feb. 29, 2024, is named 14894_0078-01000_SL.xml and is 112,248 bytes in size.

FIELD

The present disclosure relates to antibodies and antigen binding fragments thereof which bind to the cytokine receptor IL-1R accessory protein, hereinafter IL-1RAcP, particularly human IL-1RAcP. The IL-1RAcP antibodies and antigen binding fragments of the disclosure exhibit distinct properties, particularly distinct combinations of properties, as compared with IL-1RAcP antibodies described in the prior art.

BACKGROUND

IL-1RAcP (Interleukin-1 receptor accessory protein; alternative name is IL-1R3) was discovered as the co-receptor of the interleukin-1 receptor (IL-1R1) for being a key component in IL-1 signalling. During the years it was discovered that IL-1RAcP is not only crucial for IL-1 signalling but also for IL-33 signalling (by serving as a co-receptor for the IL-33/ST2 complex) and for IL-36 signalling (by serving as a co-receptor for the IL-36/IL-1Rrp2 complex).

IL-1RAcP is the common co-receptor chain associated to three distinct cognate receptors (IL-1R1, ST2/IL-1RL1 and IL-36R/IL-1Rrp2/IL-1RL2) and required for the signaling pathways of the mentioned six cytokines of the IL-1 family (IL-1α, IL-1β, IL-33, IL-36α, IL-36β and IL-36γ).

IL-1-Receptor Accessory Protein (IL-1RAcP) is an essential component for all three signalling pathways as it is recruited to form a ternary receptor signalling complex after each cytokine is bound to its own primary receptor chain (reviewed in Palomo et al 2015). Upon binding of the cytokine to its respective specific receptor ((IL-1R1, ST2/IL-1RL1 and IL-36R/IL-1Rrp2/IL-1RL2) the complex interacts with IL-TRAcP and this enables signalling, leading to inflammatory responses, proliferation, cytokine and chemokine release and immune cell differentiation.

IL-1RAcP is expressed broadly at low levels, and the activation of the signalling cascade is decided by the level of the respective cytokines, together with the presence of the primary receptors. The IL-1R is also rather ubiquitously expressed, whereas the IL-33 receptor (ST2) is restricted to T-cells, NK and NKT cells, and the IL-36R is restricted to epithelial cells upon stimulation. IL-1 is produced by several immune and non-immune cells, IL-33 and IL-36 are produced by various epithelial cells with IL-33 acting as alarmin, being released upon cell damage, cell death and infections. There are clear medical indications where the single cytokine blockade is not sufficient, the present disclosure shows superior effect by blockade of multiple cytokine signalling.

IL-1RAcP consists of three extracellular immunoglobulin-like domains, a short transmembrane domain and a cytoplasmic domain characterized by a TIR domain essential for the signalling via the MyD88 adaptor molecule. The six cytokines of the IL-1 family bind to their specific high-affinity receptor chains, which are transmembrane proteins structurally similar to IL-1RAcP with a cytoplasmic TIR domain (e.g. IL-1R1 for IL-1α and IL-1β, ST2 for IL-33 and IL-36R for IL-36α, IL-36β and IL-36γ). Upon ligand binding to its specific high-affinity receptor chain, a structural change occurs allowing IL-1RAcP to bind to the ligand-high affinity receptor complex. This trimeric ligand-receptors complex allows the two TIR domains to get in close proximity enabling the recruitment of the adaptor molecule MyD88, and hence to initiate the signalling cascade leading to the activation of MAPK and NF-kB transcription factors, which triggers a cascade of inflammatory and immune responses, including the production of numerous cytokines, chemokines, enzymes and adhesion molecules. Thus, IL-1 family cytokines rely on the heterotrimeric receptor complex to exert their effects on target cells.

IL-1RAcP consists of an extracellular portion harbouring three structurally distinguishable domains (D1, D2, D3), D3 being closest to the cell membrane. Sequence alignments based on publicly accessible information (UniProt) revealed a sequence identity of ~99% in the extracellular portion to cynomolgus monkey and a sequence identity of only ~86% to mouse IL-1RAcP.

Prior disclosures of anti-IL-1RAcP antibodies in skin diseases are for example WO2020037154, which binds to domain 3 of the human IL-1RAcP and shows partial inhibition of the IL-1RAcP induced activation of the signalling.

WO2015132602 discloses antibodies against human IL-1RAcP for the treatment of tumours. The antibody "CAN04" as disclosed is used in the present disclosure as a comparative antibody. CAN04 is a mouse derived antibody which binds domain 2 of the human IL-1RAcP, cross reacts with the cynomolgus IL-1RAcP, and shows inhibition of the IL-1RAcP induced activation of the IL-1α, IL-1b and IL-36 signalling. The CAN04 antibody induces ADCC activation. WO2016020502, WO2018071910, WO2018231827, WO2017191325, and WO2019028190 disclose antibodies different from the present disclosure for use in cancer treatment.

Extracellular soluble form of IL-1RAcP (sIL-1RAcP), which is generated by alternative splicing, is abundantly present in the circulation. The expression of both membrane bound and soluble IL-1RAcP is constant even in pathological inflammatory conditions. The sequence of sIL-1RAcP is identical to the sequence of the extracellular portion of the membrane bound IL-1RAcP receptor chain and the antibodies of the present disclosure are directed specifically against the extracellular domain of the IL-1RAcP receptor chain, thus having affinity to both membrane and soluble forms of IL-1RAcP.

The present disclosure provides fully human anti-IL-1RAcP antibodies for use in treating inflammatory conditions, in particular inflammatory conditions in the skin. The antibodies bind with high affinity to the human IL-1RAcP, to a unique epitope on domain 2 of the IL-1RAcP, shows cross-reactivity to non-human primate IL-1RAcP exemplified by the cynomolgus IL-1RAcP, shows complete inhibition of all cytokines induced IL-1RAcP signalling and without ADCC function in its mode of action.

SUMMARY

The present disclosure provides novel antibodies and antigen binding fragments. The antibodies and antigen binding fragments disclosed herein bind to human IL-1RAcP and also cross-react with IL-1RAcP from the cynomolgus monkey. The antibodies are capable of inhibition IL-1, IL-33, and/or IL-36 signaling pathways, including signaling stimulated by binding of one or more of the following agonists: IL-1 a, IL-1 b, IL-33, IL-36a, IL-36b, and IL-36g. The present disclosure also provides methods of treating diseases and conditions responsive to inhibition of IL-1, IL-33, and/or IL-36 signaling.

In one embodiment, the disclosure provides an antibody or antigen binding fragment which binds specifically to IL-1RAcP wherein the antibody or antigen binding fragment cross-competes with an antibody or antigen binding fragment comprising:
 (a) the HCDR1 region of SEQ ID NO: 4, the HCDR2 region of SEQ ID NO: 5, the HCDR3 region of SEQ ID NO: 6, the LCDR1 region of SEQ ID NO: 1, the LCDR2 region of SEQ ID NO: 2 and the LCDR3 region of SEQ ID NO: 3; or
 (b) the HCDR1 region of SEQ ID NO: 12, the HCDR2 region of SEQ ID NO: 13, the HCDR3 region of SEQ ID NO: 14, the LCDR1 region of SEQ ID NO: 9, the LCDR2 region of SEQ ID NO: 10 and the LCDR3 region of SEQ ID NO: 11.

In one embodiment, the disclosure provides an antibody or antigen binding fragment which binds specifically to IL-1RAcP according to the above aspect, wherein said antibody or antigen binding fragment comprises
 (a) a HCDR1 region comprising the amino acid sequence of SEQ ID NO: 4, a HCDR2 region comprising the amino acid sequence of SEQ ID NO: 5, a HCDR3 region comprising the amino acid sequence of SEQ ID NO: 6, a LCDR1 comprising the amino acid sequence of SEQ ID NO: 1, the LCDR2 comprising the amino acid sequence of SEQ ID NO: 2 and the LCDR3 comprising the amino acid sequence of SEQ ID NO: 3; or
 (b) the HCDR1 comprising the amino acid sequence of SEQ ID NO: 12, the HCDR2 comprising the amino acid sequence of SEQ ID NO: 13, the HCDR3 comprising the amino acid sequence of SEQ ID NO: 14, the LCDR1 comprising the amino acid sequence of SEQ ID NO: 9, the LCDR2 comprising the amino acid sequence of SEQ ID NO: 10 and the LCDR3 comprising the amino acid sequence of SEQ ID NO: 11.

In one embodiment, the disclosure provides an antibody or antigen binding fragment according to any of the aspects above, wherein said antibody or antigen binding fragment comprises:
 (a) the HCDR1 region of SEQ ID NO: 4, the HCDR2 region of SEQ ID NO: 5, the HCDR3 region of SEQ ID NO: 6, the LCDR1 region of SEQ ID NO: 1, the LCDR2 region of SEQ ID NO: 2 and the LCDR3 region of SEQ ID NO: 3; or
 (b) the HCDR1 region of SEQ ID NO: 12, the HCDR2 region of SEQ ID NO: 13, the HCDR3 region of SEQ ID NO: 14, the LCDR1 region of SEQ ID NO: 9, the LCDR2 region of SEQ ID NO: 10 and the LCDR3 region of SEQ ID NO: 11.

In one embodiment, the disclosure provides an antibody or antigen binding fragment according to any of the preceding aspects, wherein the antibody or antigen binding fragment binds specifically to human IL-1RAcP.

In one embodiment, the disclosure provides an antibody or antigen binding fragment according to the aspect above, wherein the antibody or antigen binding fragment binds specifically to human IL-1RAcP and Cynomolgus IL-1RAcP.

In one embodiment, the disclosure provides an antibody or antigen binding fragment according to any of the preceding aspects wherein said antibody or antigen binding fragment comprises at least one heavy chain variable domain (VH) of SEQ ID NO: 7 and at least one light chain variable domain (VL) selected from the following: the VH comprising the amino acid sequence of SEQ ID NO: 7 or an amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical thereto, and at least one light chain variable domain (VL) of SEQ ID NO: 8, or an amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical thereto.

In one embodiment, the disclosure provides an antibody or antigen binding fragment according to any of the preceding aspects wherein said antibody or antigen binding fragment comprises at least one heavy chain variable domain (VH) of SEQ ID NO: 7 and at least one light chain variable domain (VL) of SEQ ID NO: 8

In one embodiment, the disclosure provides an antibody or antigen binding fragment according to any of the preceding aspects wherein said antibody or antigen binding fragment comprises at least one heavy chain variable domain (VH) of SEQ ID NO: 15 and at least one light chain variable domain (VL) selected from the following: the VH comprising the amino acid sequence of SEQ ID NO: 15 or an amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical thereto, and at least one light chain variable domain (VL) of SEQ ID NO: 16, or an amino acid sequence at least 80%, 81%, 82%, 83%, 84%, 85%, 86%, 87%, 88%, 89%, 90%, 91%, 92%, 93%, 94%, 95%, 96%, 97%, 98%, 99% identical thereto.

In one embodiment, the disclosure provides an antibody or antigen binding fragment according to any of the preceding aspects, wherein said antibody or antigen binding fragment comprises at least one heavy chain variable domain (VH) of SEQ ID NO: 15 and at least one light chain variable domain (VL) of SEQ ID NO: 16.

In one embodiment, the disclosure provides an antibody or antigen binding fragment according to one of the preceding aspects, wherein said antibody or antigen binding fragment is an isolated antibody or antigen binding fragment.

In one embodiment, the disclosure provides an antibody or antigen binding fragment according to one of the preceding aspects, wherein said antibody or antigen binding fragment is a recombinant antibody or antigen binding fragment.

In one embodiment, the disclosure provides an antibody or antigen binding fragment according to one of the preceding aspects for use in the treatment of a subject in need thereof.

In one embodiment, the disclosure provides a nucleic acid composition comprising a nucleic acid sequence or a plurality of nucleic acid sequences encoding the antibody or antigen binding fragment according to any one of aspects above.

In one embodiment, the disclosure provides a vector composition comprising a vector or a plurality of vectors comprising the nucleic acid sequence or plurality of nucleic acid sequences of the aspect above.

In one embodiment, the disclosure provides a cell comprising the vector composition of the aspect above.

In one embodiment, the disclosure provides a pharmaceutical composition comprising the antibody or antigen binding fragment according to one of the aspects above and a pharmaceutically acceptable carrier or excipient.

BRIEF DESCRIPTION OF DRAWINGS

FIG. 8D: Inhibition of signalling by anti-IL1RAcP mAbs in primary human dermal fibroblast stimulated with 2 pM IL-1a.

DEFINITIONS

Figure 1A:
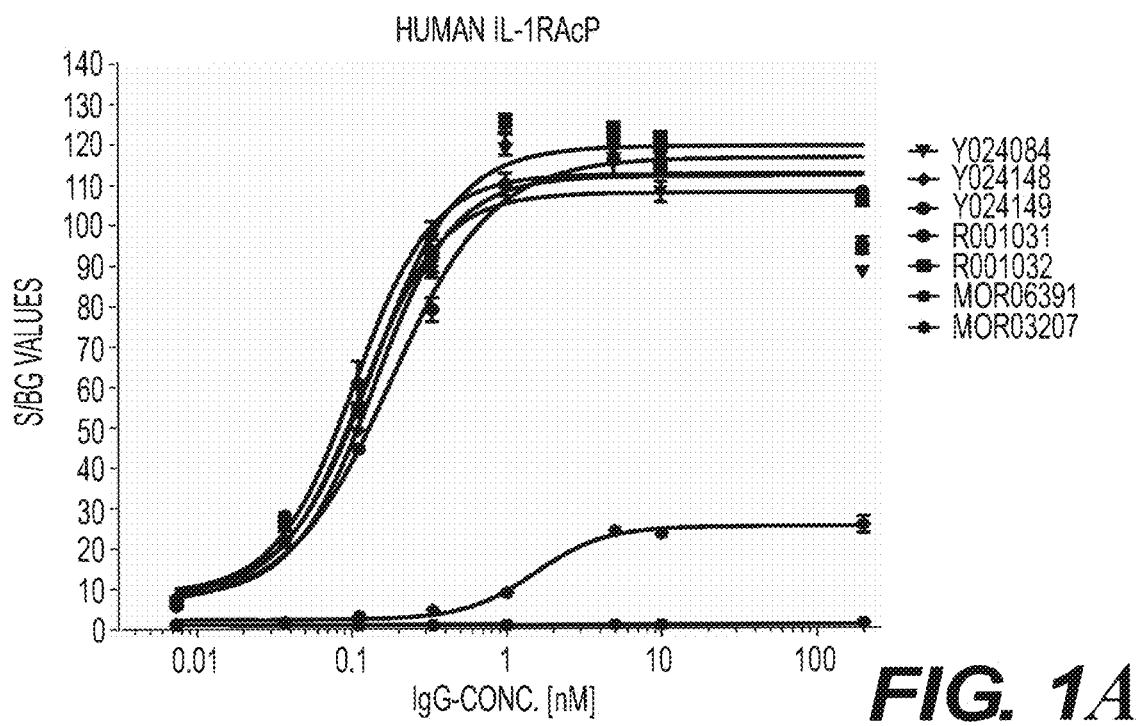
FIG. 1A: Various concentrations of the antibodies in the IgG1f_AEASS format were tested for binding to human (AG-12210) IL-1RAcP (IL-1RAP).

The terms "antibody" or "antibodies" refer to immunoglobulin molecules comprising four polypeptide chains: two heavy chains and two light chains. Each heavy chain is comprised of a heavy chain variable region (abbreviated herein as HCVR or VH) and a heavy chain constant region. The heavy chain constant region is comprised of three domains, CH1, CH2, and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4.

The term "IL-1RAcP antibodies" is used herein to refer to antibodies which exhibit immunological specificity for IL-1RAcP protein, including human IL-1RAcP and in some cases species homologues thereof.

"IL-1RAcP": Human IL-1 RAcP (21-367) is described in Uniprot ID: Q9NPH3.

The sequence including the leader sequence is the following:

(SEQ ID NO: 57)
MTLLWCVVSLYFYGILQSDASERCDDWGLDTMRQIQVFEDEPARIKCPL

FEHFLKFNYSTAHSAGLTLIWYWTRQDRDLEEPINFRLPENRISKEKDV

LWFRPTLLNDTGNYTCMLRNTTYCSKVAFPLEVVQKDSCFNSPMKLPVH

KLYIEYGIQRITCPNVDGYFPSSVKPTITWYMGCYKIQNFNNVIPEGMN

LSFLIALISNNGNYTCVVTYPENGRTFHLTRTLTVKVVGSPKNAVPPVI

HSPNDHVVYEKEPGEELLIPCTVYFSFLMDSRNEVWWTIDGKKPDDITI

-continued
DVTINESISHSRTEDETRTQILSIKKVTSEDLKRSYVCHARSAKGEVAK

AAKVKQKVPAPRYTVELAcGFGATDIDYKDDDDKIEGRMDKVFGRCELA

AAMKRHGLDNYRGYSLGNWVCAAKFESNFNTQATNRNTDGSTDYGILQI

NSRWWCNDGRTPGSRNLCNIPCSALLSSDITASVNCA.

The domains of the human IL-1RAcP are the following:

Domain 1 (21-128):
(SEQ ID NO: 66)
SERCDDWGLDTMRQIQVFEDEPARIKCPLFEHFLKFNYSTAHSAGLTLI
WYWTRQDRDLEEPINFRLPENRISKEKDVLWFRPTLLNDTGNYTCMLRN
TTYCSKVAFP.

Domain 1 including leader sequence and AVI and His tags: SEQ ID NO: 58;
Domain 1/2 sequence of IL-1RacP including leader sequence and AVI and His tags: SEQ ID NO: 59;

Domain 2 (141-230):
(SEQ ID NO: 67)
PMKLPVHKLYIEYGIQRITCPNVDGYFPSSVKPTITWYMGCYKIQNENN
VIPEGMNLSFLIALISNNGNYTCVVTYPENGRTFHLTRTLT;

Domain 3 (242-348):
(SEQ ID NO: 68)
PPVIHSPNDHVVYEKEPGEELLIPCTVYFSFLMDSRNEVWWTIDGKKPD
DITIDVTINESISHSRTEDETRTQILSIKKVTSEDLKRSYVCHARSAKG
EVAKAAKVK;

Domain 3 sequence of IL-1RacP (including leader sequence and AVI and His tags): SEQ ID NO: 60.
Cynomolgus IL-1RAcP (21-367) is described in UniProt ID A0A2K5X5J5.
cyIL-1RAP(1-367)_F-chLys_Avi protein sequence (including leader sequence and AVI tag): SEQ ID NO: 55.

"Binding Site"—As used herein, the term "binding site" comprises a region of a polypeptide which is responsible for binding to a target antigen of interest (e.g., IL-1RAcP). Binding domains comprise at least one binding site. Exemplary binding domains include an antibody variable domain. The antibody molecules of the disclosure may comprise a single binding site or multiple (e.g., two, three or four) binding sites.

"Conservative amino acid substitution"—A "conservative amino acid substitution" is one in which the amino acid residue is replaced with an amino acid residue having similar physico-chemical properties. Exemplary groups of such amino acids having similar physico-chemical properties include amino acids having basic side chains (e.g., lysine, arginine, histidine), amino acids having acidic side chains (e.g., aspartic acid, glutamic acid), amino acids having uncharged polar side chains (e.g., glycine, asparagine, glutamine, serine, threonine, tyrosine, cysteine), amino acids having nonpolar side chains (e.g., alanine, valine, leucine, isoleucine, proline, phenylalanine, methionine, tryptophan), amino acids having beta-branched side chains (e.g., threonine, valine, isoleucine) and amino acids having aromatic side chains (e.g., tyrosine, phenylalanine, tryptophan, histidine).

"Heavy chain constant region"—As used herein, the term "heavy chain constant region" includes amino acid sequences derived from the constant domains of an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, an antibody or antigen binding fragment of the disclosure may comprise the Fc portion of an immunoglobulin heavy chain (e.g., a hinge portion, a CH2 domain, and a CH3 domain). In another embodiment, an antibody or antigen binding fragment of the disclosure may lack at least a portion of a constant domain (e.g., all or part of a CH2 domain). In certain embodiments, at least one, and preferably all, of the constant domains are derived from a human immunoglobulin heavy chain. For example, in one preferred embodiment, the heavy chain constant region comprises a fully human hinge domain. In other preferred embodiments, the heavy chain constant region comprising a fully human Fc portion (e.g., hinge, CH2 and CH3 domain sequences from a human immunoglobulin).

In certain embodiments, the constituent constant domains of the heavy chain constant region are from different immunoglobulin molecules. For example, a heavy chain constant region of a polypeptide may comprise a CH2 domain derived from an IgG1 molecule and a hinge region derived from an IgG3 or IgG4 molecule. In other embodiments, the constant domains are chimeric domains comprising portions of different immunoglobulin molecules. For example, a hinge may comprise a first portion from an IgG1 molecule and a second portion from an IgG3 or IgG4 molecule. As set forth above, it will be understood by one of ordinary skill in the art that the constant domains of the heavy chain constant region may be modified such that they vary in amino acid sequence from the naturally occurring (wild-type) immunoglobulin molecule. That is, the polypeptides of the disclosure may comprise alterations or modifications to one or more of the heavy chain constant domains (CH1, hinge, CH2 or CH3) and/or to the light chain constant region domain (CL). Exemplary modifications include additions, deletions or substitutions of one or more amino acids in one or more domains.

Other variants of the constant regions are related to CDC and/or ADCC activity. Fc region variants and their characteristics are known in the art.

"Chimeric"—A "chimeric" protein is an engineered polypeptide that is encoded by a polynucleotide sequence comprising at least two different genes that are not found to encode a single protein in nature. The chimeric protein may comprise amino acid sequences that normally exist in separate proteins that are brought together in the engineered polypeptide or they may normally exist in the same protein but are placed in a new arrangement in the engineered polypeptide. A chimeric protein may be created, for example, by chemical synthesis, or by creating and translating a polynucleotide in which the peptide regions are encoded in the desired relationship. Exemplary chimeric antibodies encompassed by the disclosure include fusion proteins comprising VH and VL domains, or humanised variants thereof, fused to the constant domains of a human antibody, e.g. human IgG1, IgG2, IgG3 or IgG4.

"Variable region" or "variable domain". The terms "variable region" and "variable domain" are used herein interchangeably and are intended to have equivalent meaning. The term "variable" refers to the fact that certain portions of the variable domains VH and VL differ extensively in sequence among antibodies and are used in the binding and specificity of each particular antibody for its target antigen.

"CDR" or "complementarity determining region"—As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

"Framework region"—The term "framework region" or "FR region" as used herein, includes the amino acid residues that are part of the variable region, but are not part of the CDRs (e.g., using the Kabat definition of CDRs). In some embodiments, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a R-sheet conformation and the CDRs form loops which connect, and in some cases form part of, the R-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Antigen-binding fragment"—The term "antigen-binding fragment", as used in the context of antibodies of the disclosure, refers to a part or portion of an antibody or antibody chain comprising fewer amino acid residues than a full-length antibody or antibody chain. The term "antigen-binding fragment" refers to a polypeptide fragment of an immunoglobulin or antibody that binds the same antigen or competes with the full-length antibody (i.e., with the full-length antibody from which they were derived) for antigen binding (i.e., specific binding to IL-1RAcP). As used herein, the term "antigen-binding fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

"Specificity"—The term "specificity" refers to the ability to bind (e.g., immunoreact with) a given target, e.g., IL-1RAcP. A polypeptide may be monospecific and contain one or more binding sites which specifically bind a target or a polypeptide may be multispecific and contain two or more binding sites which specifically bind the same or different targets.

"Engineered"—As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the disclosure are engineered, including for example, humanized and/or chimeric antibodies, and antibodies which have been engineered to improve one or more properties, such as antigen binding, stability/half-life or effector function.

"Affinity variants"—As used herein, the term "affinity variant" refers to a variant antibody which exhibits one or more changes in amino acid sequence compared to a reference antibody, wherein the affinity variant exhibits an altered affinity for the target antigen in comparison to the reference antibody. For example, affinity variants will exhibit a changed affinity for IL-1RAcP, as compared to the reference IL-1RAcP antibody. Preferably the affinity variant will exhibit improved affinity for the target antigen, e.g. IL-1RAcP, as compared to the reference antibody. Affinity variants typically exhibit one or more changes in amino acid sequence in the CDRs, as compared to the reference antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"scFv" or "scFv fragment"—An scFv or scFv fragment means a single chain variable fragment. An scFv is a fusion protein of a VH domain and a VL domain of an antibody connected via a linker.

As used herein the term "binds specifically to", "specifically binds to", is "specific to/for" or "specifically recognizes", or the like, refers to measurable and reproducible interactions such as binding between a target and an antibody or antigen binding fragment, which is determinative of the presence of the target in the presence of a heterogeneous population of molecules including biological molecules. For example, an antibody or antigen binding fragment that specifically binds to a target (which can be an antigen or an epitope of an antigen) is an antibody or antigen binding fragment that binds this target with greater affinity, avidity, more readily, and/or with greater duration than it binds to other targets. In certain embodiments, an antibody or antigen binding fragment specifically binds to an epitope on a protein that is conserved among the protein from different species. In another embodiment, specific binding can include, but does not require exclusive binding. The antibodies or antigen binding fragments disclosed herein specifically bind to human IL-1RAcP. Preferably, the disclosed antibodies or antigen binding fragments specific for human IL-1RAcP specifically bind to IL-1RAcP of another species, such as IL-1RAcP cynomolgus monkey. Methods for determining whether two molecules specifically bind are well known in the art and include, for example, a standard ELISA assay and as described in this application. As used herein, the term "affinity" refers to the strength of interaction between the polypeptide and its target at a single site. Within each site, the binding region of the polypeptide interacts through weak non-covalent forces with its target at numerous sites; the more interactions, the stronger the affinity. The binding affinity of an antibody or antigen binding fragment thereof for its respective antigen can be determined experimentally using techniques known in the art. For example, Biacore® instruments measure affinity based on the immobilization of a target protein or antigen on a biosensor chip while the antibody or antigen binding fragment is passed over the immobilized target under specific flow conditions. These experiments yield kon and koff measurements, which can be translated into KD values, wherein KD is the equilibrium constant for the dissociation of an antigen with an antibody or fragment thereof. The smaller the KD value, the stronger the binding interaction between an antibody and its target antigen. As noted above, the affinity of an antibody may be determined by Biacore®, for example using the protocol described elsewhere herein.

The term "isolated" refers to a compound, which can be e.g. an antibody or antibody fragment, that is substantially free of other antibodies or antigen binding fragments having different antigenic specificities. Moreover, an isolated antibody or antigenic binding fragment may be substantially free of other cellular material and/or chemicals. Thus, in some aspects, antibodies provided in the present disclosure are isolated antibodies which have been separated from antibodies with a different specificity. An isolated antibody may be a monoclonal antibody. An isolated antibody may be a recombinant monoclonal antibody. An isolated antibody that specifically binds to an epitope, isoform or variant of a target may, however, have cross-reactivity to other related antigens, e.g., from other species (e.g., species homologs).

"Cross competes" means the ability of an antibody, antigen binding fragment or other antigen binding moieties to interfere with the binding of other antibodies, antigen binding fragments or antigen binding moieties to a specific antigen in a standard competitive binding assay. The ability or extent to which an antibody, antigen binding fragment or other antigen-binding moieties is able to interfere with the binding of another antibody, antigen binding fragment or antigen-binding moieties to a specific antigen, and, therefore whether it can be said to cross-compete according to the disclosure, can be determined using standard competition binding assays. One suitable assay involves the use of the Biacore® technology (e.g. by using the Biacore® 3000 instrument (Biacore®, Uppsala, Sweden)), which can measure the extent of interactions using surface plasmon resonance technology. Another assay for measuring cross-competing uses an ELISA-based approach. A high throughput process for "epitope binning" antibodies based upon their cross-competition is described in International Patent Application No. WO 2003/48731. Cross-competition is present if the antibody or antigen binding fragment under investigation reduces the binding of one of the antibodies described in Table 1 to IL-1RAcP by about 60% or more, about 70% or more, about 80% or more and more specifically by 90% or more, and if one of the antibodies described in Table 1 reduces the binding of said antibody or antigen binding fragment to IL-1RAcP by about 60% or more, about 70% or more, about 80% or more and more specifically by 90% or more.

The term "epitope" includes any proteinacious region which is specifically recognized by an antibody or fragment thereof or a T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

"Binds the same epitope as" means the ability of an antibody, antigen binding fragment or other antigen-binding moiety to bind to a specific antigen and binding to the same epitope as the exemplified antibody when using the same epitope mapping technique for comparing the antibodies. The epitopes of the exemplified antibody and other antibodies can be determined using epitope mapping techniques. Epitope mapping techniques are well known in the art. For example, conformational epitopes are readily identified by determining spatial conformation of amino acids such as by, e.g., hydrogen/deuterium exchange, x-ray crystallography and two dimensional nuclear magnetic resonance.

Unless otherwise stated in the present application, percent (%) sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. For example, it is possible to use the BLAST program, "BLAST 2 sequences" (Tatusova et al., "Blast 2 sequences—a new tool for comparing protein and nucleotide sequences", FEMS Microbiol Lett. 174:247-250), the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program In the context of the present disclosure inhibition of signalling initiated by one or more of IL-1α, IL-1β, IL-33, IL-36α, IL-36P, and IL-36y agonist binding to its cognate receptor means a decline in signal by at least 90%, at least 91%, at least 92%, at least 93%, at least 94%, at least 95%, at least 96%, at least 97%, at least 98%, at least 99%, or about 100% compared to signaling in the reference state. In embodiments the term "blocking" or "full inhibition" is used, which means that in the assay used, the inhibition of the signaling is above 98%, above 99% or about 100%. In some embodiments and depending on the specific assays, there is a basal signalling level, which remains.

EMBODIMENTS

The present disclosure improves upon the state of the art by providing antibodies, or antigen binding fragments thereof, which bind to the cytokine receptor IL-1RAcP, and exhibit properties that are superior to IL-1RAcP antibodies described in the prior art. The antibodies or antigen binding fragments thereof typically exhibit combinations of properties that are distinct and in certain cases superior, to the properties of the prior art IL-1RAcP antibodies. The properties of these antibodies can be particularly advantageous with regard to use in human therapy, particularly for the treatment of disorders or conditions relating to IL1RAcP signalling. In some embodiments, the disorders or conditions are dermatological conditions such as hidradenitis suppurativa, palmoplantar pustulosis, pyoderma gangrenosum and related syndromes (e.g. pyogenic arthritis, pyoderma gangrenosum, and acne (PAPA) syndrome; pyoderma gangrenosum, acne, and suppurative hidradenitis (PASH) syndrome); pyogenic arthritis, acne, pyoderma gangrenosum, and suppurative hidradenitis (PAPASH)) as well as systemic sclerosis, inflammatory nodulocystic acne, and atopic dermatitis.

Also diseases such as Papulopustular Rosacea, Sweet's Syndrome, Chronic Spontaneous Urticaria, Bullous Pemphigoid, Dermatomyositis, Contact Dermatitis, Psoriasis, pustular palmoplantar psoriasis, Generalized Pustular Psoriasis, Juvenile Psoriasis, Vitiligo, Pemphigus Vulgaris, Netherton syndrome, neutrophilic hair diseases, Acne vulgaris, Neutrophilic Asthma and Chronic Obstructive Pulmonary Disease, graft versus host disease (GVHD), Psoriatic Arthritis, Rheumatoid Arthritis, SAPHO syndrome, Sjögrens syndrome, myocarditis, Ulcerative Colitis, Crohn's Disease, Asthma, Epidermolysis Bullosa, Cryopyrin-associated periodic syndromes (inflammasome driven), Muckle-Wells syndrome, Deficiency of IL-1-receptor antagonist (DIRA), Systemic Juvenile Idiopathic Arthritis, Hyper IgD syndrome, Bechet's disease, acute and chronic Gout, Schnitzler's syndrome, adult-onset Still's disease, Aggressive periodontitis cases, Liver diseases, Endometriosis and steroid-sensitive nephrotic syndrome are described as being connected to the pathways related to IL-1RAcP (see also, e.g., Wolk et. al., Br. J. Dermatol. 2020; Boraschi et. al. Immunol. Rev 2018; Striz et al. Clin Science 2017; Dinarello et al, Nat. Rev. Drug Discov. 2012; Palomo et al. Cytokine 2015; Xu et. al., Front Immunol 2019; Tavakolpour et. al. Cytokine 2020; Machura et al. BioMed. Research International 2013).

The preferred IL-1RAcP antibodies and antigen binding fragments of the disclosure exhibit a combination of properties that render them superior to IL-1RAcP antibodies described in the prior art. Preferred IL-1RAcP antibodies and antigen binding fragments of the disclosure may exhibit the following combination of properties which can be isolated or combined with other embodiments of this disclosure:

In an embodiment, the present disclosure provides an antibody, or an antigen binding fragment thereof, which binds to human IL-1RAcP, wherein the antibody or antigen binding fragment thereof binds to an epitope within the domain 2 of the IL-1RAcP.

In an embodiment, the present disclosure provides antibodies or antigen binding fragments which binds to the same epitope as the antibodies or antigen binding fragments as disclosed herein.

In an embodiment, the present disclosure provides antibodies or antigen binding fragments which competes with the antibodies or antigen binding fragments as disclosed herein.

In an embodiment of the present disclosure the antibody or antigen binding fragments thereof is a monoclonal antibody or antigen binding fragment.

In an embodiment of the present disclosure the antibody or antigen binding fragment is a human, humanized or chimeric antibody or antigen binding fragment. In another embodiment of the present disclosure the antibody or antibody fragment is of the IgG isotype.

In another embodiment the antibody or antibody fragment is IgG1.

In an embodiment, the antibodies or antigen binding fragments thereof possess one or more additional properties selected from the following:
(a) the antibody binds to human IL-1RAcP with a monovalent binding affinity of about $25 \times 10^{-12}$ M or less; wherein the binding affinity is measured by SPR Biacore®;
(b) the antibody binds to cynomolgus IL-1RAcP with a monovalent binding affinity of about $10 \times 10^{-12}$ M or less; wherein the binding affinity is measured by SPR Biacore®;
(c) the antibody binds to an novel epitope on domain 2 of the IL-1RAcP;
(d) the antibody fully inhibits the signalling from all cytokines utilising the IL-1RAcP as co-receptor for signalling—as tested in the relevant cell types described in the present application;
(e) the antibody shows blocking of IL-1b induced signaling in human explant skin;
(f) the antibody cross-reacts with a cynomolgus monkey IL-1RAcP polypeptide of SEQ ID NO: 61; and
(g) the antibody binds to sIL-1RAcP.

In some embodiments, the disclosed antibody or antigen binding fragment specifically binds to human IL-1RAcP, with high affinity. In embodiments the binding affinity is in the range of 25 picomolar or less.

In some embodiments the disclosed antibody or antigen binding fragment specifically binds to cynomolgus monkey IL-1RAcP with high affinity. In embodiments the binding affinity ($K_D$) is in the range of below 10 pM, preferably below 8 pM;

In some embodiments, the preferred IL-1RAcP antibodies of the disclosure bind to human IL-1RAcP with high affinity exhibiting an off-rate (wherein koff is measured by Biacore®) for human IL-1RAcP in the range $3.06 \times 10^{-5}$ s$^{-1}$ to $2.01 \times 10^{-5}$ s$^{-1}$. In some embodiments, the preferred IL-1RAcP antibodies of the disclosure bind to human IL-1RAcP exhibiting a $K_D$ value less than $25 \times 10^{-12}$ M.

In some embodiments the IL-1RAcP antibodies or antigen binding fragments thereof of the disclosure may exhibit an off-rate (koff) for human IL-1RAcP of less than $5 \times 10^{-5}$ s$^{-1}$, less than $4 \times 10^{-5}$ s$^{-1}$, less than $3 \times 10^{-5}$ s$^{-1}$ or less than $2.5 \times 10^{-5}$ s$^{-1}$, when tested as a mAb, for example when the affinity of a heavy chain variable domain paired with a light chain variable domain is tested in the context of an IgG1 molecule.

In some embodiments, the present disclosure refers to the antibodies or antigen binding fragments disclosed in in Table 1, wherein said antibodies or antigen binding fragments can bind monovalent to human IL-1RAcP with a $K_D$ value of about less than 50 pM, preferably less than about 30 pM, less than about 25 pM.

In some embodiments, the present disclosure refers to antibodies or antigen binding fragments specific for IL-1RAcP, wherein said antibodies or antigen binding fragments have a monovalent affinity to IL-1RAcP as stated above and wherein said antibodies or antigen binding fragments in a bivalent format have an affinity to IL-1RAcP with a dissociation rate constant (KD) which is at least 2-fold, 5-fold, 10-fold, 100-fold, 1000-fold, 10000-fold lower than the dissociation rate constant (KD) in a monovalent format.

In some embodiments the antibody inhibits signaling initiated by one or more of IL-1α, IL-1β, IL-33, IL-36α, IL-36β, and IL-36γ agonist binding to its cognate receptor by at least 90%, at least 91%, at least 92%, at least 93%, at least 94%, at least 95%, at least 96%, at least 97%, at least 98%, at least 99%, or about 100%; In embodiments the full inhibitory effect on the signaling is measured by a designated cell-based inhibitory assays; In an embodiment, the full inhibitory effect on the intracellular signaling is obtained at EC$_{80}$ of the cytokine binding to the designated receptor.

In some embodiments the antibodies have the following sequences:

TABLE 1

| Y024148 | SEQ ID NO: 1 | LCDR 1 | RASQSISSWLA |
|---|---|---|---|
| | SEQ ID NO: 2 | LCDR 2 | DASSLES |
| | SEQ ID NO: 3 | LCDR 3 | HQLLIYPHT |
| | SEQ ID NO: 4 | HCDR 1 | GSAVH |
| | SEQ ID NO: 5 | HCDR 2 | RILTYSSTTQYAESVKG |
| | SEQ ID NO: 6 | HCDR 3 | GSSEYPKFDI |
| | SEQ ID NO: 7 | VH | EVQLVESGGGLVQPGGSLRLSCAASGGTIGGSAVHWVRQAPG KGLVWVSRILTYSSTTQYAESVKGRFTISRDNAKNTLYLQMNS LRAEDTAVYYCARGSSEYPKFDIWGQGTLVTVSS |
| | SEQ ID NO: 8 | VL | DIQMTQSPSTLSASVGDRVTITCRASQSISSWLAWYQQKPGKAP KLLIYDASSLESGVPSRFSGSGSGTEFTLTISSLQPEDFATYYCH QLLIYPHTFGQGTKVEIKRT |
| | SEQ ID NO: 17 | HC | EVQLVESGGGLVQPGGSLRLSCAASGGTIGGSAVHWVRQAPG KGLVWVSRILTYSSTTQYAESVKGRFTISRDNAKNTLYLQMNS LRAEDTAVYYCARGSSEYPKFDIWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVDK RVEPKSCDKTHTCPPCPAPEAEGAPSVFLFPPKPKDTLMISRTPE VTCVVVDVSHEDPEVKFNWYVDGVEVHNAKTKPREEQYNST YRVVSVLTVLHQDWLNGKEYKCKVSNKALPSSIEKTISKAKGQ PREPQVYTLPPSREEMTKNQVSLTCLVKGFYPSDIAVEWESNG QPENNYKTTPPVLDSDGSFFLYSKLTVDKSRWQQGNVFSCSVM HEALHNHYTQKSLSLSPGK |

TABLE 1-continued

| | | | |
|---|---|---|---|
| | SEQ ID NO: 18 | LC | DIQMTQSPSTLSASVGDRVTITCRASQSISSWLAWYQQKPGKAP KLLIYDASSLESGVPSRFSGSGSGTEFTLTISSLQPEDFATYYCH QLLIYPHTFGQGTKVEIKRTVAAPSVFIFPPSDEQLKSGTASVVC LLNNFYPREAKVQWKVDNALQSGNSQESVTEQDSKDSTYSLSS TLTLSKADYEKHKVYAcEVTHQGLSSPVTKSFNRGEC |
| Y024149 | SEQ ID NO: 9 | LCDR 1 | RASQSISSWLA |
| | SEQ ID NO: 10 | LCDR 2 | DASSLES |
| | SEQ ID NO: 11 | LCDR 3 | HQLLIYPHT |
| | SEQ ID NO: 12 | HCDR 1 | GSAMH |
| | SEQ ID NO: 13 | HCDR 2 | RILTYGGIATYAESVKG |
| | SEQ ID NO: 14 | HCDR 3 | GSSEYPKFDI |
| | SEQ ID NO: 15 | VH | EVQLVESGGGLVQPGGSLRLSCAASGGTFGGSAMHWVRQAPG KGLVWVSRILTYGGIATYAESVKGRFTISRDNAKNTLYLQMNS LRAEDTAVYYCARGSSEYPKFDIWGQGTLVTVSS |
| | SEQ ID NO: 16 | VL | DIQMTQSPSTLSASVGDRVTITCRASQSISSWLAWYQQKPGKAP KLLIYDASSLESGVPSRFSGSGSGTEFTLTISSLQPEDFATYYCH QLLIYPHTFGQGTKVEIKRT |
| | SEQ ID NO: 19 | HC | EVQLVESGGGLVQPGGSLRLSCAASGGTFGGSAMHWVRQAPG KGLVWVSRILTYGGIATYAESVKGRFTISRDNAKNTLYLQMNS LRAEDTAVYYCARGSSEYPKFDIWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVDK RVEPKSCDKTHTCPPCPAPEAEGAPSVFLFPPKPKDTLMISRTPE VTCVVVDVSHEDPEVKFNWYVDGVEVHNAKTKPREEQYNST YRVVSVLTVLHQDWLNGKEYKCKVSNKALPSSIEKTISKAKGQ PREPQVYTLPPSREEMTKNQVSLTCLVKGFYPSDIAVEWESNG QPENNYKTTPPVLDSDGSFFLYSKLTVDKSRWQQGNVFSCSVM HEALHNHYTQKSLSLSPGK |
| | SEQ ID NO: 20 | LC | DIQMTQSPSTLSASVGDRVTITCRASQSISSWLAWYQQKPGKAP KLLIYDASSLESGVPSRFSGSGSGTEFTLTISSLQPEDFATYYCH QLLIYPHTFGQGTKVEIKRTVAAPSVFIFPPSDEQLKSGTASVVC LLNNFYPREAKVQWKVDNALQSGNSQESVTEQDSKDSTYSLSS TLTLSKADYEKHKVYAcEVTHQGLSSPVTKSFNRGEC |

Y024148

Figure 1C:
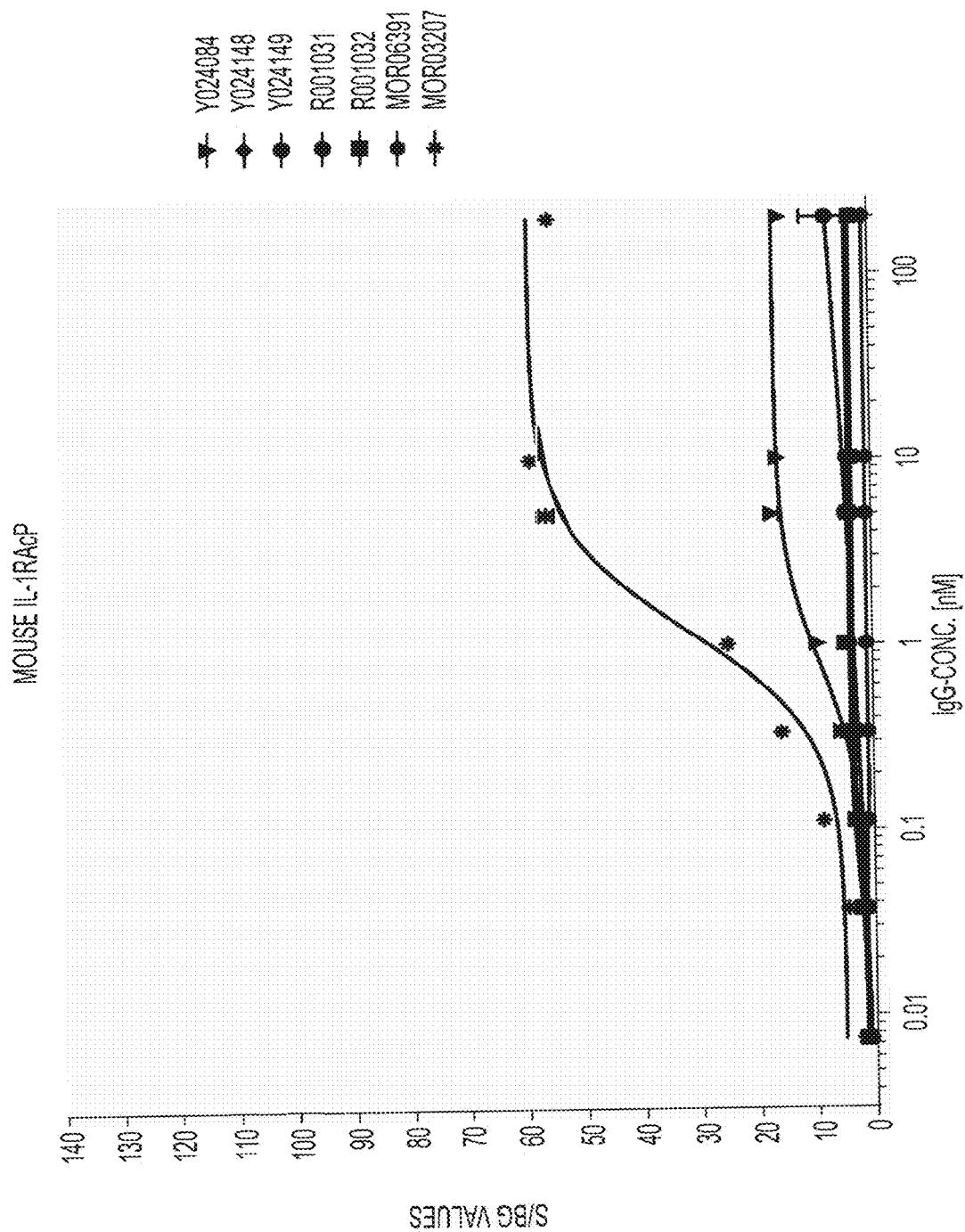
FIG. 1C: Various concentrations of the antibodies in the IgG1f_AEASS format were tested for binding to mouse (AG-12212) IL-1RAcP (IL-1RAP) were assessed in Fc-capture mode of the IgGs.
Figure 2A:
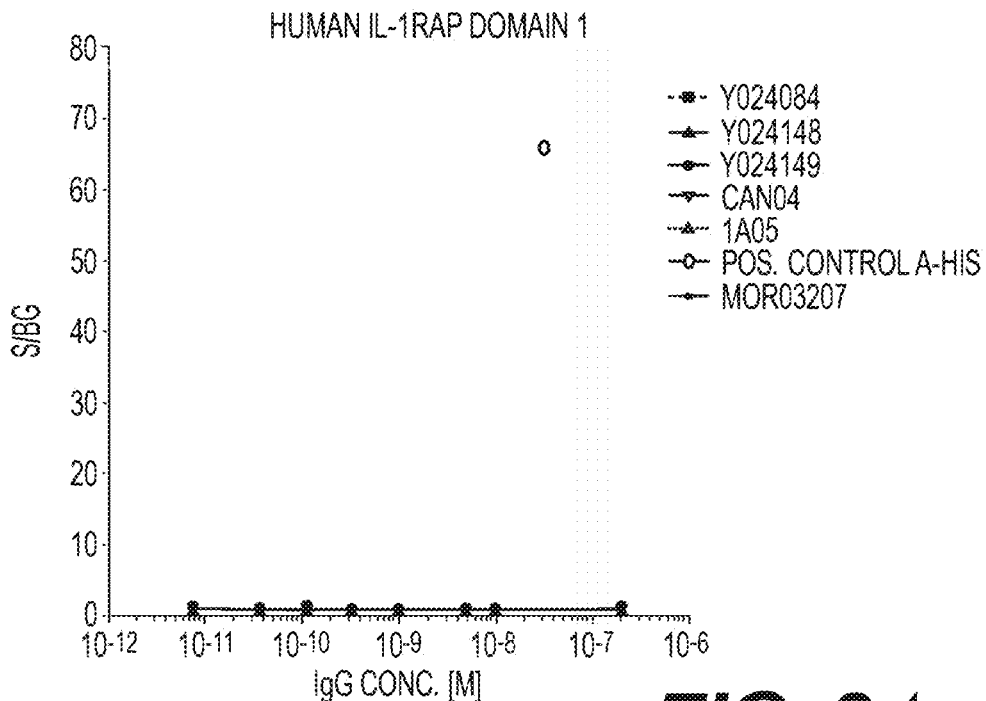
FIG. 2A: Various concentrations of the antibodies in the IgG1f_AEASS format were tested for binding to human IL1RAcP(IL-1RAP) domain 1 (AG-12335).
Figure 2B:
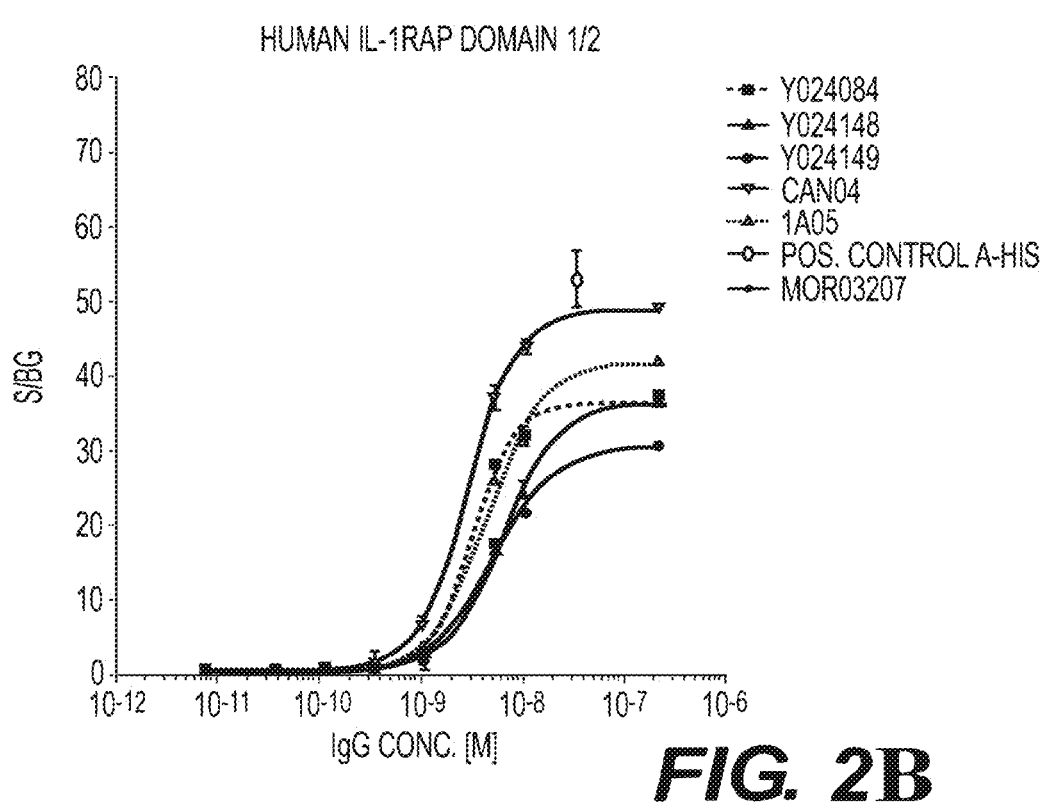
FIG. 2B: Various concentrations of the antibodies in the IgG1f_AEASS format were tested for binding to human IL1RAcP (IL-1RAP)domain 1/2 (AG-12337)
Figure 2C:
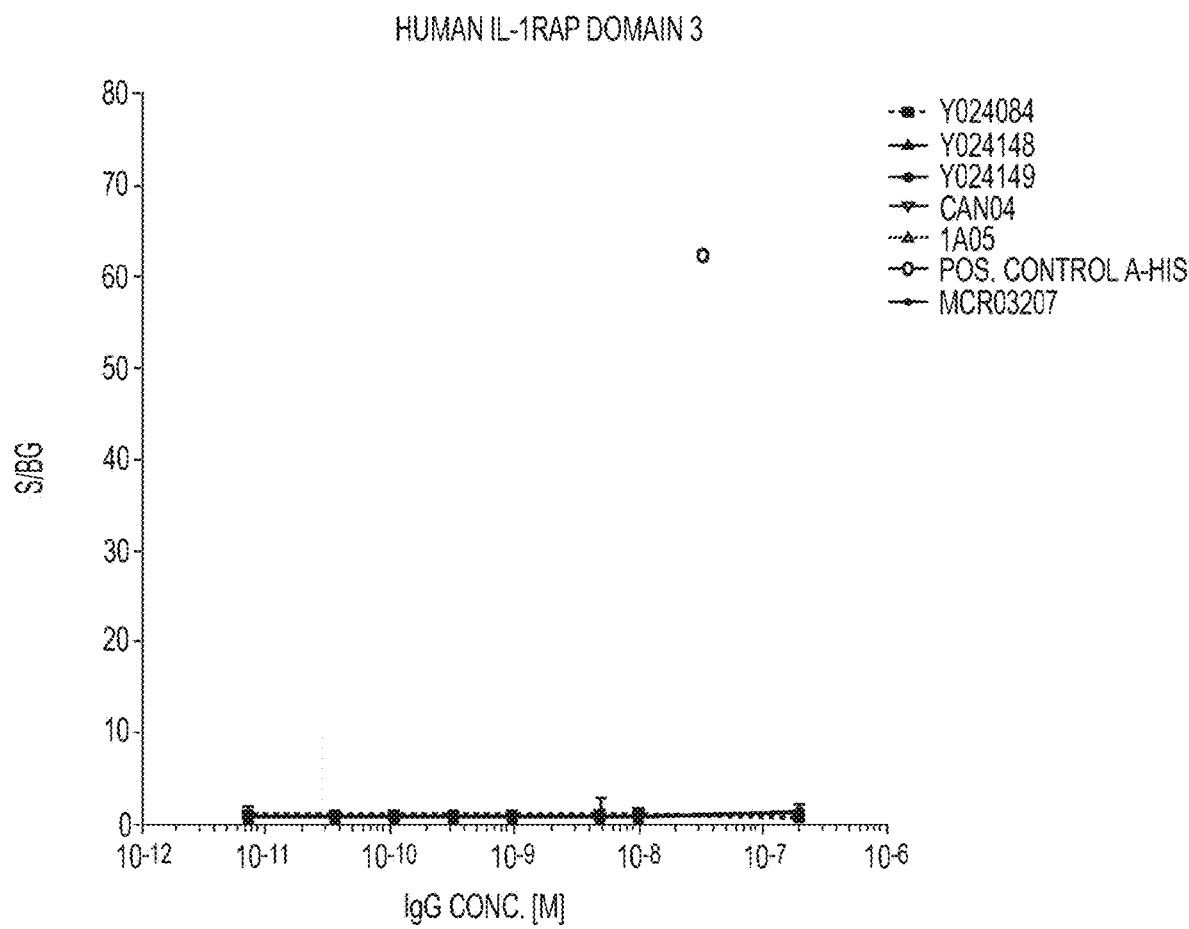
FIG. 2C: Various concentrations of the antibodies in the IgG1f_AEASS format were tested for binding to human IL1RAcP (IL-1RAP) domain 3 (AG-12127)
Figure 3:
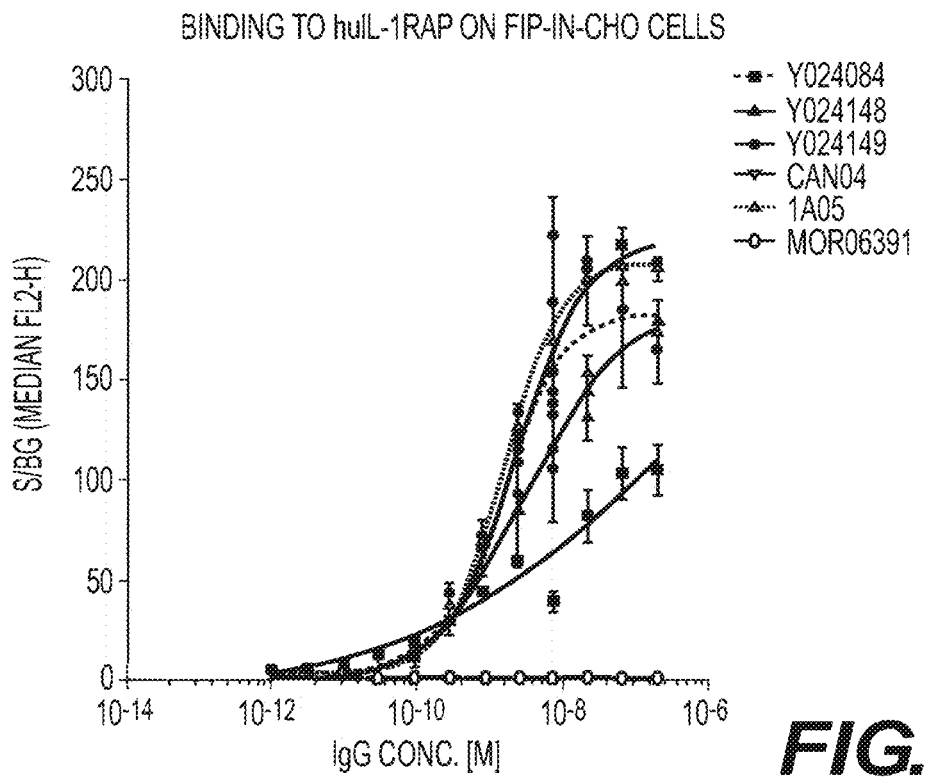
FIG. 3: FACS analysis of binding of antibodies in the IgG1f_AEASS format to human IL-1RAcP over-expressing CHO cells.
Figure 4:
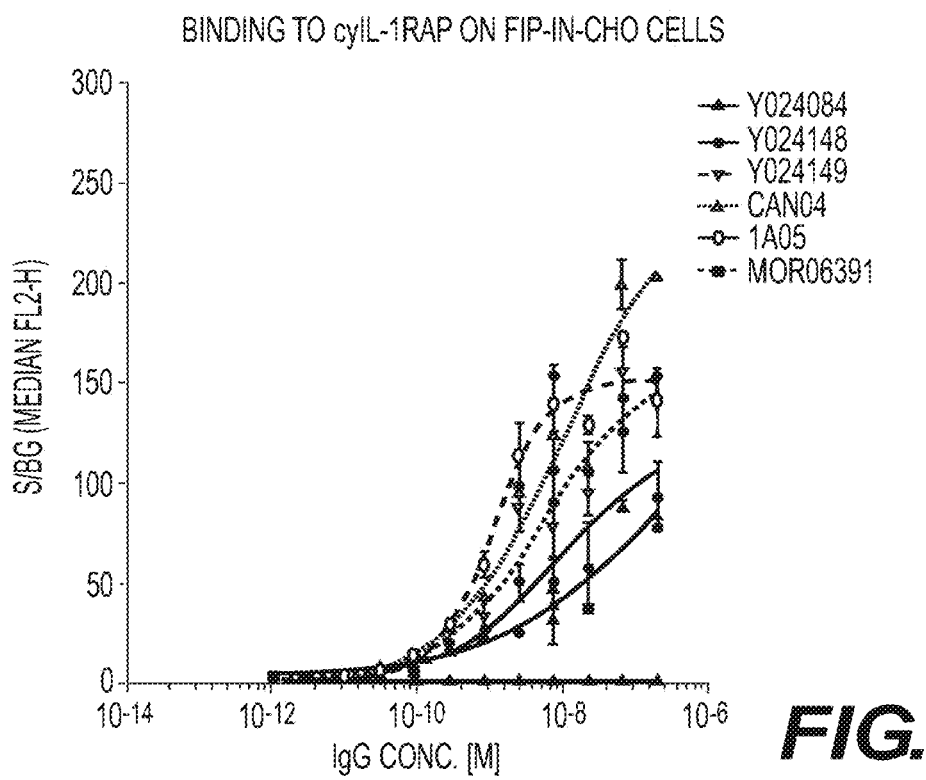
FIG. 4: FACS analysis of binding of antibodies in the IgG1f_AEASS format to cynomolgus IL-1RAcP over-expressing CHO cells.
Figure 5:
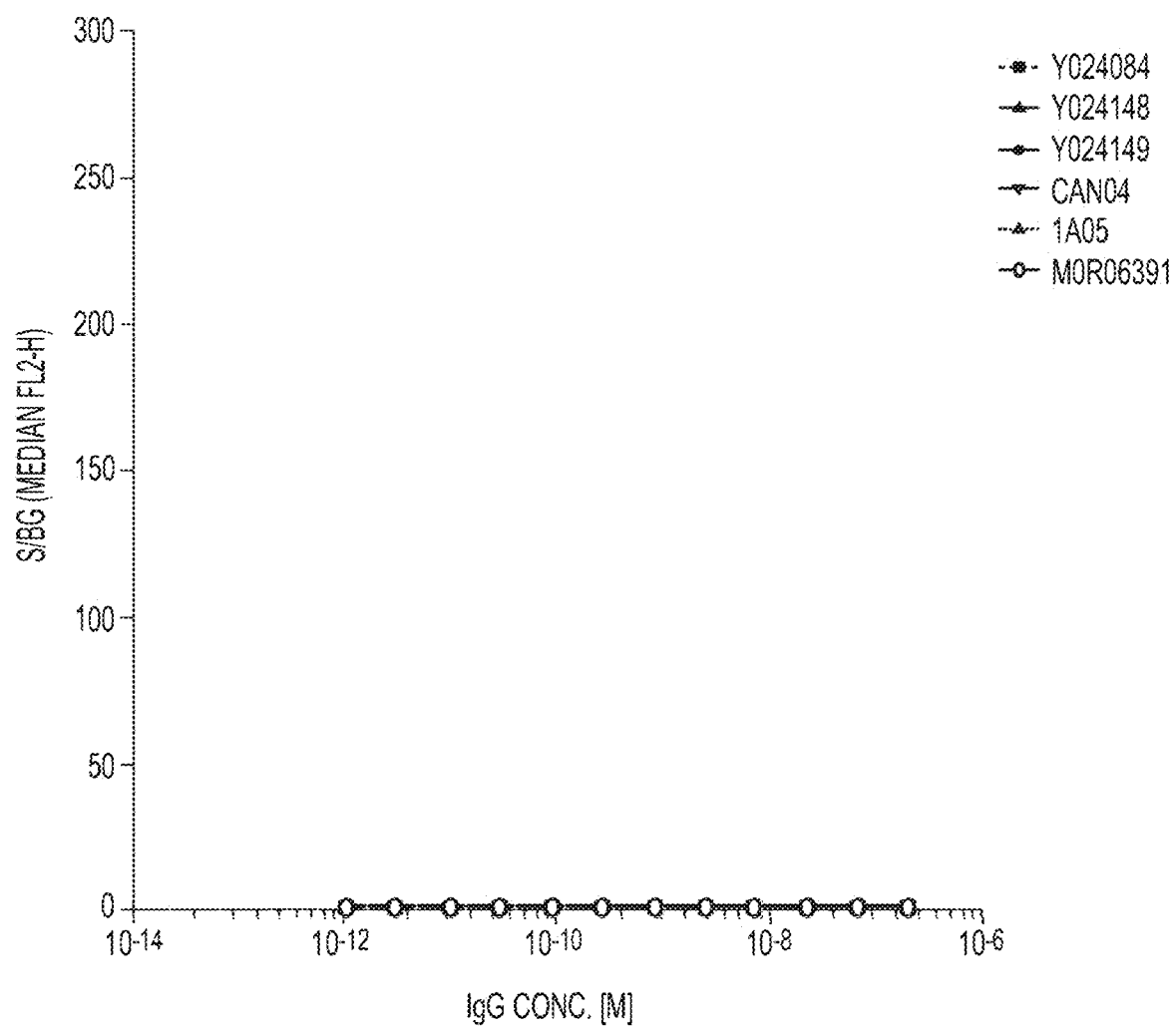
FIG. 5: As control, antibodies were also tested in titration on parental CHO cells not expressing human or cynomolgus IL-1RAcP.

Y024148 binds to domain 1/2 of human IL-1RAcP (FIG. 2B). Y024148 does not bind to domain 1 or 3 of human IL-1RAcP (FIGS. 2A and 2C). Y024148 does not bind to recombinant mouse or rat IL-1RAcP (FIG. 1C).

Y024148 binds to human IL-1RAcP with a $K_D$ of 2 pM as measured by solution equilibrium titration (Table 6-1). This $K_D$ value is approximately 5.5 and 10.5 times stronger than that demonstrated for the R001032 and R001031 reference antibodies, respectively, which have the variable domains of the prior art 1A05 and CAN04 antibodies, respectively. In addition, Y024148 binds to cyno IL-1RAcP with a $K_D$ of 1 pM as measured by solution equilibrium titration (SET; Table 6-2). This $K_D$ value is approximately 15 and 16 times stronger than that demonstrated for the R001032 and R001031 reference antibodies.

Y024148, in FabCys-AviHis format (disulphide-linked Fab with Avi and His tags), binds to human IL-1RAcP with a $K_D$ of 18 pM as measured by surface plasmon resonance at 25° C. (Table 5-1). This $K_D$ value is approximately 9-12 times stronger than that demonstrated for the CAN04 and 1A05 reference antibodies in FabCys-AviHis format. In addition, Y024148, in FabCys-AviHis format, binds to cynomolgus IL-1RAcP with a $K_D$ of 8 pM as measured by surface plasmon resonance at 25° C. (Table 5-2). This $K_D$ value is approximately 16-23 times stronger than that demonstrated for the CAN04 and 1A05 reference antibodies in FabCys-AviHis format.

Y024148 potently inhibits IL-1α of human dermal fibroblasts. An $IC_{50}$ value of 1.2 nM is reported in Table 2. In contrast, reference antibodies having the variable domains of the prior art CAN04, 1A05 and h11C5 antibodies exhibited $IC_{50}$ values of 3.6-24 nM.

Y024148 potently inhibits IL-1β stimulation of cynomolgus dermal fibroblasts. An $IC_{50}$ value of 0.043 nM is reported in Table 2. In contrast, reference antibodies having the variable domains of the prior art CAN04, 1A05 and h11C5 antibodies exhibited $IC_{50}$ values of 0.48-1 nM.

Y024148 also potently inhibits IL-36α, IL-36β and IL-36γ stimulation of human dermal fibroblasts. $IC_{50}$ values of 0.014 nM, 0.039 nM and 0.042 nM, respectively, are reported in Table 2. In addition, Y024148 potently inhibits IL-1β and IL-36β stimulation of human epidermal keratinocytes ($IC_{50}$ values of 35 nM and 0.2 nM in Table 2, respectively) and IL-1β and IL-33 stimulation of human peripheral blood mononuclear cells ($IC_{50}$ values of 1.2 nM and 0.72 nM in Table 2, respectively).

Y024148 binds to an epitope that does not overlap with the epitope bound by any of the prior art CAN03, CAN04 and h11C5 antibodies. While the Y024148 epitope potentially overlaps with the 1A05 epitope, the competition profile for the two antibodies is shown in the Examples to be distinct (e.g. 1A05 competes with CAN04, but Y024148 does not compete with CAN04).

Furthermore, Y024148 showed high monomer content (98.0%), demonstrating high stability of the antibody and high production yield in CHO cells (14.5 mg/ml), when purified by standard methods of antibody production.

In some embodiments, antibodies and antigen-binding fragments encompassed by the present disclosure may have similar functional properties can be expected to be associated with the antibodies defined below which share structural and binding characteristics with the Y024148 antibody.

In some embodiments the disclosure provides an anti-IL1RAcP antibody or antigen binding fragment thereof comprising complementarity determining regions (CDRs) with:
  i. a sequence that is at least 70%, at least 80% identical to SEQ ID NO: 4 for CDR1 of the heavy chain;
  ii. a sequence that is at least 70%, at least 80%, or at least 90% identical to SEQ ID NO: 5 for CDR2 of the heavy chain;
  iii. a sequence that is at least 70%, at least 80%, or at least 90% identical to SEQ ID NO: 6 for CDR3 of the heavy chain;
  iv. a sequence that is at least 70%, at least 80%, or at least 90% identical to SEQ ID NO: 1 for CDR1 of the light chain;
  v. a sequence that is at least 70% or at least 80% identical to SEQ ID NO: 2 for CDR2 of the light chain; and
  vi. a sequence that is at least 70% at least 80%, or at least 85% identical to SEQ ID NO: 3 for CDR3 of the light chain.

In some embodiments, the anti-IL1RAcP antibody or antigen binding fragment thereof comprises complementarity determining regions (CDRs) with:
  i. a sequence that is at least 80% identical to SEQ ID NO: 4 for CDR1 of the heavy chain;
  ii. a sequence that is at least 70% identical to SEQ ID NO: 5 for CDR2 of the heavy chain;
  iii. a sequence that is at least 90% identical to SEQ ID NO: 6 for CDR3 of the heavy chain;
  iv. a sequence that is at least 90% identical to SEQ ID NO: 1 for CDR1 of the light chain;
  v. a sequence that is at least 90% identical to SEQ ID NO: 2 for CDR2 of the light chain; and
  vi. a sequence that is at least 90% identical to SEQ ID NO: 3 for CDR3 of the light chain.

In some embodiments, the anti-IL1RAcP antibody or antigen binding fragment thereof comprises complementarity determining regions (CDRs) with:
  i. a sequence that is at least 90% identical to SEQ ID NO: 4 for CDR1 of the heavy chain;
  ii. a sequence that is at least 90% identical to SEQ ID NO: 5 for CDR2 of the heavy chain;
  iii. a sequence that is at least 90% identical to SEQ ID NO: 6 for CDR3 of the heavy chain;
  iv. a sequence that is at least 90% identical to SEQ ID NO: 1 for CDR1 of the light chain;
  v. a sequence that is at least 90% identical to SEQ ID NO: 2 for CDR2 of the light chain; and
  vi. a sequence that is at least 90% identical to SEQ ID NO: 3 for CDR3 of the light chain.

In some embodiments, the anti-IL1RAcP antibody or antigen binding fragment thereof comprises complementarity determining regions (CDRs) with:
  i. a sequence that is at least 90% identical to SEQ ID NO: 4 for CDR1 of the heavy chain;
  ii. a sequence that is at least 80% identical to SEQ ID NO: 5 for CDR2 of the heavy chain;
  iii. a sequence that is at least 70% identical to SEQ ID NO: 6 for CDR3 of the heavy chain;
  iv. a sequence that is at least 90% identical to SEQ ID NO: 1 for CDR1 of the light chain;
  v. a sequence that is at least 90% identical to SEQ ID NO: 2 for CDR2 of the light chain; and
  vi. a sequence that is at least 90% identical to SEQ ID NO: 3 for CDR3 of the light chain.

In some embodiments, the anti-IL1RAcP antibody or antigen binding fragment thereof comprises complementarity determining regions (CDRs) with:
  i. a sequence that is at least 80% identical to SEQ ID NO: 4 for CDR1 of the heavy chain;
  ii. a sequence that is at least 70% identical to SEQ ID NO: 5 for CDR2 of the heavy chain;
  iii. the amino acid sequence of SEQ ID NO: 6 for CDR3 of the heavy chain;
  iv. the amino acid sequence of SEQ ID NO: 1 for CDR1 of the light chain;
  v. the amino acid sequence of SEQ ID NO: 2 for CDR2 of the light chain; and
  vi. the amino acid sequence of SEQ ID NO: 3 for CDR3 of the light chain.

In some embodiments, the anti-IL1RAcP antibody or antigen binding fragment thereof comprises complementarity determining regions (CDRs) with the amino acid sequence of:
  i. GSAX$_1$H (SEQ ID NO: 73) for CDR1 of the heavy chain;
  ii. RILTYX$_2$X$_3$X$_4$X$_5$X$_6$YAESVKG (SEQ ID NO: 74) for CDR2 of the heavy chain;
  iii. the amino acid sequence of SEQ ID NO: 6 for CDR3 of the heavy chain;
  iv. the amino acid sequence of SEQ ID NO: 1 for CDR1 of the light chain;
  v. the amino acid sequence of SEQ ID NO: 2 for CDR2 of the light chain; and
  vi. the amino acid sequence of SEQ ID NO: 3 for CDR3 of the light chain, wherein each of $X_1$, $X_2$, $X_3$, $X_4$, $X_5$ and $X_6$ is any amino acid.

In some embodiments, the anti-IL1RAcP antibody or antigen binding fragment thereof comprises complementarity determining regions (CDRs) with the amino acid sequence of:
  i. GSAXiH (SEQ ID NO: 75) for CDR1 of the heavy chain;
  ii. RILTYX$_2$X$_3$X$_4$X$_5$X$_6$YAESVKG (SEQ ID NO: 76) for CDR2 of the heavy chain;
  iii. the amino acid sequence of SEQ ID NO: 6 for CDR3 of the heavy chain;
  iv. the amino acid sequence of SEQ ID NO: 1 for CDR1 of the light chain;
  v. the amino acid sequence of SEQ ID NO: 2 for CDR2 of the light chain; and
  vi. the amino acid sequence of SEQ ID NO: 3 for CDR3 of the light chain, wherein: (a) $X_1$ is V or M, (b) $X_2$ is S or G, (c) $X_3$ is S or G, (d) $X_4$ is T or I, (e) $X_5$ is T or A, or (f) $X_6$ is Q or T.

In some embodiments, the anti-IL1RAcP antibody or antigen binding fragment thereof comprises complementarity determining regions (CDRs) with the amino acid sequence of
  i. GSAXiH (SEQ ID NO: 75) for CDR1 of the heavy chain;
  ii. RILTYX$_2$X$_3$X$_4$X$_5$X$_6$YAESVKG (SEQ ID NO: 76) for CDR2 of the heavy chain;
  iii. the amino acid sequence of SEQ ID NO: 6 for CDR3 of the heavy chain;
  iv. the amino acid sequence of SEQ ID NO: 1 for CDR1 of the light chain;
  v. the amino acid sequence of SEQ ID NO: 2 for CDR2 of the light chain; and vi. the amino acid sequence of SEQ ID NO: 3 for CDR3 of the light chain, wherein: (a) $X_1$ is V or M, (b) $X_2$ is S or G, (c) $X_3$ is S or G, (d) $X_4$ is T or I, (e) $X_5$ is T or A, and (f) $X_6$ is Q or T.

In some embodiments, the anti-IL-1RAcP antibody or antigen binding fragment thereof comprises complementarity determining regions (CDRs) with the amino acid sequences of:
i. SEQ ID NO: 4 for CDR1 of the heavy chain;
ii. SEQ ID NO: 5 for CDR2 of the heavy chain;
iii. SEQ ID NO: 6 for CDR3 of the heavy chain;
iv. SEQ ID NO: 1 for CDR1 of the light chain;
v. SEQ ID NO: 2 for CDR2 of the light chain; and
vi. SEQ ID NO: 3 for CDR3 of the light chain.

In some embodiments, the anti-IL-1RAcP antibody or antigen binding fragment thereof binds to domain 2 of human IL-1RAcP.

In some embodiments, the anti-IL-1RAcP antibody or antigen binding fragment thereof binds to domain 2 of human IL-1RAcP, and does not bind to domain 1 or domain 3 of human IL-1RAcP.

In some embodiments, the anti-IL-1RAcP antibody or antigen binding fragment thereof binds to:
(a) domain 2 of human IL-1RAcP, and
(b) cynomolgus IL-1RAcP.

In some embodiments, the anti-IL-1RAcP antibody or antigen binding fragment thereof:
(a) does not bind to mouse IL-1RAcP, and
(b) does not bind to rat IL-1RAcP.

In some embodiments, the anti-IL-1RAcP antibody or antigen binding fragment thereof:
a) binds to:
b) domain 2 of human IL-1RAcP, and
c) cynomolgus IL-1RAcP; and
d) does not bind to mouse IL-1RAcP; and
e) does not bind to rat IL-1RAcP.

In some embodiments, the anti-IL-1RAcP antibody or antigen binding fragment thereof binds to human IL-1RAcP with a $K_D$ that is lower than the $K_D$ determined under the same assay conditions (such as surface plasmon resonance, e.g. at 25° C., or solution equilibration titration, e.g., at 25° C.) for each of:
(i) a first reference anti-IL-1RAcP antibody consisting of two heavy and two light chains,
wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36, or
(ii) a second reference anti-IL-1RAcP antibody consisting of two heavy and two light chains,
wherein each heavy chain of the second reference anti-IL-1RAcP antibody has the amino acid sequence of SEQ ID NO: 51 and wherein each light chain of the second reference anti-IL-1RAcP antibody has the amino acid sequence of SEQ ID NO: 52.

In some embodiments, the anti-IL-1RAcP antibody or antigen binding fragment thereof binds to cynomolgus IL-1RAcP with a $K_D$ that is lower than the $K_D$ determined under the same assay conditions (such as surface plasmon resonance, e.g. at 25° C., or solution equilibration titration, e.g., at 25° C.) for each of:
(i) a first reference anti-IL-1RAcP antibody consisting of two heavy and two light chains,
wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36, or
(ii) a second reference anti-IL-1RAcP antibody consisting of two heavy and two light chains,
wherein each heavy chain of the second reference anti-IL-1RAcP antibody has the amino acid sequence of SEQ ID NO: 51, and wherein each light chain of the second reference anti-IL-1RAcP antibody has the amino acid sequence of SEQ ID NO: 52.

In some embodiments, the anti-IL-1RAcP antibody or antigen binding fragment thereof binds to human IL-1RAcP with a $K_D$ of 5 pM or less (as determined using solution equilibrium titration, e.g., at 25° C.).

In some embodiments, the anti-IL-1RAcP antibody or antigen binding fragment thereof binds to human IL-1RAcP with a $K_D$ that is at least 3 times lower (e.g. at least 5 times lower) than the $K_D$ determined under the same assay conditions (such as using solution equilibrium titration, e.g., at 25° C.) for a reference anti-IL-1RAcP antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof binds to human IL-1RAcP with a $K_D$ that is at least 2 times lower (e.g. at least 4 times lower) than the $K_D$ determined under the same assay conditions (such as using solution equilibrium titration, e.g., at 25° C.) for a reference anti-IL-1RAcP antibody consisting of two heavy and two light chains,
wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof binds to cynomolgus IL-1RAcP with a $K_D$ of 1 pM or less (as determined using solution equilibrium titration, e.g., at 25° C.).

In some embodiments, the anti-IL-1RAcP antibody or antigen binding fragment thereof binds to cynomolgus IL-1RAcP with a $K_D$ that is at least 3 times lower (e.g. at least 5 times lower) than the $K_D$ determined under the same assay conditions (such as using solution equilibrium titration, e.g., at 25° C.) for a reference anti-IL-1RAcP antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof binds to cynomolgus IL-1RAcP with a $K_D$ that is at least 3 times lower (e.g. at least 5 times lower) than the $K_D$ determined under the same assay conditions (such as using solution equilibrium titration, e.g., at 25° C.) for a reference anti-IL-1RAcP antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof binds to human IL-1RAcP with a $K_D$ of 20 pM or less such as determined by surface plasmon resonance, e.g., at 25° C.

In some embodiments, the anti-IL-1RAcP antibody or antigen binding fragment thereof binds to human IL-1RAcP with a $K_D$ that is at least 5 times lower, optionally at least 10 times lower than the $K_D$ determined under the same assay conditions such as a surface plasmon resonance assay, e.g., at 25° C. for a reference anti-IL-1RAcP antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof binds to human IL-1RAcP with a $K_D$ that is at least 4 times lower, optionally at least 8 times lower than the $K_D$ determined under the same assay conditions such as a surface plasmon resonance assay, e.g., at 25° C., for a reference anti-IL-1RAcP antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof binds to cynomolgus IL-1RAcP with a $K_D$ of 10 pM or less as determined by surface plasmon resonance, e.g., at 25° C.

In some embodiments, the anti-IL-1RAcP antibody or antigen binding fragment thereof binds to cynomolgus IL-1RAcP with a $K_D$ that is lower than the $K_D$ determined under the same assay conditions such as surface plasmon resonance at 25° C., for each of:
 (i) a first reference anti-IL-1RAcP antibody consisting of two heavy and two light chains,
  wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36, and
 (ii) a second reference anti-IL-1RAcP antibody consisting of two heavy and two light chains, wherein each heavy chain of the second reference anti-IL-1RAcP antibody has the amino acid sequence of SEQ ID NO: 51, and wherein each light chain of the second reference anti-IL-1RAcP antibody has the amino acid sequence of SEQ ID NO: 52.

In some embodiments, the anti-IL-1RAcP antibody or antigen binding fragment thereof binds to cynomolgus IL-1RAcP with a $K_D$ that is at least 10 times lower, optionally at least 20 times lower, than the $K_D$ determined under the same assay conditions, such as a surface plasmon resonance assay, e.g., at 25° C., for a reference anti-IL-1RAcP antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof binds to cynomolgus IL-1RAcP with a $K_D$ that is at least 5 times lower, optionally at least 10 times lower, than the $K_D$ determined under the same assay conditions, such as a surface plasmon resonance assay, e.g., at 25° C., for a reference anti-IL-1RAcP antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof inhibits IL-1α-induced stimulation of human dermal fibroblasts more strongly, optionally with an $IC_{50}$ value that is at least two-fold lower, under the same in vitro assay conditions, than a reference antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof inhibits IL-1α-induced stimulation of human dermal fibroblasts more strongly, optionally with an $IC_{50}$ value that is at least three-fold lower, optionally an $IC_{50}$ value that is at least five-fold lower, under the same in vitro assay conditions, than a reference antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof inhibits IL-1α-induced stimulation of human dermal fibroblasts more strongly, optionally with an $IC_{50}$ value that is at least three-fold lower, or optionally with an $IC_{50}$ value that is at least five-fold lower, under the same in vitro assay conditions, than a reference antibody consisting of two heavy and two light chains, wherein each heavy chain of the reference anti-IL-1RAcP antibody has the amino acid sequence of SEQ ID NO: 31, and wherein each light chain of the reference anti-IL-1RAcP antibody has the amino acid sequence of SEQ ID NO: 32.

In some embodiments, the anti-IL-1RAcP antibody or antigen binding fragment thereof inhibits IL-1α-induced stimulation of human dermal fibroblasts more strongly, optionally with an $IC_{50}$ value that is at least two-fold lower, under the same in vitro assay conditions, than each of the following:
 (a) a first reference antibody consisting of two heavy and two light chains, wherein each heavy chain of the first reference anti-IL-1RAcP antibody has the amino acid sequence of SEQ ID NO: 51, and wherein each light chain of the first reference anti-IL-1RAcP antibody has the amino acid sequence of SEQ ID NO: 52;
 (b) a second reference antibody consisting of two heavy and two light chains, wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36; and
 (c) a third reference antibody consisting of two heavy and two light chains, wherein each heavy chain of the first reference anti-IL-1RAcP antibody has the amino acid sequence of SEQ ID NO: 31, and wherein each light chain of the first reference anti-IL-1RAcP antibody has the amino acid sequence of SEQ ID NO: 32.

In some embodiments, the anti-IL-1RAcP antibody or antigen binding fragment thereof inhibits IL-1α-induced stimulation of human dermal fibroblasts with an $IC_{50}$ value of less than 2.5 nM when measured in an assay comprising:

(i) suspending human dermal fibroblasts in a culture medium and seeding in a microtitre (384-well) plate in a volume of 30 μl,
(ii) adding the antibody or antigen binding fragment thereof to the cells two hours after plating,
(iii) incubating for 30 minutes,
(iv) adding IL-1α to the cells to a final concentration of 2 pM,
(v) incubating the plate for 24 hours at 37° C. in a humidified incubator,
(vi) obtaining a sample of the supernatant and quantifying IL-8 in a homogenous time resolved fluorescence assay.

In some embodiments, the anti-IL-1RAcP antibody or antigen binding fragment thereof inhibits IL-1β-induced stimulation of cynomolgus dermal fibroblasts more strongly, for example with an $IC_{50}$ value that is at least three-fold lower, optionally with an $IC_{50}$ value that is at least five-fold lower, under the same in vitro assay conditions, than a reference antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof inhibits IL-1β-induced stimulation of cynomolgus dermal fibroblasts more strongly, for example with an $IC_{50}$ value that is at least two-fold lower, under the same in vitro assay conditions, than a reference antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof inhibits IL-1β-induced stimulation of cynomolgus dermal fibroblasts more strongly, for example with an $IC_{50}$ value that is at least three-fold lower, optionally with an $IC_{50}$ value that is at least five-fold lower, under the same in vitro assay conditions, than a reference antibody consisting of two heavy and two light chains, wherein each heavy chain of the reference anti-IL-1RAcP antibody has the amino acid sequence of SEQ ID NO: 31, and wherein each light chain of the reference anti-IL-1RAcP antibody has the amino acid sequence of SEQ ID NO: 32.

In some embodiments, the anti-IL-1RAcP antibody or antigen binding fragment thereof inhibits IL-1β-induced stimulation of cynomolgus dermal fibroblasts more strongly, for example with an $IC_{50}$ value that is at least two-fold lower, under the same in vitro assay conditions, than each of the following:
(a) a first reference antibody consisting of two heavy and two light chains, wherein each heavy chain of the first reference anti-IL-1RAcP antibody has the amino acid sequence of SEQ ID NO: 51, and wherein each light chain of the first reference anti-IL-1RAcP antibody has the amino acid sequence of SEQ ID NO: 52;
(b) a second reference antibody consisting of two heavy and two light chains, wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36; and
(c) a third reference antibody consisting of two heavy and two light chains, wherein each heavy chain of the first reference anti-IL-1RAcP antibody has the amino acid sequence of SEQ ID NO: 31, and wherein each light chain of the first reference anti-IL-1RAcP antibody has the amino acid sequence of SEQ ID NO: 32.

In some embodiments, the anti-IL-1RAcP antibody or antigen binding fragment thereof binds to the same epitope as a reference anti-IL-1RAcP antibody, wherein the reference anti-IL-1RAcP antibody consists of two heavy and two light chains, wherein each heavy chain of the reference anti-IL-1RAcP antibody has the amino acid sequence of SEQ ID NO: 17, and wherein each light chain of the reference anti-IL-1RAcP antibody has the amino acid sequence of SEQ ID NO: 18.

In some embodiments, inhibition of IL-1β-induced stimulation of cynomolgus dermal fibroblasts is determined by measuring the concentration of IL-8 in the culture medium.

In some embodiments, the anti-IL-1RAcP antibody or antigen binding fragment thereof inhibits IL-1β-induced stimulation of cynomolgus dermal fibroblasts with an $IC_{50}$ value of less than 0.10 nM when measured in an assay comprising:
(i) suspending cynomolgus dermal fibroblasts in a culture medium and seeding 3500 cells/well in a microtitre (collagen coated 384-well) plate,
(ii) adding the antibody or antigen binding fragment thereof to the cells (two hours after plating),
(iii) incubating for 30 minutes,
(iv) adding cynomolgus IL-1β to the cells to a final concentration of 1 pM,
(v) incubating the plate for 24 hours at 37° C. in a humidified incubator,
(vi) obtaining a sample of the supernatant and quantifying IL-8 in a homogenous time resolved fluorescence assay.

In some embodiments, the anti-IL-1RAcP antibody or antigen binding fragment thereof competes for binding to human IL-1RAcP with a reference anti-IL-1RAcP with a disulphide-linked Fab (FabCys), wherein each VH domain of the reference anti-IL-1RAcP FabCys has the sequence of SEQ ID NO: 7, and wherein each VL domain of the reference anti-IL-1RAcP FabCys has the sequence of SEQ ID NO: 8.

In some embodiments, competition is assessed using an ELISA-based competition assay (e.g., at 25° C.). In some embodiments, the ELISA-based competition assay comprises using a reference antibody that is coated on a plate and a preformed complex of human IL-1RAcP and an anti-IL-1RAcP antibody or antigen binding fragment thereof. In some embodiments, the preformed complex of human IL-1RAcP and the anti-IL-1RAcP antibody or antigen binding fragment thereof is tagged with a moiety for detection, e.g., a biotin tag.

In some embodiments, the anti-IL-1RAcP antibody or antigen binding fragment thereof competes for binding to human IL-1RAcP with a first reference anti-IL-1RAcP disulphide-linked Fab (FabCys) and does not compete for binding to human IL-1RAcP with a second reference anti-IL-1RAcP FabCys, wherein each VH domain of the first reference anti-IL-1RAcP FabCys has the sequence of SEQ ID NO: 7, and wherein each VL domain of the first reference anti-IL-1RAcP FabCys has the sequence of SEQ ID NO: 8, and wherein each VH domain of the second reference anti-IL-1RAcP FabCys has the sequence of SEQ ID NO: 53, and wherein each VL domain of the second reference anti-IL-1RAcP FabCys has the sequence of SEQ ID NO: 54.

In some embodiments, the anti-IL-1RAcP antibody or antigen binding fragment thereof competes for binding to human IL-1RAcP with a first reference anti-IL-1RAcP disulphide-linked Fab (FabCys) and does not compete for binding to human IL-1RAcP with any of a second, third and fourth reference anti-IL-1RAcP FabCys, wherein each VH domain of the first reference anti-IL-1RAcP FabCys has the sequence of SEQ ID NO: 7, and wherein each VL domain of the first reference anti-IL-1RAcP FabCys has the sequence of SEQ ID NO: 8, wherein each VH domain of the second reference anti-IL-1RAcP FabCys has the sequence of SEQ ID NO: 53, and wherein each VL domain of the second reference anti-IL-1RAcP FabCys has the sequence of SEQ ID NO: 54, wherein each VH domain of the third reference anti-IL-1RAcP FabCys has the sequence of SEQ ID NO: 33, and wherein each VL domain of the second reference anti-IL-1RAcP FabCys has the sequence of SEQ ID NO: 34, and wherein each VH domain of the fourth reference anti-IL-1RAcP FabCys has the sequence of SEQ ID NO: 49, and wherein each VL domain of the second reference anti-IL-1RAcP FabCys has the sequence of SEQ ID NO: 50.

In some embodiments of the present disclosure, competition is assessed using an ELISA-based competition assay (e.g., at 25° C.). In some embodiments, the ELISA-based competition assay comprises using a reference antibody that is coated on a plate and a preformed complex of human IL-1RAcP and an anti-IL-1RAcP antibody or antigen binding fragment. In some embodiments, the preformed complex of human IL-1RAcP and the anti-IL-1RAcP antibody or antigen binding fragment thereof is tagged with a moiety for detection, e.g., a biotin tag.

In some embodiments, the present disclosure provides an anti-IL-1RAcP antibody or antigen binding fragment thereof comprising complementarity determining regions (CDRs) with the amino acid sequences of:
 i. SEQ ID NO: 4 for CDR1 of the heavy chain;
 ii. SEQ ID NO: 5 for CDR2 of the heavy chain;
 iii. SEQ ID NO: 6 for CDR3 of the heavy chain;
 iv. SEQ ID NO: 1 for CDR1 of the light chain;
 v. SEQ ID NO: 2 for CDR2 of the light chain; and
 vi. SEQ ID NO: 3 for CDR3 of the light chain.

In some embodiments, the present disclosure provides an anti-IL-1RAcP antibody or antigen binding fragment thereof comprising a heavy chain variable region of the amino acid sequence of SEQ ID NO: 7.

In some embodiments, the present disclosure provides an anti-IL-1RAcP antibody or antigen binding fragment thereof comprising a light chain variable region of the amino acid sequence of SEQ ID NO: 8.

In some embodiments, the present disclosure provides an anti-IL-1RAcP antibody or antigen binding fragment thereof comprising: (i) a heavy chain variable region of the amino acid sequence of SEQ ID NO: 7, and (ii) a light chain variable region of the amino acid sequence of SEQ ID NO: 8.

In some embodiments, the present disclosure provides an anti-IL-1RAcP antibody comprising a heavy chain of the amino acid sequence of SEQ ID NO: 17.

In some embodiments the present disclosure provides an anti-IL-1RAcP antibody comprising a light chain of the amino acid sequence of SEQ ID NO: 18.

In some embodiments, the present disclosure provides an anti-IL-1RAcP antibody comprising a heavy chain of the amino acid sequence of SEQ ID NO: 17, and a light chain of the amino acid sequence of SEQ ID NO: 18.

In some embodiments, the present disclosure provides an anti-IL-1RAcP antibody comprising two heavy and two light chains, wherein each heavy chain comprises a heavy chain variable region of the amino acid sequence of SEQ ID NO: 7, and wherein each light chain comprises a light chain variable region of the amino acid sequence of SEQ ID NO: 8.

In some embodiments, the present disclosure provides an anti-IL-1RAcP antibody consisting of two heavy and two light chains, wherein each heavy chain has the amino acid sequence of SEQ ID NO: 17, and wherein each light chain has the amino acid sequence of SEQ ID NO: 18.

Y024149

Y024149 binds to domain 1/2 of human IL-1RAcP ((FIG. 2B). Y024149 does not bind to domain 1 or 3 of human IL-1RAcP (FIGS. 2A and 2C). Y024149 does not bind to recombinant mouse or rat IL-1RAcP (FIG. 1C).

Y024149 binds to human IL-1RAcP with a $K_D$ of 3 pM as measured by solution equilibrium titration (Table 6-1). This $K_D$ value is approximately 3.5 and 7 times stronger than that demonstrated for the R001032 and R001031 reference antibodies, respectively, which have the variable domains of the prior art 1A05 and CAN04 antibodies, respectively. In addition, Y024149 binds to cynomolgus IL-1RAcP with a $K_D$ of 1 pM as measured by solution equilibrium titration (SET; Table 6-2). This $K_D$ value is approximately 15 and 16 times stronger than that demonstrated for the R001032 and R001031 reference antibodies. Y024149, in FabCys-AviHis format (disulphide-linked Fab with Avi and His tags), binds to human IL-1RAcP with a $K_D$ of 25 pM as measured by surface plasmon resonance at 25° C. (Table 5-1). This $K_D$ value is approximately 6.5-9 times stronger than that demonstrated for the CAN04 and 1A05 reference antibodies in FabCys-AviHis format. In addition, Y024149, in FabCys-AviHis format, binds to cynomolgus IL-1RAcP with a $K_D$ of 6 pM as measured by surface plasmon resonance at 25° C. (Table 5-2). This $K_D$ value is approximately 21-30 times stronger than that demonstrated for the CAN04 and 1A05 reference antibodies in FabCys-AviHis format.

Figure 6:
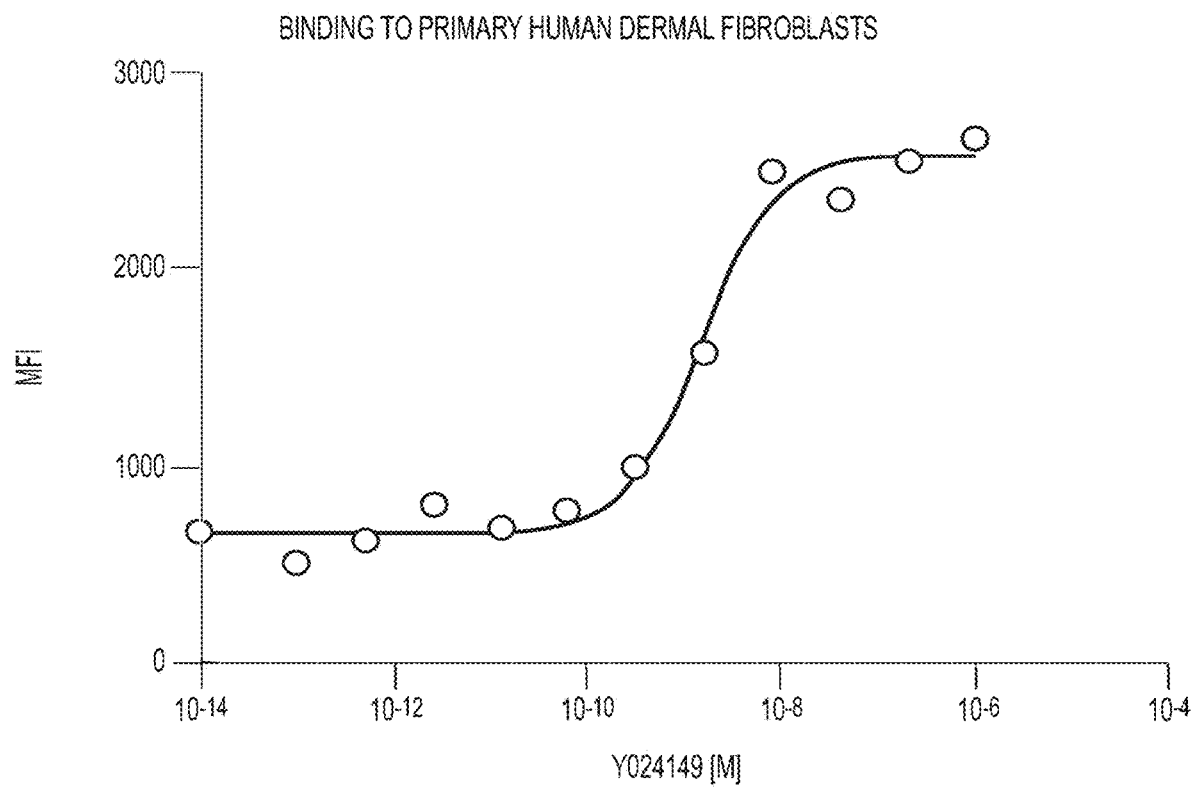
FIG. 6: Y024149 was tested for binding to primary human dermal fibroblast expressing endogenous IL-1RAcP, by FACS. EC50 value of binding reported in table.
Figure 7A:
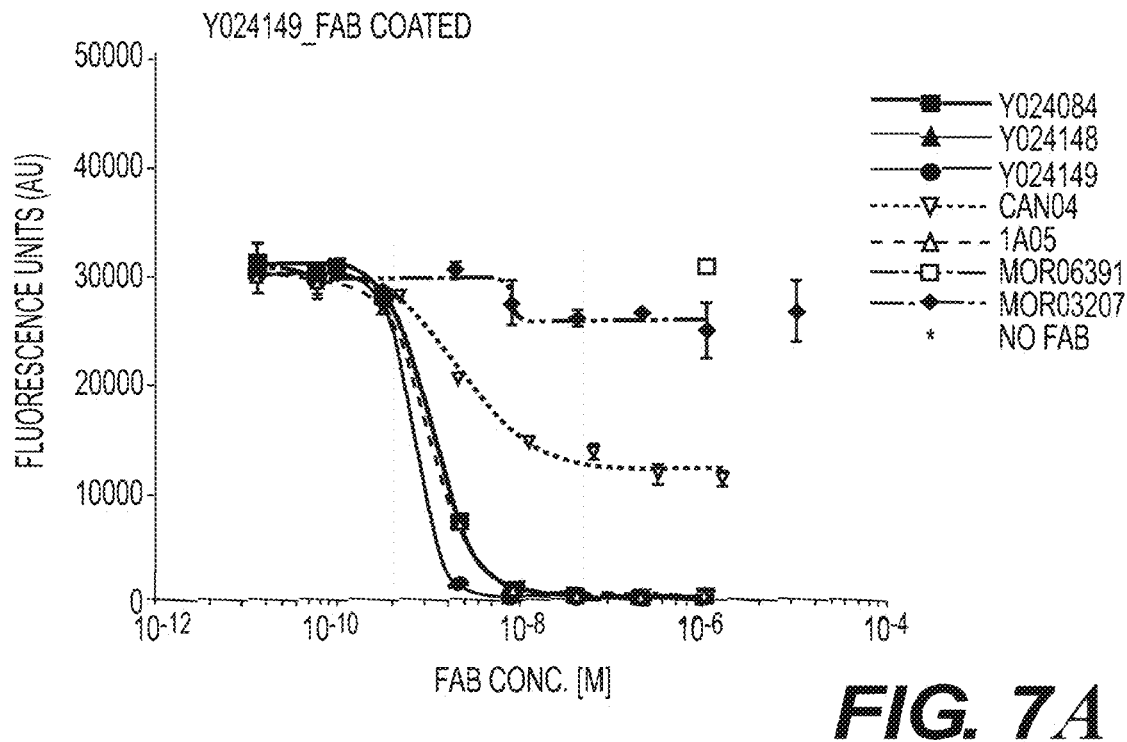
FIG. 7A: Antibody Y024084 in FabCys-AviHis format coated on the surface, and subsequent binding of reference antibodies.
Figure 7B:
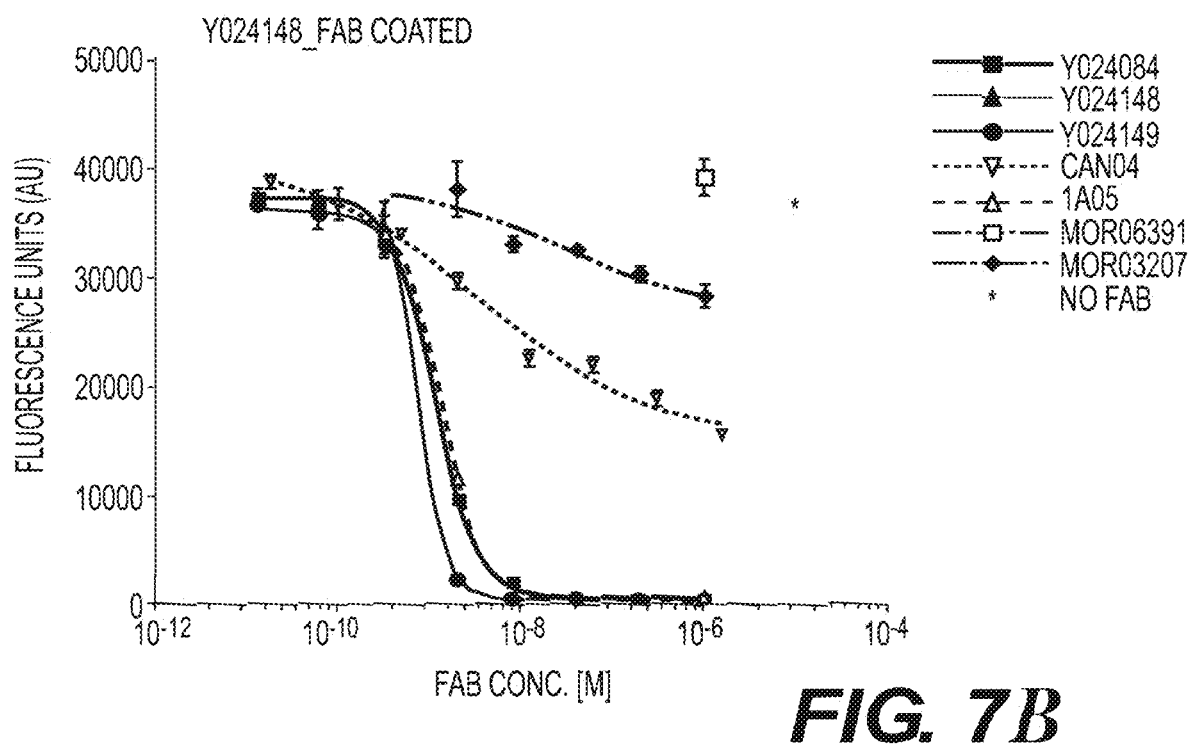
FIG. 7B: Antibody Y024148 in FabCys-AviHis format coated on the surface, and subsequent binding of reference antibodies.
Figure 7C:
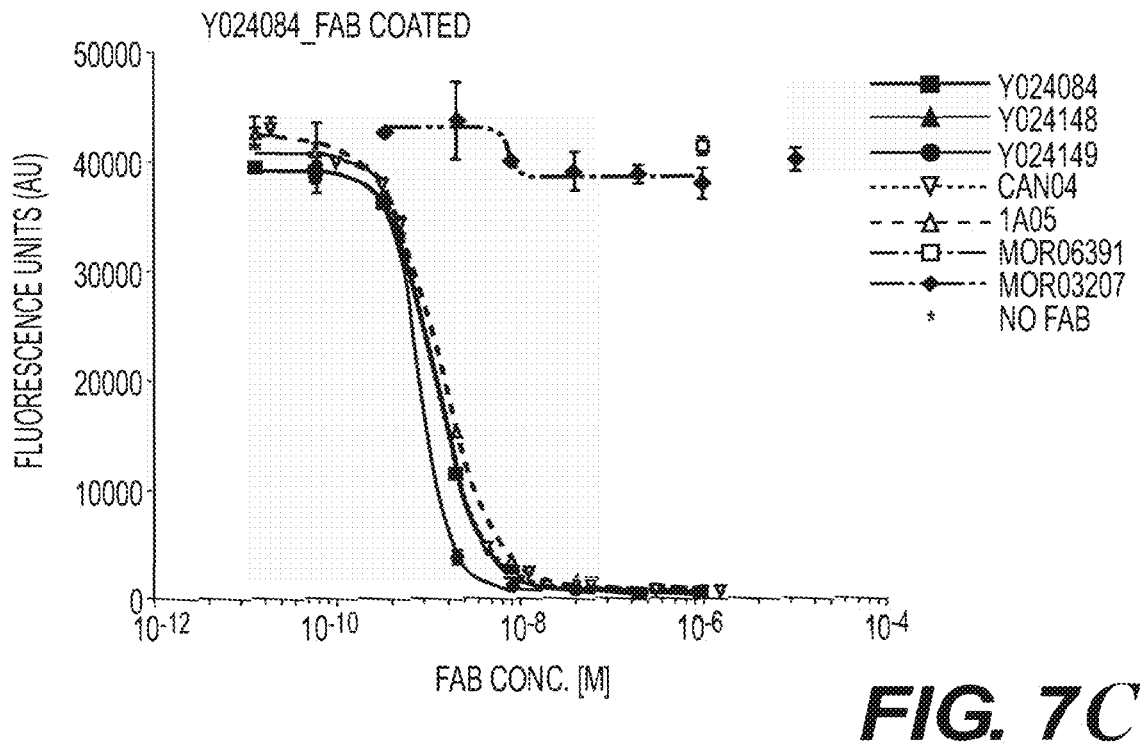
FIG. 7C: Antibody Y024149 in FabCys-AviHis format coated on the surface, and subsequent binding of reference antibodies.
Figure 7D:
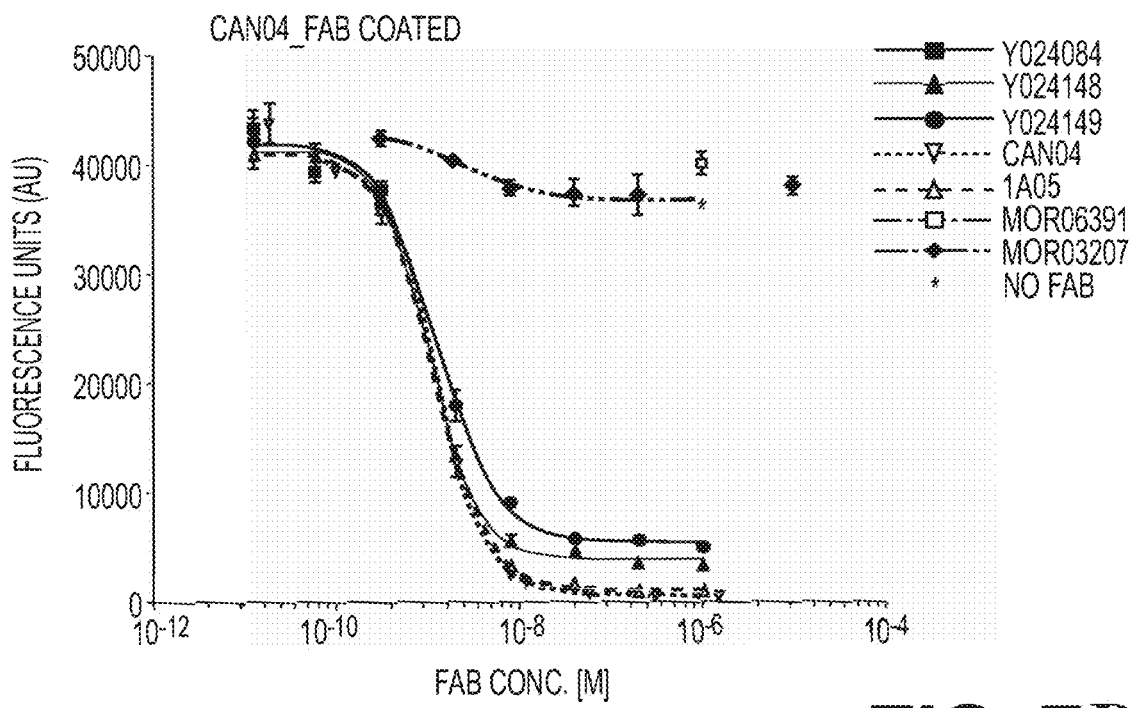
FIG. 7D: Antibody of prior art CAN04 in FabCys-AviHis format coated on the surface, and subsequent binding of reference antibodies.
Figure 7E:
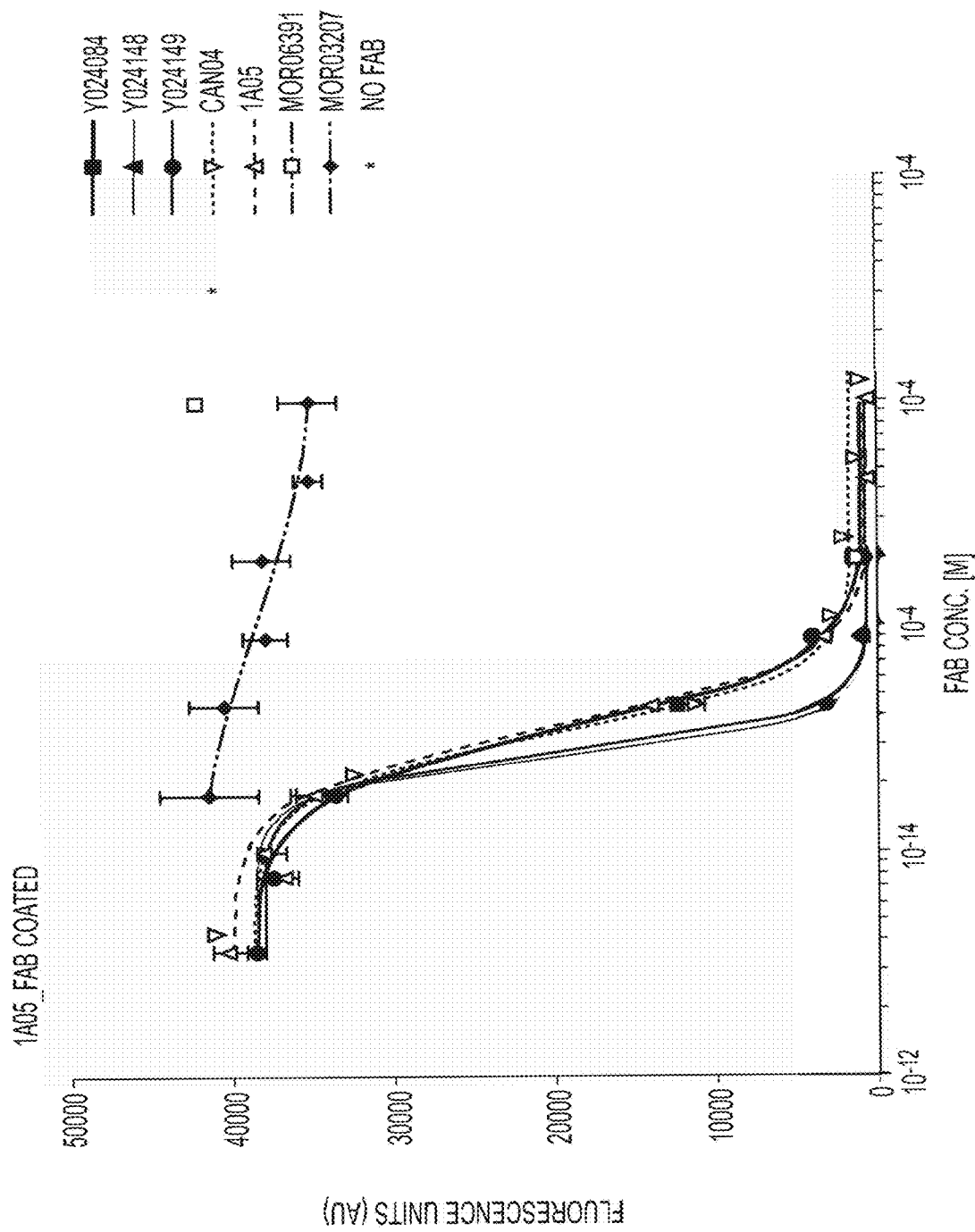
FIG. 7E: Antibody of prior art 1A05 in FabCys-AviHis format coated on the surface, and subsequent binding of reference antibodies.
Figure 8A:
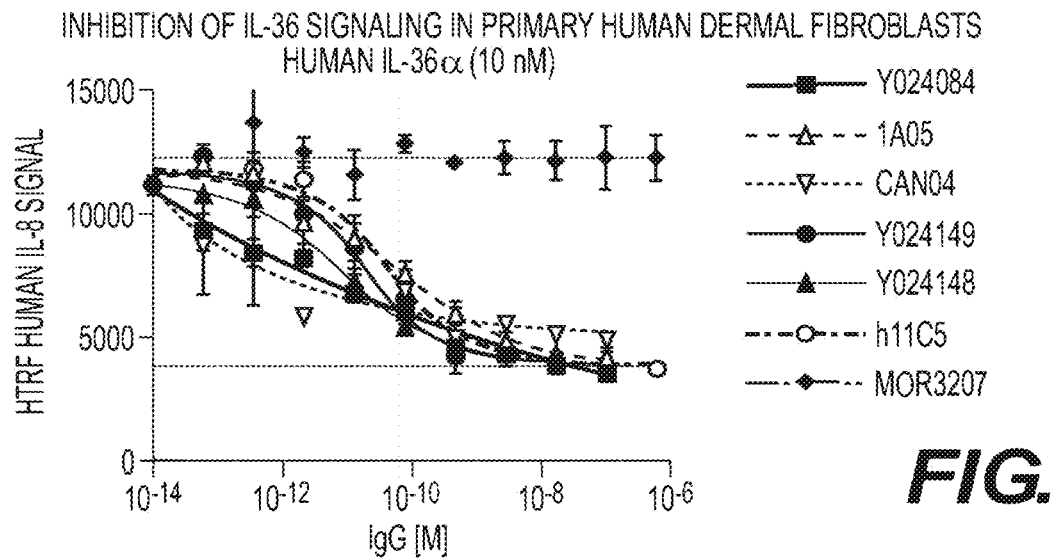
FIG. 8A: Inhibition of signalling by anti-IL1RAcP mAbs in primary human dermal fibroblasts stimulated with 10 nM IL-36α.
Figure 8B:
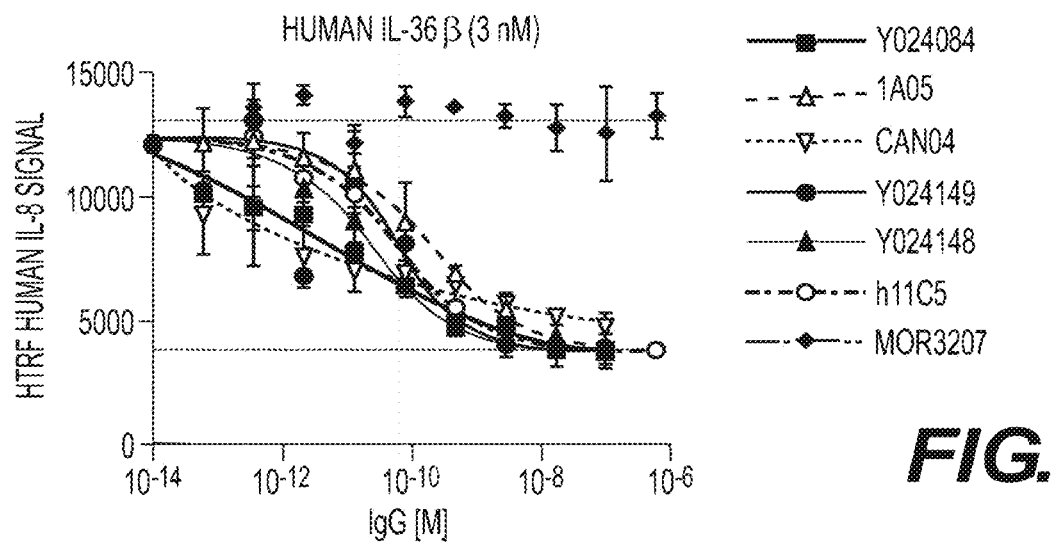
FIG. 8B: Inhibition of signalling by anti-IL1RAcP mAbs in primary human dermal fibroblasts stimulated with 3 nM IL-36b.
Figure 8C:
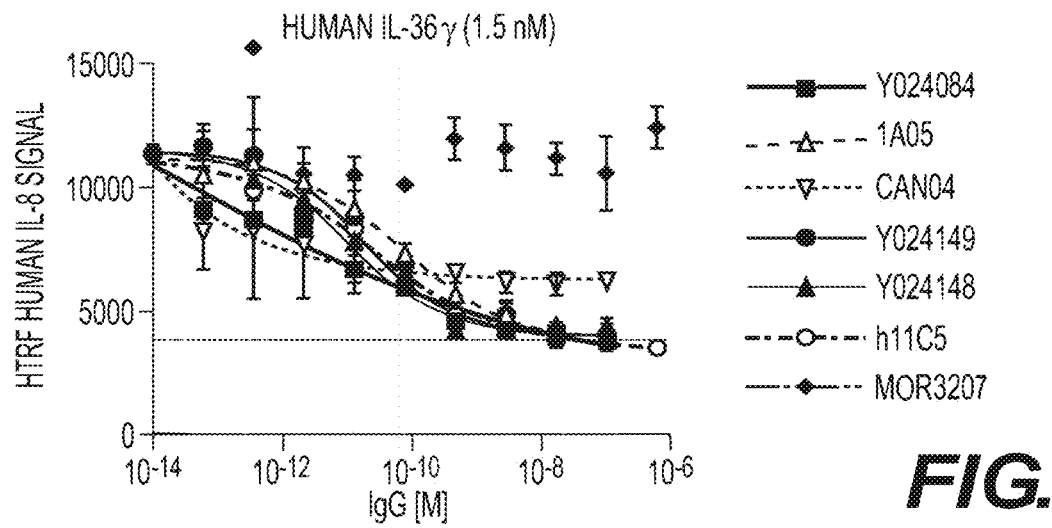
FIG. 8C: Inhibition of signalling by anti-IL1RAcP mAbs in primary human dermal fibroblasts stimulated with 1.5 nM IL-36g.
Figure 8D:
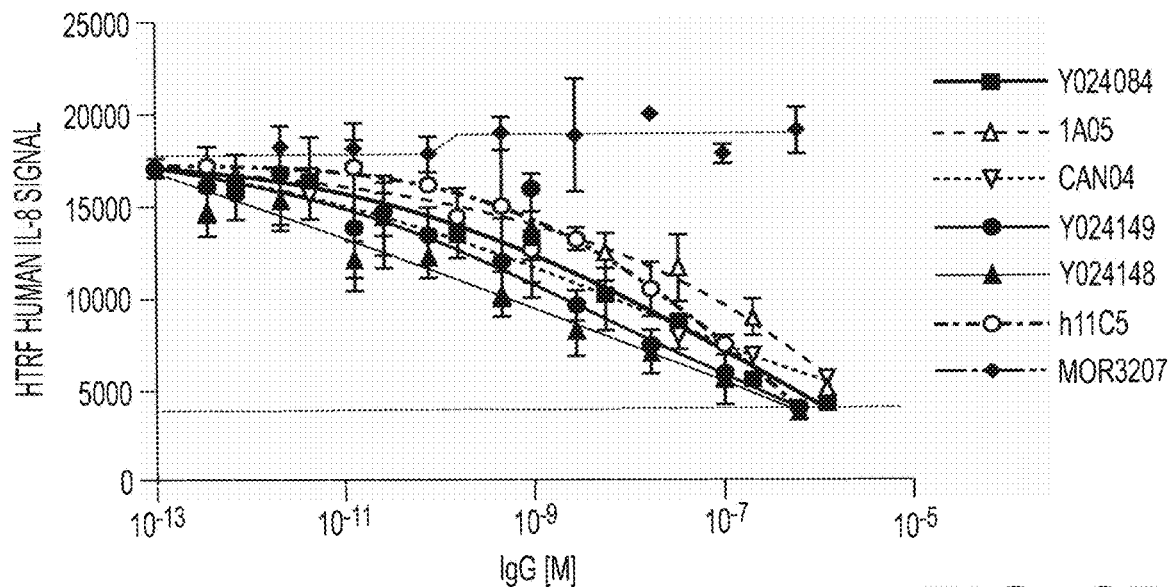
Figure 8E:
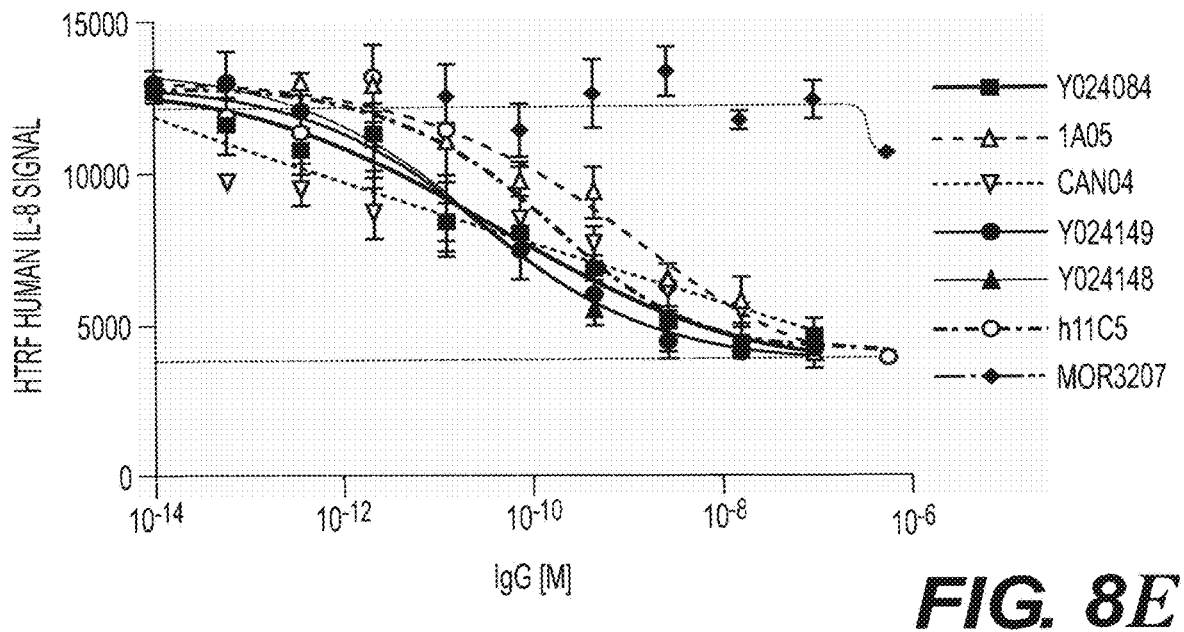
FIG. 8E: Inhibition of signalling by anti-IL1RAcP mAbs in primary cynomolgus dermal fibroblast stimulated with 1 pM IL-1β.

Y024149 binds to primary human dermal fibroblasts with an $EC_{50}$ of $1.477 \times 10^{-9}$ M (FIG. 6).

Y024149 potently inhibits stimulation by IL-1α in human dermal fibroblasts. An $IC_{50}$ value of 1.1 nM is reported in Table 2. In contrast, reference antibodies having the variable domains of the prior art CAN04, 1A05 and h11C5 antibodies exhibited $IC_{50}$ values of 3.6-24 nM.

Y024149 potently inhibits stimulation by IL-1β in cynomolgus dermal fibroblasts. An $IC_{50}$ value of 0.032 nM is reported in Table 2. In contrast, reference antibodies having the variable domains of the prior art CAN04, 1A05 and h11C5 antibodies exhibited $IC_{50}$ values of 0.48-1 nM.

Y024149 also potently inhibits stimulation by IL-36α, IL-36β and IL-36γ in human dermal fibroblasts. $IC_{50}$ values of 0.039 nM, 0.06 nM and 0.026 nM, respectively, are reported in Table 2. In addition, Y024149 potently inhibits IL-1β and IL-36β stimulation of human epidermal keratinocytes ($IC_{50}$ values of 31 nM and 0.094 nM in Table 2, respectively) and IL-1β and IL-33 stimulation of human peripheral blood mononuclear cells ($IC_{50}$ values of 1.7 nM and 0.2 nM, respectively).

Y024149 is capable of fully inhibiting IL-1β-induced IL-6 release by cynomolgus whole blood, with an $IC_{50}$ value of approximately 70 nM (see Example 13).

Y024149 binds to an epitope that does not overlap with the epitope bound by any of the prior art CAN03, CAN04 and h11C5 antibodies. While the Y024149 epitope potentially overlaps with the 1A05 epitope, the competition profile for the two antibodies is shown in the Examples to be distinct (e.g. 1A05 competes with CAN04, but Y024149 does not compete with CAN04).

Furthermore, Y024149 showed high monomer content (97.5%) and high production yield in CHO cells (11.1 mg/ml).

Similar functional properties can be expected to be associated with the antibodies defined below which share structural and binding characteristics with the Y024149 antibody.

In some embodiments, the disclosure provides an anti-IL1RAcP antibody or antigen binding fragment thereof comprising complementarity determining regions (CDRs) with:
 i. a sequence that is at least 70%, at least 80% identical to SEQ ID NO: 12 for CDR1 of the heavy chain;
 ii. a sequence that is at least 70%, at least 80% or at least 90% identical to SEQ ID NO: 13 for CDR2 of the heavy chain;
 iii. a sequence that is at least 70%, at least 80% or at least 90% identical to SEQ ID NO: 14 for CDR3 of the heavy chain;
 iv. a sequence that is at least 70%, at least 80% or at least 90% identical to SEQ ID NO: 9 for CDR1 of the light chain;
 v. a sequence that is at least 70% or at least 80% identical to SEQ ID NO: 10 for CDR2 of the light chain; and
 vi. a sequence that is at least 70% or at least 80% identical to SEQ ID NO: 11 for CDR3 of the light chain.

In some embodiments, the disclosure provides the anti-IL1RAcP antibody or antigen binding fragment thereof comprising complementarity determining regions (CDRs) with:
 i. a sequence that is at least 80% identical to SEQ ID NO: 12 for CDR1 of the heavy chain;
 ii. a sequence that is at least 70% identical to SEQ ID NO: 13 for CDR2 of the heavy chain;
 iii. a sequence that is at least 90% identical to SEQ ID NO: 14 for CDR3 of the heavy chain;
 iv. a sequence that is at least 90% identical to SEQ ID NO: 9 for CDR1 of the light chain;
 v. a sequence that is at least 90% identical to SEQ ID NO: 10 for CDR2 of the light chain; and
 vi. a sequence that is at least 90% identical to SEQ ID NO: 11 for CDR3 of the light chain.

In some embodiments, the disclosure provides the anti-IL1RAcP antibody or antigen binding fragment thereof comprising complementarity determining regions (CDRs) with:
 i. a sequence that is at least 90% identical to SEQ ID NO: 12 for CDR1 of the heavy chain;
 ii. a sequence that is at least 90% identical to SEQ ID NO: 13 for CDR2 of the heavy chain;
 iii. a sequence that is at least 90% identical to SEQ ID NO: 14 for CDR3 of the heavy chain;
 iv. a sequence that is at least 90% identical to SEQ ID NO: 9 for CDR1 of the light chain;
 v. a sequence that is at least 90% identical to SEQ ID NO: 10 for CDR2 of the light chain; and
 vi. a sequence that is at least 90% identical to SEQ ID NO: 11 for CDR3 of the light chain.

In one aspect, the present disclosure provides the anti-IL1RAcP antibody or antigen binding fragment thereof comprising complementarity determining regions (CDRs) with:
 i. a sequence that is at least 90% identical to SEQ ID NO: 12 for CDR1 of the heavy chain;
 ii. a sequence that is at least 80% identical to SEQ ID NO: 13 for CDR2 of the heavy chain;
 iii. a sequence that is at least 70% identical to SEQ ID NO: 14 for CDR3 of the heavy chain;
 iv. a sequence that is at least 90% identical to SEQ ID NO: 9 for CDR1 of the light chain;
 v. a sequence that is at least 90% identical to SEQ ID NO: 10 for CDR2 of the light chain; and
 vi. a sequence that is at least 90% identical to SEQ ID NO: 11 for CDR3 of the light chain.

In one aspect, the present disclosure provides the anti-IL1RAcP antibody or antigen binding fragment thereof comprising complementarity determining regions (CDRs) with:
 i. a sequence that is at least 80% identical to SEQ ID NO: 12 for CDR1 of the heavy chain;
 ii. a sequence that is at least 70% identical to SEQ ID NO: 13 for CDR2 of the heavy chain;
 iii. the amino acid sequence of SEQ ID NO: 14 for CDR3 of the heavy chain;
 iv. the amino acid sequence of SEQ ID NO: 9 for CDR1 of the light chain;
 v. the amino acid sequence of SEQ ID NO: 10 for CDR2 of the light chain; and
 vi. the amino acid sequence of SEQ ID NO: 11 for CDR3 of the light chain.

In one aspect, the present disclosure provides, the anti-IL1RAcP antibody or antigen binding fragment thereof comprising complementarity determining regions (CDRs) with the amino acid sequence of:
 i. GSAXiH (SEQ ID NO: 73) for CDR1 of the heavy chain;
 ii. RILTYX$_2$X$_3$X$_4$X$_5$X$_6$YAESVKG (SEQ ID NO: 74) for CDR2 of the heavy chain;
 iii. the amino acid sequence of SEQ ID NO: 14 for CDR3 of the heavy chain;
 iv. the amino acid sequence of SEQ ID NO: 9 for CDR1 of the light chain;
 v. the amino acid sequence of SEQ ID NO: 10 for CDR2 of the light chain; and
 vi. the amino acid sequence of SEQ ID NO: 11 for CDR3 of the light chain, wherein each of $X_1$, $X_2$, $X_3$, $X_4$, $X_5$ and $X_6$ is any amino acid.

In one aspect, the present disclosure provides the anti-IL1RAcP antibody or antigen binding fragment thereof comprising complementarity determining regions (CDRs) with the amino acid sequence of:
 i. GSAXiH (SEQ ID NO: 75) for CDR1 of the heavy chain;
 ii. RILTYX$_2$X$_3$X$_4$X$_5$X$_6$YAESVKG (SEQ ID NO: 76) for CDR2 of the heavy chain;
 iii. the amino acid sequence of SEQ ID NO: 14 for CDR3 of the heavy chain;
 iv. the amino acid sequence of SEQ ID NO: 9 for CDR1 of the light chain;
 v. the amino acid sequence of SEQ ID NO: 10 for CDR2 of the light chain; and
 vi. the amino acid sequence of SEQ ID NO: 11 for CDR3 of the light chain,
  wherein: (a) $X_1$ is V or M, (b) $X_2$ is S or G, (c) $X_3$ is S or G, (d) $X_4$ is T or I, (e) $X_5$ is T or A, or (f) $X_6$ is Q or T.

In one aspect, the present disclosure provides, the anti-IL1RAcP antibody or antigen binding fragment thereof comprising complementarity determining regions (CDRs) with the amino acid sequence of:
 i. GSAXiH (SEQ ID NO: 75) for CDR1 of the heavy chain;

ii. RILTYX$_2$X$_3$X$_4$X$_5$X$_6$YAESVKG (SEQ ID NO: 76) for CDR2 of the heavy chain;
iii. the amino acid sequence of SEQ ID NO: 14 for CDR3 of the heavy chain;
iv. the amino acid sequence of SEQ ID NO: 9 for CDR1 of the light chain;
v. the amino acid sequence of SEQ ID NO: 10 for CDR2 of the light chain; and
vi. the amino acid sequence of SEQ ID NO: 11 for CDR3 of the light chain, wherein: (a) X$_1$ is V or M, (b) X$_2$ is S or G, (c) X$_3$ is S or G, (d) X$_4$ is T or I, (e) X$_5$ is T or A, and (f) X$_6$ is Q or T.

In one aspect, the present disclosure provides, the anti-IL-1RAcP antibody or antigen binding fragment thereof comprising complementarity determining regions (CDRs) with the amino acid sequences of
i. SEQ ID NO: 12 for CDR1 of the heavy chain;
ii. SEQ ID NO: 13 for CDR2 of the heavy chain;
iii. SEQ ID NO: 14 for CDR3 of the heavy chain;
iv. SEQ ID NO: 9 for CDR1 of the light chain;
v. SEQ ID NO: 10 for CDR2 of the light chain; and
vi. SEQ ID NO: 11 for CDR3 of the light chain.

In some embodiments, the anti-IL-1RAcP antibody or antigen binding fragment thereof binds to domain 2 of human IL-1RAcP.

In some embodiments, the anti-IL-1RAcP antibody or antigen binding fragment thereof binds to domain 2 of human IL-1RAcP, and does not bind to domain 1 or domain 3 of human IL-1RAcP.

In some embodiments, the anti-IL-1RAcP antibody or antigen binding fragment thereof binds to: domain 2 of human IL-1RAcP, and cynomolgus IL-1RAcP.

In one aspect, the present disclosure provides the anti-IL-1RAcP antibody or antigen binding fragment thereof does not bind to mouse IL-1RAcP, and does not bind to rat IL-1RAcP.

In some embodiments, the anti-IL-1RAcP antibody or antigen binding fragment thereof binds to domain 2 of human IL-1RAcP, and cynomolgus IL-1RAcP; and
    does not bind to mouse IL-1RAcP; and does not bind to rat IL-1RAcP.

In some embodiments, the anti-IL-1RAcP antibody or antigen binding fragment thereof binds to human IL-1RAcP with a K$_D$ that is lower than the K$_D$ determined under the same assay conditions such as surface plasmon resonance at 25° C., or solution equilibration titration, e.g., at 25° C. for each of:
(i) a first reference anti-IL-1RAcP antibody consisting of two heavy and two light chains,
    wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36, and
(ii) a second reference anti-IL-1RAcP antibody consisting of two heavy and two light chains,
    wherein each heavy chain of the second reference anti-IL-1RAcP antibody has the amino acid sequence of SEQ ID NO: 51, and wherein each light chain of the second reference anti-IL-1RAcP antibody has the amino acid sequence of SEQ ID NO: 52.

In some embodiments, the anti-IL-1RAcP antibody or antigen binding fragment thereof binds to cynomolgus IL-1RAcP with a K$_D$ that is lower than the K$_D$ determined under the same assay conditions such as surface plasmon resonance at 25° C., or solution equilibration titration at 25° C., for each of:
(i) a first reference anti-IL-1RAcP antibody consisting of two heavy and two light chains, wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36, and
(ii) a second reference anti-IL-1RAcP antibody consisting of two heavy and two light chains, wherein each heavy chain of the second reference anti-IL-1RAcP antibody has the amino acid sequence of SEQ ID NO: 51, and wherein each light chain of the second reference anti-IL-1RAcP antibody has the amino acid sequence of SEQ ID NO: 52.

In some embodiments, the anti-IL-1RAcP antibody or antigen binding fragment thereof binds to human IL-1RAcP with a K$_D$ of 3 pM or less as determined using solution equilibrium titration, e.g., at 25° C.

In some embodiments, the anti-IL-1RAcP antibody or antigen binding fragment thereof binds to human IL-1RAcP with a K$_D$ that is at least 3 times lower, optionally at least 5 times lower, than the K$_D$ determined under the same assay conditions, such as using solution equilibrium titration, e.g., at 25° C., for a reference anti-IL-1RAcP antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof binds to human IL-1RAcP with a K$_D$ that is at least 2 times lower, optionally at least 4 times lower, than the K$_D$ determined under the same assay conditions, such as using solution equilibrium titration, e.g., at 25° C., for a reference anti-IL-1RAcP antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof binds to cynomolgus IL-1RAcP with a K$_D$ of 1 pM or less, as determined using solution equilibrium titration, e.g., at 25° C.

In some embodiments, the anti-IL-1RAcP antibody or antigen binding fragment thereof binds to cynomolgus IL-1RAcP with a K$_D$ that is at least 3 times lower, optionally at least 5 times lower, than the K$_D$ determined under the same assay conditions, such as using solution equilibrium titration, e.g., at 25° C., for a reference anti-IL-1RAcP antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof binds to cynomolgus IL-1RAcP with a K$_D$ that is at least 3 times lower, optionally at least 5 times lower, than the K$_D$ determined under the same assay conditions, such as using solution equilibrium titration, e.g., at 25° C., for a reference anti-IL-1RAcP antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof binds to human IL-1RAcP with a $K_D$ of 25 pM or less as determined by surface plasmon resonance, e.g., at 25° C.

In some embodiments, the anti-IL-1RAcP antibody or antigen binding fragment thereof binds to human IL-1RAcP with a $K_D$ that is at least 5 times lower, optionally at least 8 times lower, than the $K_D$ determined under the same assay conditions, such as a surface plasmon resonance assay, e.g., at 25° C., for a reference anti-IL-1RAcP antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof binds to human IL-1RAcP with a $K_D$ that is at least 4 times lower, optionally at least 6 times lower, than the $K_D$ determined under the same assay conditions, such as a surface plasmon resonance assay, e.g., at 25° C., for a reference anti-IL-1RAcP antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof binds to cynomolgus IL-1RAcP with a $K_D$ of 10 pM or less as determined by surface plasmon resonance, e.g., at 25° C.

In some embodiments, the anti-IL-1RAcP antibody or antigen binding fragment thereof binds to cynomolgus IL-1RAcP with a $K_D$ that is lower than the $K_D$ determined under the same assay conditions, such as surface plasmon resonance at 25° C., for each of
  (i) a first reference anti-IL-1RAcP antibody consisting of two heavy and two light chains,
    wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36, and
  (ii) a second reference anti-IL-1RAcP antibody consisting of two heavy and two light chains,
    wherein each heavy chain of the second reference anti-IL-1RAcP antibody has the amino acid sequence of SEQ ID NO: 51, and wherein each light chain of the second reference anti-IL-1RAcP antibody has the amino acid sequence of SEQ ID NO: 52.

In one aspect, the present disclosure provides, the anti-IL-1RAcP antibody or antigen binding fragment thereof binds to cynomolgus IL-1RAcP with a $K_D$ that is at least 10 times lower (e.g. at least 20 times lower) than the $K_D$ determined under the same assay conditions (such as a surface plasmon resonance assay, e.g., at 25° C.) for a reference anti-IL-1RAcP antibody consisting of two heavy and two light chains,
  wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof binds to cynomolgus IL-1RAcP with a $K_D$ that is at least 10 times lower (e.g. at least 15 times lower) than the $K_D$ determined under the same assay conditions (such as a surface plasmon resonance assay, e.g., at 25° C.) for a reference anti-IL-1RAcP antibody consisting of two heavy and two light chains,
  wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof inhibits IL-1α-induced stimulation of human dermal fibroblasts more strongly (e.g. with an $IC_{50}$ value that is at least two-fold lower), under the same in vitro assay conditions, than a reference antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof inhibits IL-1α-induced stimulation of human dermal fibroblasts more strongly, such as with an $IC_{50}$ value that is at least three-fold lower, optionally with an $IC_{50}$ value that is at least five-fold lower, under the same in vitro assay conditions, than a reference antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof inhibits IL-1α-induced stimulation of human dermal fibroblasts more strongly, such as with an $IC_{50}$ value that is at least three-fold lower, optionally an $IC_{50}$ value that is at least five-fold lower, under the same in vitro assay conditions, than a reference antibody consisting of two heavy and two light chains, wherein each heavy chain of the reference anti-IL-1RAcP antibody has the amino acid sequence of SEQ ID NO: 31, and wherein each light chain of the reference anti-IL-1RAcP antibody has the amino acid sequence of SEQ ID NO: 32.

In one aspect, the present disclosure provides, the anti-IL-1RAcP antibody or antigen binding fragment thereof inhibits IL-1α-induced stimulation of human dermal fibroblasts more strongly such as with an $IC_{50}$ value that is at least two-fold lower, under the same in vitro assay conditions, than each of the following:
  (a) a first reference antibody consisting of two heavy and two light chains, wherein each heavy chain of the first reference anti-IL-1RAcP antibody has the amino acid sequence of SEQ ID NO: 51, and wherein each light chain of the first reference anti-IL-1RAcP antibody has the amino acid sequence of SEQ ID NO: 52;
  (b) a second reference antibody consisting of two heavy and two light chains, wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36; and
  (c) a third reference antibody consisting of two heavy and two light chains, wherein each heavy chain of the first reference anti-IL-1RAcP antibody has the amino acid sequence of SEQ ID NO: 31, and wherein each light chain of the first reference anti-IL-1RAcP antibody has the amino acid sequence of SEQ ID NO: 32.

In some embodiments, inhibition of IL-1α-induced stimulation of human dermal fibroblasts is determined by measuring the concentration of IL-8 in the culture medium.

In some embodiments, the anti-IL-1RAcP antibody or antigen binding fragment thereof inhibits IL-1α-induced stimulation of human dermal fibroblasts with an $IC_{50}$ value of less than 2 nM when measured in an assay comprising:
   (i) suspending human dermal fibroblasts in a culture medium and seeding in a microtitre (384-well) plate in a volume of 30 µl,
   (ii) adding the antibody or antigen binding fragment thereof to the cells two hours after plating,
   (iii) incubating for 30 minutes,
   (iv) adding IL-1α to the cells to a final concentration of 2 pM,
   (v) incubating the plate for 24 hours at 37° C. in a humidified incubator,
   (vi) obtaining a sample of the supernatant and quantifying IL-8 in a homogenous time resolved fluorescence assay.

In some embodiments, the anti-IL-1RAcP antibody or antigen binding fragment thereof inhibits IL-1β-induced stimulation of cynomolgus dermal fibroblasts more strongly, such as with an $IC_{50}$ value that is at least three-fold lower, optionally with an $IC_{50}$ value that is at least five-fold lower, under the same in vitro assay conditions, than a reference antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof inhibits IL-1β-induced stimulation of cynomolgus dermal fibroblasts more strongly, such as with an $IC_{50}$ value that is at least two-fold lower, under the same in vitro assay conditions, than a reference antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In some embodiments, the anti-IL-1RAcP antibody or antigen binding fragment thereof inhibits IL-1β-induced stimulation of cynomolgus dermal fibroblasts more strongly such as with an $IC_{50}$ value that is at least three-fold lower, optionally with an $IC_{50}$ value that is at least five-fold lower, under the same in vitro assay conditions, than a reference antibody consisting of two heavy and two light chains, wherein each heavy chain of the reference anti-IL-1RAcP antibody has the amino acid sequence of SEQ ID NO: 31, and wherein each light chain of the reference anti-IL-1RAcP antibody has the amino acid sequence of SEQ ID NO: 32.

In some embodiments, the anti-IL-1RAcP antibody or antigen binding fragment thereof inhibits IL-1β-induced stimulation of cynomolgus dermal fibroblasts more strongly such as with an $IC_{50}$ value that is at least two-fold lower, under the same in vitro assay conditions, than each of the following:
   (d) a first reference antibody consisting of two heavy and two light chains, wherein each heavy chain of the first reference anti-IL-1RAcP antibody has the amino acid sequence of SEQ ID NO: 51, and wherein each light chain of the first reference anti-IL-1RAcP antibody has the amino acid sequence of SEQ ID NO: 52;
   (e) a second reference antibody consisting of two heavy and two light chains, wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36; and
   (f) a third reference antibody consisting of two heavy and two light chains, wherein each heavy chain of the first reference anti-IL-1RAcP antibody has the amino acid sequence of SEQ ID NO: 31, and wherein each light chain of the first reference anti-IL-1RAcP antibody has the amino acid sequence of SEQ ID NO: 32.

In some embodiments, the anti-IL-1RAcP antibody or antigen binding fragment thereof binds to the same epitope as a reference anti-IL-1RAcP antibody, wherein the reference anti-IL-1RAcP antibody consists of two heavy and two light chains, wherein each heavy chain of the reference anti-IL-1RAcP antibody has the amino acid sequence of SEQ ID NO: 19, and wherein each light chain of the reference anti-IL-1RAcP antibody has the amino acid sequence of SEQ ID NO: 20.

In some embodiments, inhibition of IL-1β-induced stimulation of cynomolgus dermal fibroblasts is determined by measuring the concentration of IL-8 in the culture medium.

In some embodiments, the anti-IL-1RAcP antibody or antigen binding fragment thereof inhibits IL-1β-induced stimulation of cynomolgus dermal fibroblasts with an $IC_{50}$ value of less than 0.10 nM when measured in an assay comprising:
   (i) suspending cynomolgus dermal fibroblasts in a culture medium and seeding 3500 cells/well in a microtitre (collagen coated 384-well) plate,
   (ii) adding the antibody or antigen binding fragment thereof to the cells (two hours after plating),
   (iii) incubating for 30 minutes,
   (iv) adding cynomolgus IL-1β to the cells to a final concentration of 1 pM,
   (v) incubating the plate for 24 hours at 37° C. in a humidified incubator,
   (vi) obtaining a sample of the supernatant and quantifying IL-8 in a homogenous time resolved fluorescence assay.

In some embodiments, the anti-IL-1RAcP antibody or antigen binding fragment thereof competes for binding to human IL-1RAcP with a reference anti-IL-1RAcP disulphide-linked Fab (FabCys), wherein each VH domain of the reference anti-IL-1RAcP FabCys has the sequence of SEQ ID NO: 15, and wherein each VL domain of the reference anti-IL-1RAcP FabCys has the sequence of SEQ ID NO: 16.

In some embodiments, competition is assessed using an ELISA-based competition assay (at 25° C.) in which the reference antibody is coated on a plate and a preformed complex of biotinylated human IL-1RAcP and the anti-IL-1RAcP antibody or antigen binding fragment thereof is added to the plate.

In some embodiments, the anti-IL-1RAcP antibody or antigen binding fragment thereof competes for binding to human IL-1RAcP with a first reference anti-IL-1RAcP disulphide-linked Fab (FabCys) and does not compete for binding to human IL-1RAcP with a second reference anti-IL-1RAcP FabCys,
   wherein each $V_H$ domain of the first reference anti-IL-1RAcP FabCys has the sequence of SEQ ID NO: 15, and wherein each VL domain of the first reference anti-IL-1RAcP FabCys has the sequence of SEQ ID NO: 16, and
   wherein each $V_H$ domain of the second reference anti-IL-1RAcP FabCys has the sequence of SEQ ID NO: 53, and wherein each VL domain of the second reference anti-IL-1RAcP FabCys has the sequence of SEQ ID NO: 54.

In some embodiments, the anti-IL-1RAcP antibody or antigen binding fragment thereof competes for binding to human IL-1RAcP with a first reference anti-IL-1RAcP disulphide-linked Fab (FabCys) and does not compete for binding to human IL-1RAcP with any of a second, third and fourth reference anti-IL-1RAcP FabCys, wherein each $V_H$ domain of the first reference anti-IL-1RAcP FabCys has the sequence of SEQ ID NO: 15, and wherein each VL domain of the first reference anti-IL-1RAcP FabCys has the sequence of SEQ ID NO: 16, wherein each $V_H$ domain of the second reference anti-IL-1RAcP FabCys has the sequence of SEQ ID NO: 53, and wherein each VL domain of the second reference anti-IL-1RAcP FabCys has the sequence of SEQ ID NO: 54, wherein each $V_H$ domain of the third reference anti-IL-1RAcP FabCys has the sequence of SEQ ID NO: 33, and wherein each VL domain of the second reference anti-IL-1RAcP FabCys has the sequence of SEQ ID NO: 34, and wherein each $V_H$ domain of the fourth reference anti-IL-1RAcP FabCys has the sequence of SEQ ID NO: 49, and wherein each VL domain of the second reference anti-IL-1RAcP FabCys has the sequence of SEQ ID NO: 50.

In some embodiments, competition is assessed using an ELISA-based competition assay (at 25° C.) in which the reference antibody is coated on a plate and a preformed complex of biotinylated human IL-1RAcP and the anti-IL-1RAcP antibody or antigen binding fragment thereof is added to the plate.

In one aspect the present disclosure provides, an anti-IL-1RAcP antibody or antigen binding fragment thereof comprising complementarity determining regions (CDRs) with the amino acid sequences of:
  i. SEQ ID NO: 12 for CDR1 of the heavy chain;
  ii. SEQ ID NO: 13 for CDR2 of the heavy chain;
  iii. SEQ ID NO: 14 for CDR3 of the heavy chain;
  iv. SEQ ID NO: 9 for CDR1 of the light chain;
  v. SEQ ID NO: 10 for CDR2 of the light chain; and
  vi. SEQ ID NO: 11 for CDR3 of the light chain.

In one aspect the present disclosure provides an anti-IL-1RAcP antibody or antigen binding fragment thereof comprising a heavy chain variable region of the amino acid sequence of SEQ ID NO: 15.

In one aspect the present disclosure provides, an anti-IL-1RAcP antibody or antigen binding fragment thereof comprising a light chain variable region of the amino acid sequence of SEQ ID NO: 16.

In one aspect the present disclosure provides, an anti-IL-1RAcP antibody or antigen binding fragment thereof comprising: (i) a heavy chain variable region of the amino acid sequence of SEQ ID NO: 15, and (ii) a light chain variable region of the amino acid sequence of SEQ ID NO: 16.

In one aspect the present disclosure provides, an anti-IL-1RAcP antibody comprising a heavy chain of the amino acid sequence of SEQ ID NO: 19.

In one aspect the present disclosure provides an anti-IL-1RAcP antibody comprising a light chain of the amino acid sequence of SEQ ID NO: 20.

In one aspect the present disclosure provides an anti-IL-1RAcP antibody comprising a heavy chain of the amino acid sequence of SEQ ID NO: 19, and a light chain of the amino acid sequence of SEQ ID NO: 20.

In one aspect the present disclosure provides an anti-IL-1RAcP antibody comprising two heavy and two light chains, wherein each heavy chain comprises a heavy chain variable region of the amino acid sequence of SEQ ID NO: 15, and wherein each light chain comprises a light chain variable region of the amino acid sequence of SEQ ID NO: 16.

In one aspect the present disclosure provides an anti-IL-1RAcP antibody consisting of two heavy and two light chains, wherein each heavy chain has the amino acid sequence of SEQ ID NO: 19, and wherein each light chain has the amino acid sequence of SEQ ID NO: 20.

In one aspect, the present disclosure provides, the following antibodies, or antigen binding fragments thereof, which are defined by reference to specific structural characteristics, i.e. specified amino acid sequences of either the CDRs (one or more of SEQ ID NOS: 4, 5, 6, 12, 13, 14, (heavy chain CDRs) or SEQ ID NOS: 1, 2, 3, 9, 10, 11, (light chain CDRs)) or entire variable domains (one or more of SEQ ID NOS 7, 15, (heavy chain variable domains) or SEQ ID NOS: 8, 16 (light chain variable domains)). All of these antibodies bind to the human cytokine receptor IL-1RAcP.

In one aspect the present disclosure provides an antibody or antigen binding fragment thereof, which binds to the cytokine receptor IL1RAcP, said antibody or antigen binding fragment comprises a heavy chain variable domain (VH) comprising a heavy chain CDR3 selected from: SEQ ID NO: 6, or sequence variant thereof, or SEQ ID NO: 14: or sequence variant thereof, wherein the sequence variant optionally comprises one, two or three amino acid substitutions (e.g. conservative substitution, or affinity variants) in the recited sequence.

In one aspect the present disclosure provides the heavy chain variable domain of the antibody or antigen binding fragment thereof, which may alternatively or in addition comprise a heavy chain CDR2 selected from: SEQ ID NO: 5 or sequence variant thereof, or SEQ ID NO: 13 or sequence variant thereof, wherein the sequence variant optionally comprises one, two or three amino acid substitutions (e.g. conservative substitutions, or affinity variants) in the recited sequence.

In one aspect the present disclosure provides the heavy chain variable domain of the antibody or antigen binding fragment thereof which may alternatively or in addition comprise a heavy chain CDR1 selected from: SEQ ID NO: 4, or sequence variant thereof, or SEQ ID NO: 12, or sequence variant thereof, wherein the sequence variant optionally comprises one, two or three amino acid substitutions (e.g. conservative substitutions, or affinity variants) in the recited sequence.

In one aspect the present disclosure provides the antibodies or antigen binding fragment thereof, which bind to the cytokine receptor IL-1RAcP, and comprises a light chain variable domain (VL) comprising a light chain CDR3 selected from: SEQ ID NO: 1 or sequence variant thereof, or SEQ ID NO: 9, or sequence variant thereof, wherein the sequence variant optionally comprises one, two or three amino acid substitutions (e.g. conservative substitutions, or affinity variants) in the recited sequence.

In some embodiments, the light chain variable domain of the antibody or antigen binding fragment thereof may alternatively or in addition comprise a light chain CDR2 selected from: SEQ ID NO: 2 or sequence variant thereof or SEQ ID NO: 10 or sequence variant thereof, wherein the sequence variant optionally comprises one, two or three amino acid substitutions (e.g. conservative substitutions, or affinity variants) in the recited sequence.

In some embodiments, the light chain variable domain of the antibody or antigen binding fragment thereof may alternatively or in addition comprise a light chain CDR3 selected from: SEQ ID NO: 3 or sequence variant thereof, or SEQ ID NO: 11 or sequence variant thereof, wherein the sequence variant optionally comprises one, two or three amino acid substitutions (e.g. conservative substitutions, or affinity variants) in the recited sequence.

In one aspect the present disclosure provides an antibody or antigen binding fragment thereof, which binds to the cytokine receptor IL-1RAcP, the antibody or antigen binding fragment thereof comprising a combination of variable heavy chain CDR3 (HCDR3), variable heavy chain CDR2 (HCDR2) and variable heavy chain CDR1 (HCDR1) wherein the combination is selected from the group consisting of:
  (i) HCDR3 comprising SEQ ID NO: 6; HCDR2 comprising SEQ ID NO: 5 or 13; HCDR1 comprising SEQ ID NO: 4 or 12 and
  (ii) HCDR3 comprising SEQ ID NO: 14; HCDR2 comprising SEQ ID NO: 5 or 13; HCDR1 comprising SEQ ID NO: 4 or 12

In one aspect, the present disclosure provides antibodies or antigen binding fragments thereof, which bind to the cytokine receptor IL-1RAcP, wherein the antibodies or antigen binding fragments comprise a combination of variable heavy chain CDR3 (HCDR3), variable heavy chain CDR2 (HCDR2) and variable heavy chain CDR1 (HCDR1), variable light chain CDR3 (LCDR3), variable light chain CDR2 (LCDR2) and variable light chain CDR1 (LCDR1) according to the embodiments described.

In one aspect, the present disclosure provides an antibody or antigen binding fragment specific for IL-1RAcP wherein said antibody or antigen binding fragment comprises
  (a) a HCDR1 region comprising the amino acid sequence of SEQ ID NO: 4, a HCDR2 region comprising the amino acid sequence of SEQ ID NO: 5, a HCDR3 region comprising the amino acid sequence of SEQ ID NO: 6, a LCDR1 region comprising the amino acid sequence of SEQ ID NO: 1, a LCDR2 region comprising the amino acid sequence of SEQ ID NO: 2 and a LCDR3 region comprising the amino acid sequence of SEQ ID NO: 3, and/or
  (b) a HCDR1 region comprising the amino acid sequence of SEQ ID NO: 12, a HCDR2 region comprising the amino acid sequence of SEQ ID NO: 13, a HCDR3 region comprising the amino acid sequence of SEQ ID NO: 14, a LCDR1 region comprising the amino acid sequence of SEQ ID NO: 9, a LCDR2 region comprising the amino acid sequence of SEQ ID NO: 10, and a LCDR3 region comprising the amino acid sequence of SEQ ID NO: 11;

In one aspect, the present disclosure provides an antibody or antigen binding fragment specific for IL-1RAcP wherein said antibody or antigen binding fragment comprises
  (a) a HCDR1 region having the amino acid sequence of SEQ ID NO: 4, a HCDR2 region having the amino acid sequence of SEQ ID NO: 5, a HCDR3 region having the amino acid sequence of SEQ ID NO: 6, a LCDR1 region having the amino acid sequence of SEQ ID NO: 1, a LCDR2 region having the amino acid sequence of SEQ ID NO: 2 and a LCDR3 region having the amino acid sequence of SEQ ID NO: 3, and/or
  (b) a HCDR1 region having the amino acid sequence of SEQ ID NO: 12, a HCDR2 region having the amino acid sequence of SEQ ID NO: 13, a HCDR3 region having the amino acid sequence of SEQ ID NO: 14, a LCDR1 region having the amino acid sequence of SEQ ID NO: 9, a LCDR2 region having the amino acid sequence of SEQ ID NO: 10 and a LCDR3 region having the amino acid sequence of SEQ ID NO: 11

In one aspect, the present disclosure provides an antibody or antigen binding fragment thereof, which binds to the cytokine receptor IL-1RAcP and comprises the CDR sequences: HCDR3 comprising SEQ ID NO: 6 HCDR2 comprising SEQ ID NO: 5; HCDR1 comprising SEQ ID NO: 4; LCDR3 comprising SEQ ID NO: 3; LCDR2 comprising SEQ ID NO: 2; and LCDR1 comprising SEQ ID NO: 1.

In one aspect, the present disclosure provides an antibody or antigen binding fragment thereof, which binds to the cytokine receptor IL-1RAcP and comprises the CDR sequences: HCDR3 having SEQ ID NO: 6; HCDR2 having SEQ ID NO: 5; HCDR1 having SEQ ID NO: 4; LCDR3 having SEQ ID NO: 3; LCDR2 having SEQ ID NO: 2; and LCDR1 having SEQ ID NO: 1.

In one aspect, the present disclosure provides an antibody or antigen binding fragment thereof, which binds to the cytokine receptor IL-1RAcP and comprises the CDR sequences: HCDR3 comprising SEQ ID NO: 14; HCDR2 comprising SEQ ID NO: 13; HCDR1 comprising SEQ ID NO: 12. LCDR3 comprising SEQ ID NO: 11; LCDR2 comprising SEQ ID NO: 10; and LCDR1 comprising SEQ ID NO: 9.

In one aspect, the present disclosure provides an antibody or antigen binding fragment thereof, which binds to the cytokine receptor IL-1RAcP and comprises the CDR sequences: HCDR3 having the SEQ ID NO: 14; HCDR2 having the SEQ ID NO: 13; HCDR1 having SEQ ID NO: 12; LCDR3 having SEQ ID NO: 11; LCDR2 having SEQ ID NO: 10; and LCDR1 having SEQ ID NO: 9.

In one aspect, the present disclosure provides antibodies or antigen binding fragments thereof, which bind to the cytokine receptor IL-1RAcP, wherein the antibodies or antigen binding fragments comprise a heavy chain variable domain (VH) selected from the following:
  (i) a VH comprising or consisting of the amino acid sequence of SEQ ID NO: 7 or 15; or
  (ii) a VH comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% identity to the amino acid sequence of SEQ ID NO: 7 or 15.

In one aspect, the present disclosure provides antibodies or antigen binding fragments thereof, which bind to the cytokine receptor IL-1RAcP, wherein the antibodies or antigen binding fragments comprise a light chain variable domain (VL) selected from the following:
  (i) a VL comprising or consisting of the amino acid sequence of SEQ ID NO: 8 or 16; or
  (ii) a VL comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 8 or 16.

In one aspect, the present disclosure provides antibodies or antigen binding fragments thereof, which bind to the cytokine receptor IL-1RAcP, wherein the antibodies or antigen binding fragments comprise a heavy chain variable domain (VH) and a light chain variable domain selected from the following:
  (i) a VH comprising or consisting of the amino acid sequence of SEQ ID NO: 7 or 15;
  (ii) a VL comprising or consisting of the amino acid sequence of SEQ ID NO: 8 or 16.

In one aspect, the present disclosure provides the domains of the antibodies or antigen binding fragments are defined by a particular percentage sequence identity to a reference sequence, the VH and/or VL domains may retain identical CDR sequences to those present in the reference sequence such that the variation is present only within the framework regions.

In one aspect, the present disclosure provides an antibody or an antigen-binding fragment thereof specific for IL-1RAcP wherein said antibody or antigen-binding fragment comprises
  (a) a HCDR1 region comprising the amino acid sequence of SEQ ID NO: 4, a HCDR2 region comprising the amino acid sequence of SEQ ID NO: 5, a HCDR3 region comprising the amino acid sequence of SEQ ID NO: 6, a LCDR1 region comprising the amino acid sequence of SEQ ID NO: 1, a LCDR2 region comprising the amino acid sequence of SEQ ID NO: 2 and a LCDR3 region comprising the amino acid sequence of SEQ ID NO: 3, and/or
  (b) a HCDR1 region comprising the amino acid sequence of SEQ ID NO: 12, a HCDR2 region comprising the amino acid sequence of SEQ ID NO: 13, a HCDR3 region comprising the amino acid sequence of SEQ ID NO: 14, a LCDR1 region comprising the amino acid sequence of SEQ ID NO: 9, a LCDR2 region comprising the amino acid sequence of SEQ ID NO: 10 and a LCDR3 region comprising the amino acid sequence of SEQ ID NO: 11;
  and/or comprise a heavy chain variable domain ($V_H$) selected from the following:
    (i) a $V_H$ comprising or consisting of the amino acid sequence of SEQ ID NO: 7 or 15; or
    (ii) a $V_H$ comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 7 or 15;
  and/or comprise a light chain variable domain (VL) selected from the following:
    (i) a VL comprising or consisting of the amino acid sequence of SEQ ID NO: 8 or 16 or
    (ii) a VL comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 8 or 16.

In one aspect, the present disclosure provides an antibody or antigen binding fragment specific for IL-1RAcP wherein said antibody or antigen binding fragment comprises
  (a) a HCDR1 region having the amino acid sequence of SEQ ID NO: 4, a HCDR2 region having the amino acid sequence of SEQ ID NO: 5, a HCDR3 region having the amino acid sequence of SEQ ID NO: 6, a LCDR1 region having the amino acid sequence of SEQ ID NO: 1, a LCDR2 region having the amino acid sequence of SEQ ID NO: 2 and a LCDR3 region having the amino acid sequence of SEQ ID NO: 3, and/or
  (b) a HCDR1 region having the amino acid sequence of SEQ ID NO: 12, a HCDR2 region having the amino acid sequence of SEQ ID NO: 13, a HCDR3 region having the amino acid sequence of SEQ ID NO: 14, a LCDR1 region having the amino acid sequence of SEQ ID NO: 9, a LCDR2 region having the amino acid sequence of SEQ ID NO: 10 and a LCDR3 region having the amino acid sequence of SEQ ID NO: 11;
  and/or comprise a heavy chain variable domain (VH) selected from the following:
    (i) a VH comprising or consisting of the amino acid sequence of SEQ ID NO: 7 or 15; or
    (ii) a VH comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 7 or 15 and/or comprise a light chain variable domain (VL) selected from the following:
    (i) a VL comprising or consisting of the amino acid sequence of SEQ ID NO: 8 or 16 or
    (ii) a VL comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 8 or 16.

In one aspect, the present disclosure provides an antibody, or antigen binding fragment thereof, which specifically binds IL-1RAcP, said antibody or antigen binding fragment comprising a heavy chain variable domain wherein:
  the variable heavy chain CDR3 sequence is SEQ ID NO: 6 or sequence variant thereof;
  the variable heavy chain CDR2 sequence is SEQ ID NO: 5 or sequence variant thereof; and
  the variable heavy chain CDR1 sequence is SEQ ID NO: 4 or sequence variant thereof, and optionally wherein the sequence variant comprises one, two or three amino acid substitutions (e.g., conservative substitutions, or affinity variants) in the recited sequence.

In one aspect, the present disclosure provides an antibody or antigen binding fragment thereof may further comprise a light chain variable domain wherein:
  the variable light chain CDR3 sequence is SEQ ID NO: 3, or sequence variant thereof;
  the variable light chain CDR2 sequence is SEQ ID NO: 2, or sequence variant thereof; and
  the variable light chain CDR1 sequence is SEQ ID NO: 1, or sequence variant thereof, and optionally wherein the sequence variant comprises one, two or three amino acid substitutions (e.g., conservative substitutions, or affinity variants) in the recited sequence.

In one aspect, the present disclosure provides the antibodies or antigen binding fragments thereof may comprise a heavy chain variable domain (VH) comprising the amino acid sequence of SEQ ID NO: 7 and optionally a light chain variable domain (VL) comprising the amino acid sequence of SEQ ID NO: 8. In certain embodiments, provided herein are monoclonal antibodies or antigen binding fragments thereof, comprising a heavy chain variable domain and a light chain variable domain, the heavy chain variable domain comprising a VH sequence with at least 80%, 81%, 82%, 83%, 84%, 85%, 86%, 87%, 88%, 89%, 90%, 91%, 92%, 93%, 94%, 95%, 96%, 97%, 98% or 99% sequence identity, to the amino acid sequence shown as SEQ ID NO: 7 and/or the light chain variable domain comprising a VL with at least 80%, 81%, 82%, 83%, 84%, 85%, 86%, 87%, 88%, 89%, 90%, 91%, 92%, 93%, 94%, 95%, 96%, 97%, 98% or 99% sequence identity, to the amino acid sequence shown as SEQ ID NO: 8. In some embodiments, the VH and/or VL domains may retain identical CDR sequences to those present in the reference sequence such that the variation is present only within the framework regions.

In one aspect, the present disclosure provides, the antibodies or antigen binding fragments comprising heavy chain variable domains and/or light chain variable domains defined as having a particular percentage identity to SEQ ID NOS 7 and 8 respectively having the following CDR sequences:
- a variable heavy chain CDR3 sequence comprising or consisting of SEQ ID NO: 6;
- a variable heavy chain CDR2 sequence comprising or consisting of SEQ ID NO: 5;
- a variable heavy chain CDR1 sequence comprising or consisting of SEQ ID NO: 4;
- a variable light chain CDR3 sequence comprising or consisting of SEQ ID NO: 3;
- a variable light chain CDR2 sequence comprising or consisting of SEQ ID NO: 2; and
- a variable light chain CDR1 sequence comprising or consisting of SEQ ID NO: 1.

In one aspect, the present disclosure provides the antibodies which specifically bind IL-1RAcP comprising at least one full-length immunoglobulin heavy chain and/or at least one full-length lambda or kappa light chain.

In one aspect, the present disclosure provides the antibodies comprising a heavy chain comprising the amino acid sequence of SEQ ID NO: 17 and a light chain comprising the amino acid sequence of SEQ ID NO: 18. In certain embodiments, provided herein are monoclonal antibodies comprising a heavy chain with at least 80%, 81%, 82%, 83%, 84%, 85%, 86%, 87%, 88%, 89%, 90%, 91%, 92%, 93%, 94%, 95%, 96%, 97%, 98% or 99% sequence identity, to the amino acid sequence shown as SEQ ID NO: 17 and/or a light chain with at least 80%, 81%, 82%, 83%, 84%, 85%, 86%, 87%, 88%, 89%, 90%, 91%, 92%, 93%, 94%, 95%, 96%, 97%, 98% or 99% sequence identity, to the amino acid sequence shown as SEQ ID NO: 18.

In some embodiments, the heavy chain and/or light chain may retain identical CDR sequences to those present in the reference sequence such that the variation is present only outside the CDR regions.

In one aspect, the present disclosure provides an antibody, or antigen binding fragment thereof, which specifically binds IL-1RAcP, said antibody or antigen binding fragment comprising a heavy chain variable domain wherein:
- the variable heavy chain CDR3 sequence is SEQ ID NO: 14 or sequence variant thereof;
- the variable heavy chain CDR2 sequence is SEQ ID NO: 13: or sequence variant thereof; and
- the variable heavy chain CDR1 sequence is SEQ ID NO: 12 or sequence variant thereof, and
- wherein the sequence variant comprises one, two or three amino acid substitutions (e.g., conservative substitutions, or affinity variants) in the recited sequence.

In one aspect, the present disclosure provides the antibody or antigen binding fragment further comprises a light chain variable domain wherein:
- the variable light chain CDR3 sequence is SEQ ID NO: 11 or sequence variant thereof;
- the variable light chain CDR2 sequence is SEQ ID NO: 10 or sequence variant thereof; and
- the variable light chain CDR1 sequence is SEQ ID NO: 9 or sequence variant thereof, and
- wherein the sequence variant comprises one, two or three amino acid substitutions (e.g., conservative substitutions, or affinity variants) in the recited sequence.

In one aspect, the present disclosure provides an isolated antibody, or antigen binding fragment thereof, which specifically binds IL-1RAcP, said antibody or antigen binding fragment comprising a heavy chain variable domain wherein:
- the variable heavy chain CDR3 sequence comprises or consists of SEQ ID NO: 14;
- the variable heavy chain CDR2 sequence comprises or consists of SEQ ID NO: 13;
- the variable heavy chain CDR1 sequence comprises or consists of SEQ ID NO: 12;
- the variable light chain CDR3 sequence comprises or consists of SEQ ID NO: 11;
- the variable light chain CDR2 sequence comprises or consists of SEQ ID NO: 10; and
- the variable light chain CDR1 sequence comprises or consists of SEQ ID NO: 9.

In one aspect, the present disclosure provides the antibodies or antigen binding fragments thereof comprise a heavy chain variable domain (VH) comprising the amino acid sequence of SEQ ID NO: 15 and optionally a light chain variable domain (VL) comprising the amino acid sequence of SEQ ID NO: 16. In certain embodiments, provided herein are monoclonal antibodies or antigen binding fragments thereof, comprising a heavy chain variable domain and a light chain variable domain, the heavy chain variable domain comprising a VH sequence with at least 80%, 81%, 82%, 83%, 84%, 85%, 86%, 87%, 88%, 89%, 90%, 91%, 92%, 93%, 94%, 95%, 96%, 97%, 98% or 99% sequence identity, to the amino acid sequence shown as SEQ ID NO: 15 and/or the light chain variable domain comprising a VL with at least 80%, 81%, 82%, 83%, 84%, 85%, 86%, 87%, 88%, 89%, 90%, 91%, 92%, 93%, 94%, 95%, 96%, 97%, 98% or 99% sequence identity, to the amino acid sequence shown as SEQ ID NO: 16.

In some embodiments, the VH and/or VL domains may retain identical CDR sequences to those present in the reference sequence such that the variation is present only within the framework regions.

In one aspect, the present disclosure provides the antibodies or antigen binding fragments comprising heavy chain variable domains and/or light chain variable domains defined as having a particular percentage identity to SEQ ID NOS: 15 and 16, respectively having the following CDR sequences:
- a variable heavy chain CDR3 sequence comprising or consisting of SEQ ID NO: 14;
- a variable heavy chain CDR2 sequence comprising or consisting of SEQ ID NO: 13;
- a variable heavy chain CDR1 sequence comprising or consisting of SEQ ID NO: 12;
- a variable light chain CDR3 sequence comprising or consisting of SEQ ID NO: 11;
- a variable light chain CDR2 sequence comprising or consisting of SEQ ID NO: 10; and
- a variable light chain CDR1 sequence comprising or consisting of SEQ ID NO: 9.

In one aspect, the present disclosure provides the antibodies which specifically bind IL-1RAcP may comprise at least one full-length immunoglobulin heavy chain and/or at least one full-length lambda or kappa light chain. In certain embodiments of the disclosure the framework sequences is VH YLAN_VH3-74 and the VL is YLAN_VK1-05. In certain embodiments, the antibodies comprise a heavy chain comprising the amino acid sequence of SEQ ID NO: 19 and a light chain comprising the amino acid sequence of SEQ ID NO: 20. In certain embodiments, provided herein are monoclonal antibodies comprising a heavy chain with at least 80%, 81%, 82%, 83%, 84%, 85%, 86%, 87%, 88%, 89%, 90%, 91%, 92%, 93%, 94%, 95%, 96%, 97%, 98% or 99% sequence identity, to the amino acid sequence shown as SEQ ID NO: 19 and/or a light chain with at least 80%, 81%, 82%, 83%, 84%, 85%, 86%, 87%, 88%, 89%, 90%, 91%, 92%, 93%, 94%, 95%, 96%, 97%, 98% or 99% sequence identity, to the amino acid sequence shown as SEQ ID NO: 20.

For embodiments wherein the chains of the antibodies are defined by a particular percentage sequence identity to a reference sequence, the heavy chain and/or light chain may retain identical CDR sequences to those present in the reference sequence such that the variation is present only outside the CDR regions.

In one aspect, the present disclosure provides antibodies, or antigen-binding regions, which are identified as comprising a combination of a VH domain or heavy chain, defined by reference to a specific amino acid sequence, and a VL domain or a light chain, also defined by reference to a specific amino acid sequence, then for each specific VH/VL or heavy chain/light chain combination listed (unless otherwise stated) this definition may be taken to include antibodies, or antigen binding fragments, formed by combination of a VH domain/heavy chain having at least 80%, 81%, 82%, 83%, 84%, 85%, 86%, 87%, 88%, 89%, 90%, 91%, 92%, 93%, 94%, 95%, 96%, 97%, 98% or 99% sequence identity to the stated VH/heavy chain amino acid sequence and a VL domain/light chain having at least 80%, 81%, 82%, 83%, 84%, 85%, 86%, 87%, 88%, 89%, 90%, 91%, 92%, 93%, 94%, 95%, 96%, 97%, 98% or 99% sequence identity to the stated VL/light chain amino acid sequence. In each case the domains/chains defined by % sequence identity to the stated domain/chain amino acid sequences may retain identical CDR sequences to those present in the stated VH/VL domain or heavy/light chain amino acid sequences, whilst exhibiting amino acid sequence variation within the framework regions or other regions outside the CDR regions.

In one aspect, the present disclosure provides an anti-IL-1RAcP antibody or antigen binding fragment thereof that competes for binding to human IL-1RAcP with a first reference anti-IL-1RAcP disulphide-linked Fab (FabCys) and does not compete for binding to human IL-1RAcP with a second reference anti-IL-1RAcP FabCys, wherein each $V_H$ domain of the first reference anti-IL-1RAcP FabCys has the sequence of SEQ ID NO: 7, and wherein each $V_L$ domain of the first reference anti-IL-1RAcP FabCys has the sequence of SEQ ID NO: 8, and wherein each $V_H$ domain of the second reference anti-IL-1RAcP FabCys has the sequence of SEQ ID NO: 53, and wherein each $V_L$ domain of the second reference anti-IL-1RAcP FabCys has the sequence of SEQ ID NO: 54.

In some embodiments, competition is assessed using an ELISA-based competition assay (at 25° C.) in which the reference antibody is coated on a plate and a preformed complex of biotinylated human IL-1RAcP and the anti-IL-1RAcP antibody or antigen binding fragment thereof is added to the plate.

In one aspect, the present disclosure provides, the anti-IL-1RAcP antibody or antigen binding fragment thereof binds to human IL-1RAcP with a $K_D$ that is lower than the $K_D$ determined under the same assay conditions (such as surface plasmon resonance, e.g. at 25° C., or solution equilibrium titration, e.g., at 25° C.) for each of:
(i) a first reference anti-IL-1RAcP antibody consisting of two heavy and two light chains,
 wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36, and
(ii) a second reference anti-IL-1RAcP antibody consisting of two heavy and two light chains,
 wherein each heavy chain of the second reference anti-IL-1RAcP antibody has the amino acid sequence of SEQ ID NO: 51, and wherein each light chain of the second reference anti-IL-1RAcP antibody has the amino acid sequence of SEQ ID NO: 52.

In one aspect, the present disclosure provides, the anti-IL-1RAcP antibody or antigen binding fragment thereof competes for binding to human IL-1RAcP with a first reference anti-IL-1RAcP disulphide-linked Fab (FabCys) and does not compete for binding to human IL-1RAcP with any of a second, third and fourth reference anti-IL-1RAcP FabCys,
wherein each $V_H$ domain of the first reference anti-IL-1RAcP FabCys has the sequence of SEQ ID NO: 7, and wherein each $V_L$ domain of the first reference anti-IL-1RAcP FabCys has the sequence of SEQ ID NO: 8,
wherein each $V_H$ domain of the second reference anti-IL-1RAcP FabCys has the sequence of SEQ ID NO: 53, and wherein each $V_L$ domain of the second reference anti-IL-1RAcP FabCys has the sequence of SEQ ID NO: 54,
wherein each $V_H$ domain of the third reference anti-IL-1RAcP FabCys has the sequence of SEQ ID NO: 33, and wherein each $V_L$ domain of the second reference anti-IL-1RAcP FabCys has the sequence of SEQ ID NO: 34, and
wherein each $V_H$ domain of the fourth reference anti-IL-1RAcP FabCys has the sequence of SEQ ID NO: 49, and wherein each $V_L$ domain of the second reference anti-IL-1RAcP FabCys has the sequence of SEQ ID NO: 50.

In some embodiments, competition is assessed using an ELISA-based competition assay (at 25° C.) in which the reference antibody is coated on a plate and a preformed complex of biotinylated human IL-1RAcP and the anti-IL-1RAcP antibody or antigen binding fragment thereof is added to the plate.

In some embodiments, the anti-IL-1RAcP antibody or antigen binding fragment thereof, binds to human IL-1RAcP with a $K_D$ of 5 pM or less, as determined using solution equilibrium titration, e.g., at 25° C.

In one aspect, the present disclosure provides, the anti-IL-1RAcP antibody or antigen binding fragment thereof, which inhibits IL-1α-induced stimulation of human dermal fibroblasts more strongly, such as with an $IC_{50}$ value that is at least two-fold lower, under the same in vitro assay conditions, than a reference antibody consisting of two heavy and two light chains, wherein each heavy chain of the reference anti-IL-1RAcP antibody has the amino acid sequence of SEQ ID NO: 51, and wherein each light chain of the reference anti-IL-1RAcP antibody has the amino acid sequence of SEQ ID NO: 52.

In some embodiments, the anti-IL-1RAcP antibody or antigen binding fragment thereof inhibits IL-1α-induced stimulation of human dermal fibroblasts more strongly, such as with an $IC_{50}$ value that is at least three-fold lower, optionally having an $IC_{50}$ value that is at least five-fold lower, under the same in vitro assay conditions, than a reference antibody consisting of two heavy and two light chains, wherein each heavy chain of the reference anti-IL-1RAcP antibody has the amino acid sequence of SEQ ID NO: 35, and wherein each light chain of the reference anti-IL-1RAcP antibody has the amino acid sequence of SEQ ID NO: 36.

In one aspect, the present disclosure provides, the anti-IL-1RAcP antibody or antigen binding fragment thereof inhibits IL-1α-induced stimulation of human dermal fibroblasts more strongly, such as with an $IC_{50}$ value that is at least three-fold lower, optionally having an $IC_{50}$ value that is at least five-fold lower, under the same in vitro assay conditions, than a reference antibody consisting of two heavy and two light chains, wherein each heavy chain of the reference anti-IL-1RAcP antibody has the amino acid sequence of SEQ ID NO: 31, and wherein each light chain of the reference anti-IL-1RAcP antibody has the amino acid sequence of SEQ ID NO: 32.

In one aspect, the present disclosure provides, the anti-IL-1RAcP antibody or antigen binding fragment thereof, inhibits IL-1α-induced stimulation of human dermal fibroblasts more strongly such as with an $IC_{50}$ value that is at least two-fold lower, under the same in vitro assay conditions, than each of the following:
  (a) a first reference antibody consisting of two heavy and two light chains, wherein each heavy chain of the first reference anti-IL-1RAcP antibody has the amino acid sequence of SEQ ID NO: 51, and wherein each light chain of the first reference anti-IL-1RAcP antibody has the amino acid sequence of SEQ ID NO: 52;
  (b) a second reference antibody consisting of two heavy and two light chains, wherein each heavy chain of the first reference anti-IL-1RAcP antibody has the amino acid sequence of SEQ ID NO: 35, and wherein each light chain of the first reference anti-IL-1RAcP antibody has the amino acid sequence of SEQ ID NO: 36; and
  (c) a third reference antibody consisting of two heavy and two light chains, wherein each heavy chain of the first reference anti-IL-1RAcP antibody has the amino acid sequence of SEQ ID NO: 31, and wherein each light chain of the first reference anti-IL-1RAcP antibody has the amino acid sequence of SEQ ID NO: 32.

In some embodiments, inhibition of IL-1α-induced stimulation of human dermal fibroblasts is determined by measuring the concentration of IL-8 in the culture medium.

In some embodiments, the anti-IL-1RAcP antibody or antigen binding fragment thereof inhibits IL-1α-induced stimulation of human dermal fibroblasts with an $IC_{50}$ value of less than 2.5 nM when measured in an assay comprising:
  (i) suspending human dermal fibroblasts in a culture medium and seeding in a microtitre (384-well) plate in a volume of 30 μl,
  (ii) adding the antibody or antigen binding fragment thereof to the cells two hours after plating,
  (iii) incubating for 30 minutes,
  (iv) adding IL-1α to the cells to a final concentration of 2 pM,
  (v) incubating the plate for 24 hours at 37° C. in a humidified incubator,
  (vi) obtaining a sample of the supernatant and quantifying IL-8 in a homogenous time resolved fluorescence assay.

In one aspect, the present disclosure provides an antibody or antigen binding fragment that cross-competes with an antibody described in Table 1. In one aspect, the present disclosure provides an antibody or antigen binding fragment, wherein said antibody or antigen binding fragment cross-competes with an antibody or antigen binding fragment comprising 6 CDRs defined by Kabat of one of the antibodies in Table 1. In one aspect, the present disclosure provides an antibody or antigen binding fragment specific for human IL-1RAcP wherein said antibody or antigen binding fragment bivalently binds to an IL-1RAcP homodimer and forms a complex consisting of said antibody or antigen binding fragment and one IL-1RAcP homodimer and wherein said antibody or antigen binding fragment cross-competes with an antibody or antigen binding fragment comprising 6 CDRs defined by Kabat of one of the antibodies in Table 1.

In one aspect, the present disclosure provides an antibody or antigen binding fragment, wherein said antibody or antigen binding fragment cross-competes with an antibody or antigen binding fragment comprising 6 CDRs, wherein the HCDR1 is the amino acid sequence of SEQ ID NO: 12 the HCDR2 is the amino acid sequence of SEQ ID NO: 13, the HCDR3 is the amino acid sequence of SEQ ID NO: 14, the LCDR1 is the amino acid sequence of SEQ ID NO: 9, the LCDR2 is the amino acid sequence of SEQ ID NO: 10 and the LCDR3 is the amino acid sequence of SEQ ID NO: 11. In some embodiments the present disclosure provides an antibody or antigen binding fragment, wherein said antibody or antigen binding fragment cross-competes with an antibody or antigen binding fragment comprising the VH according to SEQ ID NO: 15 and the VL according to SEQ ID NO: 16.

In one aspect, the present disclosure provides an antibody or an antigen binding fragment, wherein said antibody or antigen binding fragment cross-competes with an antibody or antigen binding fragment comprising 6 CDRs, wherein the HCDR1 is the amino acid sequence of SEQ ID NO: 4, the HCDR2 is the amino acid sequence of SEQ ID NO: 5, the HCDR3 is the amino acid sequence of SEQ ID NO: 6, the LCDR1 is the amino acid sequence of SEQ ID NO: 1, the LCDR2 is the amino acid sequence of SEQ ID No.: 2 and the LCDR3 is the amino acid sequence of SEQ ID NO: 3. In one aspect, the present disclosure provides an antibody or antigen binding fragment, wherein said antibody or antigen binding fragment cross competes with an antibody or antigen binding fragment comprising the VH according to SEQ ID NO: 7 and the VL according to SEQ ID NO: 8.

In the context of the present disclosure, cross-competing antibodies are those that bind IL-1RAcP at site(s) that overlap or are identical to the site(s) at which the present IL-1RAcP antibodies bind. Competing (monoclonal) antibodies or antigen-binding fragments thereof can be identified, for example, via an antibody competition assay. For example, an IL-1RAcP antigen or fragment thereof can be bound to a solid support. Then, an antibody or antigen binding fragment thereof of the present disclosure and an antibody or antigen-binding fragment thereof suspected of being able to compete with such disclosure antibody are added. One of the two molecules is labelled. If the labelled compound and the unlabelled compound bind to separate and discrete sites on the IL-1RAcP antigen, the labelled compound will bind to the same level whether or not the suspected competing compound is present. However, if the sites of interaction are identical (or overlapping), the unlabelled compound will compete, and the amount of labelled compound bound to the antigen will be lowered. If the unlabelled compound is present in excess, very little, if any, labelled compound will bind. For purposes of the present disclosure, competing antibodies (e.g., competing monoclonal antibodies) or antigen-binding fragments thereof are those that decrease the binding of the present antibodies to IL-1RAcP by about 50%, about 60%, about 70%, about 80%, about 85%, about 90%, about 95%, or about 99%.

Details of procedures for carrying out such competition assays are described in the current application.

In another embodiment the present disclosure provides an antibody or antigen binding fragment, wherein said antibody or antigen binding fragment binds to the same epitope as an antibody or antigen binding fragment comprising 6 CDRs, wherein the HCDR1 is the amino acid sequence of SEQ ID NO: 12 the HCDR2 is the amino acid sequence of SEQ ID NO: 13, the HCDR3 is the amino acid sequence of SEQ ID NO: 14, the LCDR1 is the amino acid sequence of SEQ ID NO: 9, the LCDR2 is the amino acid sequence of SEQ ID NO: 10 and the LCDR3 is the amino acid sequence of SEQ ID NO: 11. In one aspect, the present disclosure provides an antibody or antigen binding fragment, wherein said antibody or antigen binding fragment binds to the same epitope as an antibody or antigen binding fragment comprising the VH according to SEQ ID NO: 15 and the VL according to SEQ ID NO: 16.

In one aspect, the present disclosure provides an antibody or an antigen binding fragment, wherein said antibody or antigen binding fragment binds to the same epitope as an antibody or antigen binding fragment comprising 6 CDRs, wherein the HCDR1 is the amino acid sequence of SEQ ID NO: 4, the HCDR2 is the amino acid sequence of SEQ ID NO: 5, the HCDR3 is the amino acid sequence of SEQ ID NO: 6, the LCDR1 is the amino acid sequence of SEQ ID NO: 1, the LCDR2 is the amino acid sequence of SEQ ID No.: 2 and the LCDR3 is the amino acid sequence of SEQ ID NO: 3.

In one aspect, the present disclosure provides an antibody or antigen binding fragment, wherein said antibody or antigen binding fragment binds to the same epitope as an antibody or antigen binding fragment comprising the VH according to SEQ ID NO: 9 and the VL according to SEQ ID NO: 10.

In the context of the present disclosure the epitopes are determined by the binning data experiments as described herein. The experiments as disclosed show the antibodies of the present disclosure binds to a unique epitope when compared to antibodies of the prior art.

Binding Affinity

In certain embodiments, antibodies and antigen binding fragments of the disclosure bind to human IL-1RAcP with high affinity.

As used herein, the term "affinity" or "binding affinity" should be understood based on the usual meaning in the art in the context of antibody binding, and reflects the strength and/or stability of binding between an antigen and a binding site on an antibody or antigen binding fragment thereof.

The binding affinity of an antibody or antigen binding fragment thereof for its respective antigen can be determined experimentally using techniques known in the art. For example, Biacore® instruments measure affinity based on the immobilization of a target protein or antigen on a biosensor chip while the antibody or antigen binding fragment is passed over the immobilized target under specific flow conditions. These experiments yield $k_{on}$ and $k_{off}$ measurements, which can be translated into $K_D$ values, wherein $K_D$ is the equilibrium constant for the dissociation of an antigen with an antibody or fragment thereof. The smaller the $K_D$ value, the stronger the binding interaction between an antibody and its target antigen. For high throughput kinetic evaluation of IgGs, dissociation rate constants ($k_{off}$) were determined using the Biacore® instrument as described elsewhere herein.

In some embodiments, the IL-1RAcP antibodies or antigen binding fragments thereof of the disclosure may exhibit an off-rate ($k_{off}$) for IL-1RAcP of less than $5\times10^{-5}$ s$^{-1}$, less than $4\times10^{-5}$ s$^{-1}$, less than $3.5\times10^{-5}$ s$^{-1}$ when tested as a mAb against the human IL-1RAcP.

In some embodiments, the IL-1RAcP antibodies or antigen binding fragments thereof of the disclosure may exhibit a $K_D$ value (human IL-1RAcP) of less than $50\times10^{-12}$ M, less than $40\times10^{-9}$ M, less than $30\times10^{-9}$ M. In some embodiments, the IL-1RAcP antibodies or antigen binding fragments thereof of the disclosure exhibit a $K_D$ value less than $25\times10^{-9}$ M.

In some embodiments, the present disclosure provides the antibodies or antigen binding fragments disclosed in in Table 1, wherein said antibodies or antigen binding fragments can bind monovalent to human IL-1RAcP with a $K_D$ value of about less than $50\times10^{-12}$ M, less than $40\times10^{-9}$ M, less than $30\times10^{-9}$ M. In preferred embodiments, the IL-1RAcP antibodies or antigen binding fragments thereof of the disclosure exhibit a $K_D$ value less than $25\times10^{-9}$ M.

In some embodiments, the present disclosure provides antibodies or antigen binding fragments specific for IL-1RAcP, wherein said antibodies or antigen binding fragments have a monovalent affinity to IL-1RAcP as stated above and wherein said antibodies or antigen binding fragments in a bivalent format have an affinity to IL-1RAcP with a dissociation rate constant (KD) which is at least 2-fold, 5-fold, 10-fold, 100-fold, 1000-fold, 10000-fold, 100000-fold lower than the dissociation rate constant (KD) in a monovalent format.

Inhibition of Downstream Signalling

Upon binding of the cytokine to the primary cytokine receptor (IL-1 to IL-1R; IL-33 to ST2/IL-33R; IL-36α/IL-36β/IL-36γ to IL-1Rrp2/IL-36R) the affinity of the pre-formed complex to IL-1RAcP is elevated, promoting the recruiting of IL-1RAcP to form a heterotrimeric receptor-complex. The formation of the heterotrimeric signalling complex brings the intracellular TIR domains of IL-1R/ST2/IL-36R and IL-1RAcP in close proximity to each other allowing the recruitment of adaptor proteins like MyD88 for the formation of intracellular signalling complexes and the initiation of the signalling cascade.

In some embodiments, antibodies and antigen binding fragments of the disclosure bind to human IL-1RAcP and inhibit formation of the heterotrimeric receptor complex between the cytokines, the receptor for the specific cytokine and the IL-1RAcP. The cytokines and receptor are for example IL-1 to IL-1R; IL-33 to ST2/IL-33R; IL-36α/IL-36β/IL-36γ to IL-1Rrp2/IL-36R as described elsewhere. Inhibition of the receptor complex formation inhibits the signalling cascade.

The term "inhibition of IL-1RAcP signalling" means the inhibition of the signalling cascade from the heterotrimeric complexes, which are formed as described above. In some embodiments, the antibodies and antigen binding fragments of the disclosure bind to human IL-1RAcP and inhibit formation of the heterotrimeric receptor complex between the cytokines, the receptor for the specific cytokine and the IL-1RAcP thereby inhibiting the signalling from the individual cytokines and receptors by above 90%, above 95%, above 97%, above 98%, above 99% or 100%. In some embodiments the experiments are conducted at the $EC_{80}$ concentration of the cytokine.

In some embodiments, the antibodies and antigen binding fragments of the disclosure decreases an intracellular signalling by IL-1b with an IC50 of below 10 nM, below 5 nM, below 3 nM, or about 2 nM, or about 1 nM when measured in human dermal fibroblast as described in the present application.

In some embodiments the antibodies and antigen binding fragments of the disclosure decreases an intracellular signal by IL-1b with an IC50 of below 50 nM, below 40 nM, below 35 nM, or about 35 nM, or about 31 nM when measured in human keratinocytes.

In some embodiments the antibodies and antigen binding fragments of the disclosure decreases an intracellular signal by IL-1b with an IC50 of below 5 nM, below 4 nM, below 2 nM, or about 1.7 nM, or about 1.2 nM when measured in HPMC.

In some embodiments the antibodies and antigen binding fragments of the disclosure decreases an signal in human dermal fibroblasts by IL-36(alpha or beta and gamma) (0.06 nM) with an IC50 of below 1 nM, below 0.5 nM, below 0.3 nM, below 0.1 nM, below 0.05 nM, or about 0.036 to about 0.09 nM when measured in human dermal fibroblast as described in the present application.

In some embodiments the antibodies and antigen binding fragments of the disclosure decreases an signal in human dermal fibroblasts by IL-36β with an IC50 of below 1 nM, below 0.5 nM, below 0.3 nM, below 0.2 nM or about 0.094 to about 0.2 nM when measured in human keratinocytes as described in the present application.

In some embodiments the antibodies and antigen binding fragments of the disclosure decreases an signal by IL-33 in human PBMC with an IC50 of below (0.2 nM 149, 0.72 (1489) 5 nM, below 3 nM, below 2 nM, below 1 nM, or about 0.2-0.7 nM when measured in PBMC as described in the present application.

In some embodiments, the antibodies and antigen binding fragments of the disclosure binds to the soluble form of IL-1RAcP (sIL-1RAcP) and prevents signalling also from this variant of the IL-1RAcP as described in the present disclosure.

Cross-Reactivity

In certain embodiments, the antibodies or antigen binding fragments described herein that bind human IL-1RAcP may cross-react with one or more species homologs of IL-1RAcP, for example IL-1RAcP homologs of primate origin.

In some embodiments, the antibodies or antigen binding fragments of the present disclosure do not cross-react with murine IL-1RAcP. In some embodiments, the antibodies or antigen binding fragments may bind to one or more IL-1RAcP homologs of primate origin, for example IL-1RAcP proteins from Cynomolgus monkeys. The cross-reactivity with other species homologs can be particularly advantageous in the development and testing of therapeutic antibodies. For example, pre-clinical toxicology testing of therapeutic antibodies is frequently carried out in primate species including but not limited to Cynomolgus monkeys. Cross-reactivity with these species homologs can therefore be particularly advantageous for the development of antibodies as clinical candidates.

Polynucleotides Encoding IL-1RAcP Antibodies:

In one aspect, the present disclosure provides polynucleotide molecules encoding the IL-1RAcP antibodies of the disclosure or antigen binding fragments thereof, also expression vectors containing said nucleotide sequences of the disclosure operably linked to regulatory sequences which permit expression of the antibodies or antigen binding fragments thereof in a host cell or cell-free expression system, and a host cell or cell-free expression system containing this expression vector.

In one aspect, the present disclosure provides, the polynucleotide encoding the IL-1RAcP antibody of the disclosure may comprise one or more of the polynucleotide sequences shown as SEQ ID NOS: 21, 22, 25 and 26 which sequences encode VH or VL domains of IL-1RAcP antibodies.

In one aspect, the present disclosure provides, the polynucleotide encoding the IL-1RAcP antibody of the disclosure may comprise a variant sequence which encodes a functional VH or VL domain of an IL-1RAcP antibody, wherein said variant sequence exhibits at least 80%, 85%, 90%, 95%, 97% or 99% sequence identity when optimally aligned to any one of SEQ ID NOS: 21, 22, 25 and 26.

In this context, percent sequence identity between two polynucleotide sequences may be determined by comparing these two sequences aligned in an optimum manner and in which the polynucleotide sequence to be compared can comprise additions or deletions with respect to the reference sequence for an optimum alignment between these two sequences. The percentage of identity is calculated by determining the number of identical positions for which the nucleotide residue is identical between the two sequences, by dividing this number of identical positions by the total number of positions in the comparison window and by multiplying the result obtained by 100 in order to obtain the percentage of identity between these two sequences. For example, it is possible to use the BLAST program, "BLAST 2 sequences" (Tatusova et al., "Blast 2 sequences—a new tool for comparing protein and nucleotide sequences", FEMS Microbiol Lett. 174:247-250), the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

In one aspect, the present disclosure provides the heavy chain variable domain and the light chain variable domain of the IL-1RAcP antibodies or antigen-binding fragments thereof, encoded by a combination of first and second polynucleotide sequences, wherein the first and second polynucleotide sequences are selected from the following pairs:

(i) a first polynucleotide encoding a variable heavy chain domain comprising SEQ ID NO: 21 and a second polynucleotide encoding a variable light chain domain comprising SEQ ID NO: 22;

(ii) a first polynucleotide encoding a variable heavy chain domain comprising SEQ ID NO: 24 and a second polynucleotide encoding a variable light chain domain comprising SEQ ID NO: 25;

Polynucleotide molecules encoding the antibodies of the disclosure include, for example, recombinant DNA molecules. The terms "nucleic acid", "polynucleotide" or a "polynucleotide molecule" as used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the disclosure, nucleic acids or polynucleotides are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of an antibody according to the disclosure, a recombinant polynucleotide encoding it may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC® CRL 1651); human embryonic kidney line (293 or 293 cells subcloned for growth in suspension culture, Graham et al., J. Gen. Virol. 36:59 (1977)); baby hamster kidney cells (BHK, ATCC® CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); mouse myeloma cells SP2/0-AG14 (ATCC® CRL 1581; ATCC® CRL 8287) or NSO (HPA culture collections no. 85110503); monkey kidney cells (CV1 ATCC® CCL 70); African green monkey kidney cells (VERO-76, ATCC® CRL-1587); human cervical carcinoma cells (HELA, ATCC® CCL 2); canine kidney cells (MDCK, ATCC® CCL 34); buffalo rat liver cells (BRL 3A, ATCC® CRL 1442); human lung cells (W138, ATCC® CCL 75); human liver cells (Hep G2, HB 8065); mouse mammary tumor (MMT 060562, ATCC® CCL51); TRI cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art. It should be noted that the term "host cell" generally refers to a cultured cell line. Whole human beings into which an expression vector encoding an antigen binding polypeptide according to the disclosure has been introduced are explicitly excluded from the definition of a "host cell".

Antibody Production

In one aspect, the present disclosure provides a method of producing antibodies of the disclosure which comprises culturing a host cell (or cell free expression system) containing polynucleotide (e.g. an expression vector) encoding an antibody or antigen-binding fragment of the present disclosure under conditions which permit expression of the antibody, and recovering the expressed antibody. This process can be used for large scale production of antibodies, including IL-1RAcP antibodies according to the disclosure, including monoclonal antibodies intended for human therapeutic use. Suitable vectors, cell lines and production processes for large scale manufacture of recombinant antibodies suitable for in vivo therapeutic use are generally available in the art and will be well known to the skilled person.

Therapeutic Utility of IL-1RAcP Antibodies:

In one aspect, the present disclosure provides the IL-1RAcP antibodies provided herein can be used as medicaments, particularly for use in the treatment or prophylaxis of disorders or conditions relating to IL-1RAcP signalling such as hidradenitis suppurativa, palmoplantar pustulosis, pyoderma gangrenosum, systemic sclerosis, severe Acne and atopic dermatitis. Also diseases such as Asthma, graft versus host disease (GVHD), Psoriatic Arthritis, Juvenile Psoriasis, Rheumatoid Arthritis, Sjögrens syndrome, myocarditis, systemic sclerosis, ulcerative colitis and Chronic Obstructive Pulmonary Disease, Bullous Pemphigoid, Dermatomyositis, Allergic Contact Dermatitis, general pustular psoriasis, Juvenile Psoriasis, Vitiligo, Pemphigus Vulgaris, Psoriasis, Asthma, Epidermolysis Bullosa, Cryopyrin-associated periodic syndrome (inflammasome driven), Systemic Juvenile Idiopathic Arthritis, Hyper IgD syndrome, Behçet's disease, Acne vulgaris, Ulcerative Colitis, Gout, Schnitzler's syndrome, adult-onset Still's disease, Netherton syndrome, Aggressive periodontitis cases, Liver diseases, Endometriosis and steroid-sensitive nephrotic syndrome are connected to the present target.

In one aspect, the present disclosure provides an anti-IL-1RAcP antibody or antigen binding fragment thereof for use in treating an IL-1RAcP-associated disease or condition, wherein the anti-IL-1RAcP antibody or antigen binding fragment comprises complementarity determining regions (CDRs) with the amino acid sequences of:
  i. SEQ ID NO: 4 for CDR1 of the heavy chain;
  ii. SEQ ID NO: 5 for CDR2 of the heavy chain;
  iii. SEQ ID NO: 6 for CDR3 of the heavy chain;
  iv. SEQ ID NO: 1 for CDR1 of the light chain;
  v. SEQ ID NO: 2 for CDR2 of the light chain; and
  vi. SEQ ID NO: 3 for CDR3 of the light chain.

In one aspect, the present disclosure provides an anti-IL-1RAcP antibody or antigen binding fragment thereof for use in treating an IL-1RAcP-associated disease, wherein the anti-IL-1RAcP antibody or antigen binding fragment comprises (i) a heavy chain variable region of the amino acid sequence of SEQ ID NO: 7, and (ii) a light chain variable region of the amino acid sequence of SEQ ID NO: 8.

In one aspect, the present disclosure provides an anti-IL-1RAcP antibody or antigen binding fragment thereof for use in treating an IL-1RAcP-associated disease, wherein the anti-IL-1RAcP antibody or antigen binding fragment comprises
  (ii) a VH comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 7
  and
  (ii) a $V_L$ comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 8

In one aspect, the present disclosure provides an anti-IL-1RAcP antibody or antigen binding fragment thereof for use in treating an IL-1RAcP-associated disease, wherein the anti-IL-1RAcP antibody consists of two heavy and two light chains, wherein each heavy chain has the amino acid sequence of SEQ ID NO: 17, and wherein each light chain has the amino acid sequence of SEQ ID NO: 18.

In one aspect, the present disclosure provides an anti-IL-1RAcP antibody or antigen binding fragment thereof for use in treating an IL-1RAcP-associated disease, wherein the anti-IL-1RAcP antibody consists of two heavy and two light chains, comprising
  (ii) a VH comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 17 and (ii) a VL comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 18

In one aspect, the present disclosure provides an anti-IL-1RAcP antibody or antigen binding fragment thereof for use in treating an IL-1RAcP-associated disease, wherein the anti-IL-1RAcP antibody or antigen binding fragment comprises complementarity determining regions (CDRs) with the amino acid sequences of:
i. SEQ ID NO: 12 for CDR1 of the heavy chain;
ii. SEQ ID NO: 13 for CDR2 of the heavy chain;
iii. SEQ ID NO: 14 for CDR3 of the heavy chain;
iv. SEQ ID NO: 9 for CDR1 of the light chain;
v. SEQ ID NO: 10 for CDR2 of the light chain; and
vi. SEQ ID NO: 11 for CDR3 of the light chain.

In one aspect, the present disclosure provides an anti-IL-TRAcP antibody or antigen binding fragment thereof for use in treating an IL-1RAcP-associated disease, wherein the anti-IL-1RAcP antibody or antigen binding fragment comprises (i) a heavy chain variable region of the amino acid sequence of SEQ ID NO: 15, and (ii) a light chain variable region of the amino acid sequence of SEQ ID NO: 16.

In one aspect, the present disclosure provides an anti-IL-TRAcP antibody or antigen binding fragment thereof for use in treating an IL-1RAcP-associated disease, wherein the anti-IL-1RAcP antibody or antigen binding fragment comprises
(i) a VH comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 15
and
(ii) a VL comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 16

In one aspect, the present disclosure provides an anti-IL-TRAcP antibody or antigen binding fragment thereof for use in treating an IL-1RAcP-associated disease, wherein the anti-IL-1RAcP antibody or antigen binding fragment comprising a heavy chain having the amino acid sequence of SEQ ID NO: 19, and a light chain having the amino acid sequence of SEQ ID NO: 20.

In one aspect, the present disclosure provides an anti-IL-1RAcP antibody or antigen binding fragment thereof for use in treating an IL-1RAcP-associated disease, wherein the anti-IL-1RAcP antibody or antigen binding fragment comprising
(i) a VH comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 19
and
(ii) a $V_L$ comprising or consisting of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to the amino acid sequence of SEQ ID NO: 20

In preferred embodiments, the subject is a human subject.

The term "treating" or "treatment" means slowing, interrupting, arresting, controlling, stopping, reducing severity of a symptom, disorder, condition or disease, but does not necessarily involve a total elimination of all disease-related symptoms, conditions or disorders. The term "prophylaxis" means preventing the onset of a disorder, condition or disease or preventing the onset of symptoms associated with a disorder, condition or disease. In certain embodiments, provided herein are methods of treating skin inflammatory diseases. In certain embodiments, provided herein are methods of treating skin inflammatory diseases selected from psoriasis, psoriatic arthritis, contact dermatitis or atopic dermatitis in a human subject. The methods comprise administering to a patient in need thereof a therapeutically effective amount of any of the IL-1RAcP antibodies or antigen binding fragments as defined elsewhere herein. All embodiments of the IL-1RAcP antibodies of antigen binding fragments as described herein are equally applicable to the methods of treatment of the present disclosure.

For human therapeutic use the IL-1RAcP antibodies described herein may be administered to a human subject in need of treatment in an "effective amount". The term "effective amount" refers to the amount or dose of an IL-1RAcP antibody which, upon single or multiple dose administration to a human patient, provides therapeutic efficacy in the treatment of disease. Therapeutically effective amounts of the IL-1RAcP antibody can comprise an amount in the range of from about 0.1 mg/kg to about 20 mg/kg per single dose. The amount of antibody administered at any given time point may be varied so that optimal amounts of IL-1RAcP antibody, whether employed alone or in combination with any other therapeutic agent, are administered during the course of treatment.

It is also contemplated to administer the IL-1RAcP antibodies described herein, or pharmaceutical compositions comprising such antibodies, in combination or in conjunction with any other suitable treatment for the diseases identified above.

Pharmaceutical Compositions

The scope of the disclosure includes pharmaceutical compositions, containing one or a combination of IL-1RAcP antibodies of the disclosure, or antigen-binding fragments thereof, formulated with one or more a pharmaceutically acceptable carriers or excipients. Such compositions may include one or a combination of (e.g., two or more different) IL-1RAcP antibodies. Techniques for formulating monoclonal antibodies for human therapeutic use are well known in the art and are reviewed, for example, in Wang et al., Journal of Pharmaceutical Sciences, Vol. 96, pp 1-26, 2007, the contents of which are incorporated herein in their entirety.

In certain embodiments, the pharmaceutical compositions are formulated for administration to a subject via any suitable route of administration including but not limited to intramuscular, intravenous, intradermal, intraperitoneal injection, subcutaneous, epidural, nasal, oral, rectal, topical, inhalational, buccal (e.g., sublingual), and transdermal administration. In preferred embodiments, the composition is formulated for subcutaneous administration.

EXAMPLES

Antibodies from prior art are included in some of the below experiments. The antibodies of the prior art are the following: the mouse antibodies 4G9 (WO2014100772) and CAN01, CAN03 and CAN04 (WO2016020502); the rabbit antibody 1A05 (also known as P013.S.01.B.A05; WO2016207304) and the human antibody h11C5 YKD (WO2020037154). Modifications were made to these antibodies. In particular, for the mouse and rabbit antibodies, the VH and VL domains were expressed in a chimeric antibody containing human IgG1κ constant regions. The human IgG1 constant region of the chimeric antibody contains residues AEASS at positions 234, 235, 237, 330 and 331, respectively, which reduce effector function (e.g. ADCC). For h11C5 YKD, the variable domains were expressed in antibody containing the same modified IgG1κ constant regions as the chimeric antibodies.

The sequences of the heavy and light chains of the versions of these antibodies that were used in the Examples are summarised below.

Reference antibodies as applied in the examples:

| Reference antibody | Heavy chain SEQ ID NO | Light chain SEQ ID NO |
| --- | --- | --- |
| R001028 (4G9) | 41 | 42 |
| R001029 (CAN01) | 43 | 44 |
| R001030 (CAN03) | 47 | 48 |
| R001031 (CAN04) | 51 | 52 |
| R001032 (1A05) | 35 | 36 |
| h11C5 YKD | 31 | 32 |

Experimental:

Generation of antigen, Fab fragments and antibodies: Amino acid sequences of IL-1RAcP from different species (human, cynomolgus and mouse) were aligned. DNA templates of the coding sequences were cloned in frame with a N- or C-terminal avi-His tag, with a C-terminal Flag-chLys-avi tag, with a C-terminal IgG Fc-tag and tagless, into a pMAX expression vector, which is a modified expression vector based on pcDNA3.1 (Thermo Fisher). The recombinant proteins were expressed in HEK293-6E or HKB11 cells. HEK293-6E cells were transiently transfected one day post seeding with a commercially available transfection reagent according to the manufacturer's instructions. The cells were cultured for three days and the conditioned cell culture supernatant was harvested by centrifugation followed by sterile filtration (0.22 pm). Stable HKB11 #52 pools were generated by transfection of cells followed by selection with 800 μg/mL G418 (Thermo Scientific). Expression of antigens from stable pools was done for 4 days post seeding. The conditioned cell culture supernatant was harvested by centrifugation followed by sterile filtration (0.22 pm). Antigens were purified by the appropriate method and columns dependent on the tagged construct. Target biotinylation were performed either in vivo by transient co-expression of a BirA encoding pMAX expression vector or in vitro by biotinylation using the BirA Kit followed by preparative SEC using a Superdex 200 16/60 column (GE Healthcare).

IL-1RAcP Overexpressing Cell Line Generation:

Plasmid used: The pOG44 plasmid (encoding of recombinase) and the pcDNA5/FRT/TO_human IL-1RAcP and cyno IL-1RAcP vector are co-transfected into the parental FIp-In CHO cell line. Upon co-transfection, the FIp recombinase expressed from pOG44 mediates a homologous recombination event between the FRT sites (integrated into the genome and on pcDNA5 plasmid) so that the pcDNA5/FRT/TO_human IL-1RAcP/cyno IL-1RAcP construct is inserted into the genome at the integrated FRT site. Insertion of pcDNA5/FRT/TO_hIL-1RAcP/cyno IL-1RAcP into the genome at the FRT site brings the SV40 promoter and the ATG initiation codon (from pFRT/lacZeo) into proximity, frame with the Hygromycin B resistance gene and inactivates the lacZ-Zeocin fusion gene.

Transfection: After reaching approximately 80-90% confluency, cells were washed once with pre-warmed PBS in order to remove excess medium and serum. Accutase (Gibco #A11105-01) was added in an appropriate amount and incubated at 37° C. for 3-5 minutes. Cells were harvested in full growth medium and cell number was determined using a Casy Cell counter. Subsequently, cells were re-suspended to a concentration of $1.5 \times 10^{\wedge}5$ cells/ml in full growth medium and 2 ml of cell solution/well was transferred to a 6-well plate.

After incubation over night at standard cell culture conditions, transfection of the cells was performed as follows. DNA (pcDNA5/FRT/TO_IL-1RAcP and pOG44) was mixed with lipofectamine in OptiMEM medium and incubated for 5 min at RT. Subsequently, the pre-incubated transfection reagents were added to the cells (gently mixed after addition). After incubation of 5-6 hours, medium was replaced with fresh full growth medium in order to remove transfection reagents.

24 hours after transfection cells were washed once with pre-warmed PBS and cells were detached according to the previously described procedure. Cells were seeded in flasks in full growth medium containing Hygromycin B (Invitrogen #10687-010).

In order to ensure expression and surface presentation of the stable CHO FIpIn clones, cells were analysed for receptor surface expression using FACS Generation of Phage Display Maturation Libraries:

The cloning of the maturation libraries was performed in the CysDisplay™ vector encoding for the parental Fab fragments. If not already present in the CysDisplay™ vector, the DNA sequences encoding for the parental Fab fragments were transferred into the respective vector via restriction digest and ligation prior to library cloning.

To increase affinity and biological activity and to reduce non-specificity of selected antibody candidates, CDR-L3 and CDR-H1/CDR-H2 regions were optimized in parallel using diversified Ylanthia® maturation modules (YMM) that were generated previously with the Slonomics® technology (van den Brulle et al. 2008).

The cloning of the maturation libraries was performed in the CysDisplay™ vector encoding for the parental Fab fragments.

The generation of the maturation libraries was performed for each maturation candidate individually or a set of different parental antibodies was pooled prior library generation.

In order to monitor the cloning efficiency, the parental CDR-L3 is replaced by a MBP-stuffer, before the diversified LCDR-L3 YMM is inserted. Digested vector fragments were ligated with a 2-fold molar excess of the insert fragment carrying the diversified CDR-L3s. The same procedure was applied for diversification of CDRH-1 & CDR-H2.

Ligation mixtures were electroporated in E. coli MC1061F' cells yielding in $>10^8$ independent colonies. Amplification of the library was performed as described in the literature (Tiller et al. 2013). For quality control, approx. 10-20 single clones per library were randomly picked and Sanger sequenced.

Subcloning into IgG & FabCys Expression Vector

For full length IgG or monovalent FabCys expression in HEK-293 or CHO-3E7 cells, selected candidates or candidate pools were cloned into the respective expression vector, comprising the features/tags desired.

Subcloning was performed as a two-step method for a convenient and efficient conversion of a large amount of sequence-unique Fab clones into the IgG format.

Ylanthia® YCLONE®

In a first cloning step, a eukaryotic expression cassette was introduced into the display vector or the vector for Fab expression in *E. coli* via KpnI|NheI digestion and subsequent ligation.

This was followed by a second cloning step, in which the Fab pools containing the expression cassette were digested using NdeI|XhoI and subsequently cloned into the acceptor vector for expression in mammalian cells.

Ylanthia® AmplYFast®

In a first step, kappa or lambda Fab-FH plasmid DNA were amplified via PCR with one biotinylated primer and one non-biotinylated primer, which bind within the bacterial CL and phoA leader region. The amplified product was bound on streptavidin beads and digested with NheI, washed and then digested again with KpnI resulting in the release of the purified vector backbone into the supernatant, now lacking the bacterial constant light chain region (CL) and the phoA heavy chain leader. Then a kappa or lambda specific eukaryotic pYMin expression cassette was cloned into the vector backbone carrying the mammalian CL, polyA site, CMV promotor and mammalian heavy chain leader sequence.

In a second step, the generated Fab encoding insert was re-amplified by PCR with one biotinylated primer and one non-biotinylated primer, which bind within the bacterial ompA leader and CH1 region. The amplified PCR product was again bound on streptavidin beads, digested with XhoI, washed and digested with NdeI resulting in the release of the purified insert into the supernatant. In a final step, inserts were cloned into the acceptor vector for expression in mammalian cells.

After transformation of *E. coli* XL-1 blue cells, single clones were quality controlled via colony PCR and sequencing of the whole insert region.

FAB and IGG Production
Production in *E. coli*
Generation of Fab Containing Crude Bacterial Lysates 96-well/384-well microtiter plates pre-filled with growth medium (2×YT containing chloramphenicol, IPTG and low glucose) were inoculated using glycerol stocks from masterplates. Plates were incubated at 37° C. for bacterial outgrowth and shaken overnight at 22° C. for Fab expression. The next day expression cultures were lysed by addition of BEL buffer containing borate buffer, EDTA and lysozyme. Depending on the selected plate format and application, volumes were adjusted and the protocol for blocking was adapted accordingly. EDTA was omitted if lysates were used for sensitive cell screenings.

Production of IgG
Advanced Micro Scale Production of IgG

HEK293-6E cells were transiently transfected with mammalian expression vector pYMex10_h_IgG1f_AEASS encoding both heavy and light chains of the respective human IgGf_AEASS antibodies. Transiently produced antibodies were secreted into the cell suspension. Cell culture supernatants were harvested 7 days post transfection.

Purification of antibodies form clarified cell culture supernatants was performed via Protein A affinity chromatography (RoboColumns (Opus) with MabSelect SURE|GE Healthcare) using a liquid handling station. If not stated otherwise, samples remained in neutralized elution buffer (NaPS: 137 mM NaPhosphate, 81 mM NaCl, pH 7). Samples were sterile filtered (0.2 µm pore size).

Protein concentrations were determined by UV-spectrophotometry and purities of IgG were analysed under denaturing, reducing conditions using CE-SDS (LabChip GXII|Perkin Elmer|USA). UHP-SEC was performed to analyze IgG preparations in native state.

Identification of IL-1RAcP binders: To identify IL-1RAcP-specific antibodies different panning strategies were used. Each panning strategy comprised at least 3 individual rounds of panning against the respective antigens including human IL-1RAcP (SEQ ID NO: 57), CHO cells expressing human IL-1RAcP, cynomolgus IL-1RAcP and cells expressing cynomolgus IL-1RAcP and mouse IL-1RAcP.

The isolated clones identified were maturated, engineered and/or germlined in order to increase affinity and/or functionality. Thereafter several hundred clones were screened and functionality was rigorously tested in in vitro assays comprising e.g. the evaluation of binding to human, cynomolgus monkey and mouse IL-1RAcP via SET, identification of the binding to domain 1, 2, or 3 of IL-1RAcP, and functional inhibition of IL-1, IL-36 and IL-33 signaling (primary dermal human fibroblasts, human PBMCs and cynomolgus fibroblasts as well as primary human dermal keratinocytes).

Example 1 Binding

The ELISA settings, antigens have been captured to plates via a tag-specific antibody coated on microtiter plates (e.g. anti-Fc, anti-His) or biotinylated antigens were bound to NeutrAvidin plates. Bound antibodies were detected using respective alkaline-phosphatase (AP) coupled secondary antibodies in combination with 'AttoPhos' fluorescence substrate. Multiple washing steps have been performed in between individual assay steps.

Figure 1B:
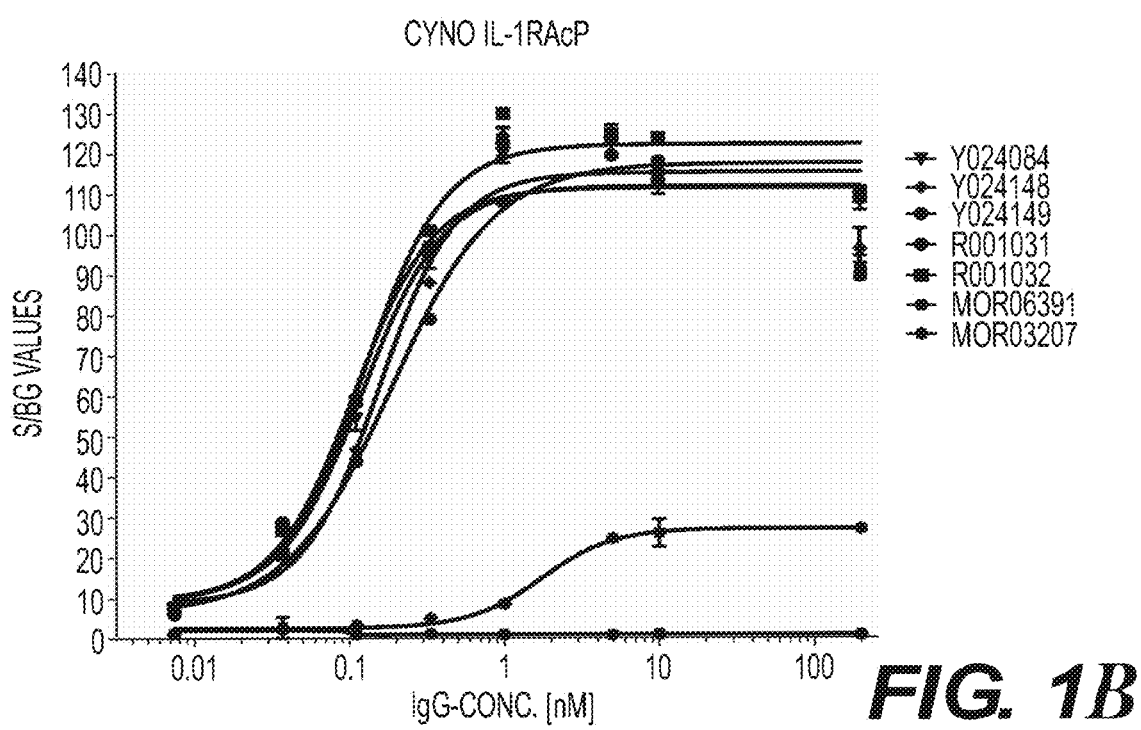
FIG. 1B: Various concentrations of the antibodies in the IgG1f_AEASS format were tested for binding to cynomolgus (AG-12211) IL-1RAcP (IL-1RAP), by ELISA

FIG. 1A: Various concentrations of the antibodies in the IgG1f_AEASS format were tested for binding to human (AG-12210) IL-1RAcP, by ELISA. MOR06391 (anti-GFP) was used as an IL-1RAcP non-specific isotype control. MOR03207 (anti-Lysozyme), due to its binding to the chLys Tag of the antigens, served as a positive control FIG. 1B: Various concentrations of the antibodies in the IgG1f_AEASS format were tested for binding to cynomolgus (AG-12211) IL-1RAcP, by ELISA. MOR06391 (anti-GFP) was used as an IL-1RAcP non-specific isotype control. MOR03207 (anti-Lysozyme), due to its binding to the chLys Tag of the antigens, served as a positive control FIG. 1C: Various concentrations of the antibodies in the IgG1f_AEASS format were tested for binding to mouse (AG-12212) IL-1RAcP were assessed in Fc-capture mode of the IgGs. MOR06391 (anti-GFP) was used as an IL-1RAcP non-specific isotype control. MOR03207 (anti-Lysozyme), due to its binding to the chLys Tag of the antigens, served as a positive control.

FIG. 2A: Various concentrations of the antibodies in the IgG1f_AEASS format were tested for binding to human IL1RAcP domain 1 (AG-12335). All were assessed with direct coating of the antigen. MOR06391 (anti-GFP) served as an IL-1RAcP non-specific isotype control. An anti-His antibody served as positive control.

FIG. 2B: Various concentrations of the antibodies in the IgG1f_AEASS format were tested for binding to human IL1RAcP domain 1/2 (AG-12337). All were assessed with direct coating of the antigen. MOR06391 (anti-GFP) served as an IL-1RAcP non-specific isotype control. An anti-His antibody served as positive control.

FIG. 2C: Various concentrations of the antibodies in the IgG1f_AEASS format were tested for binding to human IL1RAcP domain 3 (AG-12127). All were assessed with direct coating of the antigen. MOR06391 (anti-GFP) served as an IL-1RAcP non-specific isotype control. An anti-His antibody served as positive control.

Example 2 Method for ELISA

Antigens were immobilized on microtiter plates. Plates were blocked and incubated with antibodies such as Fab containing crude *E. coli* lysates or purified Fab or IgG samples. Bound antibodies were detected using respective alkaline-phosphatase (AP) coupled secondary antibodies in combination with 'AttoPhos' (from Sigma Aldridge) fluorescence substrate. Multiple washing steps have been performed in between individual assay steps.

Example 3 CHO Cells Overexpressing

Cell suspensions were transferred into microtiter plates and antibody samples were added followed by subsequent incubation of plates at 4° C. Sample volume and cell-number are adjusted to plate type used. Following incubation, cells were spun down and washed with FACS buffer. Fluorophore-conjugated secondary reagents were used for detection of bound antibodies. Plates were measured using the BD FACS Array, OLS NovoCyte/Quanteon™ or Intellicyt HTFC/iQue® System and data was analysed using FlowJo™.

The HTFC/iQue Screening System was also used for evaluation of binding to multiple target cell lines or evaluation of unwanted/unspecific binding in parallel=multiplexing. Different cell populations could be distinguished by pre-labeling with distinct amounts of fluorescent dyes such as Calcein or Cell-Tracker Green, establishing a unique signature of fluorescence intensity for each cell population=fluorescence barcoding. The color-coded cell lines were then physically combined and mixed together with antibodies to be tested. Individual cell-lines could be identified via the fluorescence of the respective cell-line that had been pre-labeled. Crude bacterial cell lysates were combined with cells and incubated for 1 h at room temperature in the dark, shaking gently. Fluorescence measurement was performed with the IntelliCyt HTFC/iQue® device. In between incubation steps, no washing was required.

Raw data were evaluated with the help of the "iQue Forecyt®" software. After data acquisition, the cell lines from each sample could be identified according to their fluorescence signature and individually evaluated for antibody binding. Staining-conditions for each cell line were optimized in order to find an assay set-up allowing the separation of distinct cell lines.

The antibodies were tested for binding to human and cynomolgus IL-1RAcP overexpressing CHO cells—side by side with the two reference antibodies CAN04 and 1A05. All antibodies and the two reference antibodies displayed binding to human and cynomolgus IL-1RAcP expressed on CHO cells. No signal was detected when titrating the same antibody concentrations on parental CHO cells, expressing neither human nor cynomolgus IL-RAcP on the surface.

Example 4 Binding to Primary Human Dermal Fibroblasts

Cell suspensions were transferred into microtiter plates and antibody samples were added followed by subsequent incubation of plates at 4° C. for 3 hours. Following incubation, cells were washed several time with FACS buffer.

AffiniPure Goat Anti-Human IgG, Fcγ fragment specific (cat #109-135-098 from Jackson ImmunoResearch) was used for detection of bound antibodies. The plates were incubated with anti-goat secondary antibody for at 4° C. for 30 minutes. Plates were measured using the BD Fortessa X 20 System and data was analysed using FlowJo.

The results show that antibodies displayed binding to the dermal fibroblasts although to different extent.

Example 5 Affinity Using SPR

On a CM5 chip (Biacore®; Cytiva Life Sciences) an appropriate capture ligand (e.g. anti-antigen tag) was covalently immobilized using EDC/NHS chemistry. Fab fractions at e.g. 5 different concentrations (serial dilution) were used as analytes in solution during kinetic experiments. After each cycle, the sensor surface was regenerated to remove bound antigen/Fab complexes, while maintaining the integrity of the capture surface. A blank injection of running buffer was used for double referencing, i.e. to compensate for effects such as dissociation from the underlying capture surface.

For the reversible capture of biotinylated antigen, an SPR-sensor bearing single-stranded DNA was preloaded with capture reagent, i.e. streptavidin covalently modified with the corresponding ssDNA counterstrand (biotin CAPture kit, Cat. 28920234, Cytiva). Approximately 3000 RU capture reagent was bound. This surface was used to load biotinylated antigen to generate a low-density surface for subsequent kinetic characterization (approx. 60-100 RU antigen loaded). Fab fragments were injected in a single cycle kinetics experiment, i.e. 5 concentrations from 160 pM to 40 nM (4-fold dilution series) or 0.5 to 20 nM (2.5-fold dilution series) were injected with intermitting short dissociations. After injecting the last and highest analyte concentration, a long dissociation phase was recorded. Association time for each analyte concentration was 180 s, short intermittent dissociations were observed for 60 s, long final dissociation was recorded for 30 min. A blank injection of assay buffer (HBS-EP+) following the same injection pattern as described above was recorded and subtracted from specific sensorgrams during analysis (double referencing). At the end of each cycle, the sensor was regenerated with one 120 s injection of 6 M guanidine hydrochloride in 250 mM NaOH, which completely removed capture reagent with loaded biotinylated antigen and bound Fab fragments. The obtained sensorgrams were fitted to a monovalent binding model using Biacore® Insight Evaluation Software. The obtained values for rate constants $k_{on}$ and $k_{off}$ were used to calculate $K_D$.

Sensorgrams were evaluated with the corresponding instrument's evaluation software, i.e. Biacore® T200 Evaluation Software 3.x (Biacore®; Cytiva Life Sciences), Biacore® Insight Evaluation (Biacore® 8K+; Cytiva Life Sciences) or forteBIO Octet Data Analysis (fortéBIO|Pall corp.), respectively. All sensorgrams were fitted to a 1:1 binding model to determine $k_{on}$ and $k_{off}$ rate constants, which were used to calculate $K_D$ Affinity determination of antibodies of the disclosure in the FabCys-AviHis format via Biacore® (SPR) in comparison to the reference antibodies CAN04 (R001031) and 1A05 (R001032). Biotinylated human IL-1RAcP (AG-12210) was used for the interaction analysis. Data in Table for human IL-1RAcP and table for cynomolgus IL-1RAcP

TABLE 5-1

| Antibody ID | Interaction partner | $k_{on}$ | $k_{off}$ | $K_D$ | Comment | KD restriction (yes/no) |
|---|---|---|---|---|---|---|
| Y024084_h_FabCys-AviH | hIL-1RAP (1-367)_F-chLys_Avi-bio | 2.01E+06 | 1.43E-04 | 71 | | no |
| Y024148_h_FabCys-AviH | hIL-1RAP (1-367)_F-chLys_Avi-bio | 1.10E+06 | 2.01E-05 | 18 | | no |
| Y024149_h_FabCys-AviH | hIL-1RAP (1-367)F-chLys_Avi-bio | 1.24E+06 | 3.06E-05 | 25 | | no |
| CAN04_h_FabCys-AviH | hIL-1RAP (1-367)_F-chLys_Avi-bio | 3.37E+05 | 5.64E-05 | 167 | | no |
| 1A05_rbh_FabCys-AviH | hIL-1RAP (1-367)_F-chLys_Avi-bio | 7.77E+05 | 1.71E-04 | 221 | | no |

Affinity determination of antibodies of the disclosure in the FabCys-AviHis format via Biacore® (SPR) in comparison to the reference antibodies CAN04 (R001031) and 1A05 (R001032). Biotinylated cynomolgus IL-1RAcP (AG-12211) was used for the interaction analysis.

TABLE 5-2

| Antibody ID | Interaction partner | $k_{on}$ | $k_{off}$ | $K_D$ | Comment | KD restriction (yes/no) |
|---|---|---|---|---|---|---|
| Y024084_h_FabCys-AviH | cyIL-1RAP (1-367)_F-chLys_Avi-bio | 1.65E+06 | 7.15E-05 | 43 | | no |
| Y024148_h_FabCys-AviH | cyIL-1RAP (1-367)_F-chLys_Avi-bio | 1.64E+06 | 1.26E-05 | 8 | $K_{off}$ approaching assay limit | no |
| Y024149_h_FabCys-AviH | cyIL-1RAP (1-367)_F-chLys_Avi-bio | 1.74E+06 | 1.00E-05 | 6 | $K_{off}$ at assay limit | no |
| CAN04_h_FabCys-AviH | cyIL-1RAP (1-367)_F-chLys_Avi-bio | 3.08E+05 | 3.95E-05 | 128 | | no |
| 1A05_rbh_FabCys-AviH | cyIL-1RAP (1-367)_F-chLys_Avi-bio | 8.57E+05 | 1.57E-04 | 184 | | no |

Example 6 Affinity by SET

For $K_D$ determinations, monomer fractions of antibody protein (Fab|IgG) were used containing at least 90% monomer content, as analysed by analytical SEC. Affinity determination in solution was basically performed as described in the literature (Friguet et al. 1985). In order to improve the sensitivity and accuracy of the SET method, it was transferred from classical ELISA to ECL-based technology (Haenel et al. 2005). 1 mg/mL goat-anti-human (Fab)₂ fragment specific antibodies (Dianova) were labeled with MSD Sulfo-TAG™ NHS-Ester (Meso Scale Diagnostics; $C_{43}H_{41}N_7O_{16}RuS_4$) according to the manufacturer's instructions. The experiments were carried out in polypropylene microtiter plates and PBS (GIBCO 14190|pH 7.0-7.2) containing 0.5% BSA and 0.02% Tween 20™ (polysorbate 20) as assay buffer. Serial dilutions of unlabeled antigen were prepared, starting with a concentration at least 10 times higher than the expected $K_D$. Wells without antigen were used to determine $B_{max}$ values; wells containing only assay buffer were used to determine background. After addition of appropriate amount of binder (antibody concentration similar to or below the expected $K_D$, 60 µL/well final volume), the mixture was incubated over night at RT. MSD plates were coated with antigen on standard plates (30 µL per well). After washing the plate with PBS with 0.05% Tween 20™ (polysorbate 20), the equilibrated samples were transferred to the plates and incubated for 20 min. Following incubation, 30 µL per well of the MSD SulfoTAG™ NHS-Ester ($C_{43}H_{41}N_7O_{16}RuS_4$) labeled detection antibody (anti-human (Fab)₂|final dilution typically 1:2,000) was added to the washed MSD plate and incubated for 30 min at RT on an Eppendorf shaker (700 rpm). After washing the MSD plate and adding 30 µL/well MSD Read Buffer T with surfactant, electrochemiluminescence signals were detected using a MESO SECTOR S 600 (Meso Scale Diagnostics).

The data was evaluated with XLfit (IDBS) software applying customized fitting models. For $K_D$ determination of Fab molecules the fit model according to Haenel et al. 2005, modified according to Abraham et al. was used. For $K_D$ determination of IgG molecules and monomeric antigens a fit model for IgG was used, modified according to Piehler et al. 1997, for equations see also Della Ducata et. al. 2005.

Results for human IL-1RAcP in Table 6-1 and for cynomolgus in Table 6-2

TABLE 6-1

| Antibody ID | Interaction partner | KD [pM] | confidence interval 95%[pM] | $r^2$ linear correlation coefficient | Comment | KD restriction (yes/no) |
|---|---|---|---|---|---|---|
| Y024149_h_IgG1f_AEASS | hIL-1RAP(1-367)-_F-_chLys_Avi | 3 | 1 | 0.98 | fit ok | no |
| Y024148_h_IgG1f_AEASS | hIL-1RAP(1-367)-_F-_chLys_Avi | 2 | 0 | 0.99 | fit ok | no |
| Y024084_h_IgG1f_AEASS | hIL-1RAP(1-367)-_F-_chLys_Avi | 4 | 1 | 0.99 | fit ok | no |
| H11C5_h_IgG1f_AEASS | hIL-1RAP(1-367)-_F-_chLys_Avi | 3 | 1 | 0.97 | fit ok | no |
| 1A05_rbh_IgG1f_AEASS | hIL-1RAP(1-367)-_F-_chLys_Avi | 11 | 4 | 0.97 | fit ok | no |
| CAN04_h_IgG1f_AEASS | hIL-1RAP(1-367)-_F-_chLys_Avi | 21 | 4 | 0.99 | fit ok | no |

TABLE 6-2

| Antibody ID | Interaction partner | KD [pM] | confidence interval 95%[pM] | $r^2$ linear correlation coefficient | Comment | KD restriction (yes/no) |
|---|---|---|---|---|---|---|
| Y024149_h_IgG1f_AEASS | hIL-1RAP(1-367)-_F-_chLys_Avi | 1 | 0 | 0.99 | fit ok | no |
| Y024148_h_IgG1f_AEASS | hIL-1RAP(1-367)-_F-_chLys_Avi | 1 | 0 | 0.98 | fit ok | no |
| Y024084_h_IgG1f_AEASS | hIL-1RAP(1-367)-_F-_chLys_Avi | 4 | 1 | 0.99 | fit ok | no |
| H11C5_h_IgG1f_AEASS | hIL-1RAP(1-367)-_F-_chLys_Avi | 3 | 1 | 0.98 | fit ok | no |
| 1A05_rbh_IgG1f_AEASS | hIL-1RAP(1-367)-_F-_chLys_Avi | 15 | 3 | 0.99 | fit ok | no |
| CAN04_h_IgG1f_AEASS | hIL-1RAP(1-367)-_F-_chLys_Avi | 16 | 3 | 0.99 | fit ok | no |

Example 7 Epitopes

Epitope binning experiments are crucial in order to retain diversity in the selection of antibodies in terms of epitope specificity but also for differentiation to the reference antibodies. The antibodies of the disclosure are utilised in the FabCys-AviHis format. The experimental setup is as follows: All antibodies are coated directly on a plate in individual wells. After blocking, a preformed complex of biotinylated IL1RAP and the second antibody as Fab is added in every possible combination of antibodies (coated on the surface and in solution). Detection happened via biotin on the IL-1RAcP protein. Utilizing Fabs instead of IgGs adds value to the experiment as steric hindrance might be reduced resulting in a better resolution of the epitope bins.

ELISA-based epitope binning is a method giving only a rough estimation of epitope differentiation. The method has its limitations in resolution due to steric hindrance of the antibodies. If two antibodies are assigned to the same epitope bin, more precise methods have to be used in order to define the specific epitope of an antibody and to allow further resolution of the epitopes.

In case the antibodies compete with each other for binding to the antigen, the detectable signal drops to zero as the antigen is not able to bind anymore to the coated antibody as the binding site is already blocked (with increasing antibody concentrations and a fixed antigen concentration). In case the two antibodies do not compete with each other, the detectable signal remains unaltered (in comparison to antigen only or IL1RAcP non-specific isotype control) as both antibodies are able to bind at the same time. If binding is possible to a certain degree in specific molecular conformations, the signal of IL-1RAcP can be detected even in high concentrations of the antibody in solution (plateau not at zero or close to zero). In these cases, as both antibodies are able to bind at the same time to a certain degree, the two antibodies are assigned to different epitope bins.

Epitope Binning scheme as determined by ELISA-based experiments using the project candidates and reference antibodies either as IgGs or as FabCys-AviHis ELISA Based Epitope Binning:

Epitope binning was performed using an ELISA-based competition assay. The experiments were performed using either IgG1f_AEASS or FabCys-AviHis. Antibodies were diluted to three (3) nM (for IgGs) or to 20 nM (in case of Fabs) in PBS. 20 µl of the antibody solution was added to 384-well Nunc MaxiSorp™ plates (MTP, black Nunc™ #460518) and incubated o/N at 4° C. The next day 90 µL/well blocking solution (5% BSA in PBS) was added to the plate followed by an incubation at RT for at least 1 h. During incubation, the competing antibodies, including reference and negative control antibodies, were diluted in assay buffer (1×PBS, 0.5% BSA, 0.02% Tween 20™ (polysorbate 20)). Subsequently, a 7-step 1:5 serial dilution for each antibody was prepared in assay buffer and biotinylated human IL-1RAcP (AG-12210) was added to the dilutions in a final concentration of 1.5 nM and incubated for 1 h at gentle agitation.

Following the incubation of the blocking solution, the ELISA plates were washed 3× with PBST. Subsequently, 20 µl/well of the prepared antibody/antigen solution was transferred to the wells and incubated for 30 min with gentle agitation. Subsequently, plates were washed 3× using PBS-T.

For detection 20 µl of a prepared streptavidin-alkaline phosphatase conjugate solution was added to the wells in order to detect bound biotinylated human IL-1RAcP. Incubation happened for 30 min with gentle agitation. Following the incubation with streptavidin-alkaline phosphatase conjugate, assay plates were washed 5× with PBS-T. Then 20 µl of AttoPhos substrate (diluted 1:5 in H2O) was added to the wells. Plates were incubated for 10 min at RT and readout happened using a Tecan M1000 Pro Reader.

The different epitope bins are as follows:

- Bin B: CAN04 with a unique competition profile, potentially sharing parts of the epitope (overlapping epitope) with 1A05 (Bin AB), and Y024084 (Bin F) Bin AB: 1A05 with a unique competition profile, potentially sharing parts of the epitope (overlapping epitope) with CAN04 (Bin B), Y024084 (F), Y024148 and Y024149. Thus 1A05 is potentially sharing parts of the epitope with all tested antibodies.
- Bin A: Y024148 and Y024149, with a unique competition profile, potentially sharing parts of the epitope (overlapping) with 1A05 (Bin AB), Y024148, Y024149,
- Bin C: h11C5 with a unique competition profile. Bin C is clearly discriminated from bin B, A and AB.
- Bin F: Y024084 potentially overlapping with parts of Bin AB. No apparent overlap with Bin A.

FIGS. 7A-7E shows ELISA based epitope binning. Every graph represents an individual first antibody in the FabCys-AviHis format coated on the surface. A fixed concentration of biotinylated IL-1RAcP (1.5 nM; AG12210) was pre-incubated with increasing concentrations of the second antibody as FabCys-AviHis for 1 h. Subsequently, pre-formed antigen antibody complex was added to the respective wells with the surface coated first antibody. Detection happened via the biotin of IL-1RAcP using a streptavidin-alkaline phosphatase conjugate. The dotted line indicates the signal of an IL-1RAcP unspecific isotype control added in a concentration of 1 pM. The black dotted line indicate the signal of IL-1RAcP only without a second antibody. MOR3207 binds to the chLys-Tag of the IL-1RAcP antigen.

Epitope Analysis Using Octet Binning:

Time-resolved epitope binning on Octet (HTX) instrument was performed to classify antibodies (IgG/Fab fragments) into groups of identical, or significantly overlapping epitopes, i.e. antibodies that were able to inhibit each other's binding. The same sample prerequisites as for $K_D$ determination. Antibody samples were tested pairwise in a full factorial assay design, e.g. for two antibody samples A and B the following pairwise binding events were required: A-A, A-B, B-A, B-B.

For epitope binning in "sandwich" assay setup, Octet sensor tips were modified with different antibody samples present in sample set. A medium to high capture level was applied. The sample set consisted of all available samples in Fab format versus IgG format. Either IgG samples were captured (via Fc), loaded with antigen, and then subjected to Fab, or in reverse Fab samples were captured (vis His-tag), loaded with antigen, and subsequently investigated for binding of IgG.

Sensors bearing the different antibodies were loaded with monomeric antigen, and subsequently subjected to one of the antibody samples (in different format than captured samples) to check for binding to the antibody-presented antigen. Additional binding was only expected to occur, if the second antibody recognized a different epitope.

For evaluation, the signals at the end of antigen loading and secondary antibody binding were monitored, and curves inspected in terms of sufficient antigen loading and possible dissociation of antigen. For the controls, i.e. double binding steps of the identical antibodies (A-A, B-B); no additional binding was expected for the second antibody. Double binding events of all different antibody sample pairs were compared for consistency, e.g. if additional binding of B was observed in the sample order A-B (different epitopes), the sample order B-A was expected to result in additional binding of A, too. Possible causes for creating such inconsistencies were e.g. partially overlapping epitopes, or insufficient loading of antigen. Octet based epitope binning was performed in a sandwich setup. One antibody was captured on several sensors, loaded with antigen (human IL-1RAcP; AG-12118), followed by binding of the complete sample set in the other format. The assay was performed twice h11C5 was only available as IgG but not as Fab.

Results:

Both assay runs gave consistent results within the run, and also consistent results between setups. Five samples could be assigned to a group of overlapping epitopes, here named A, AB, B (meaning that A did not compete with B, but both A and B competed with AB). Three samples bound to different nonoverlapping epitopes (C, D, E) without competition with epitope cluster A-AB-B. The epitopes were defined as follows:
Epitope B: Y024148 and Y024149. Epitope AB: Y024084 (AB*) and 1A05. Epitope A: CAN04. Epitope C: h11C5. (Epitope D: CAN03).

The results are in line with the results gathered in ELISA based experiments from above.

Example 8 Signalling in Human Dermal Fibroblasts $EC_{80}$ levels of cytokines used in all assays, and tested for the individual cytokines and batches.

Fibroblasts:

Human: Human dermal fibroblasts, from adult donor (HDFa) (LifeTechnologies cat #C-013-5C) were suspended in Medium 106 (Gibco, cat no: M-106-500) with supplement (LSGS-kit, Gibco, cat. no. 5-003-K) and Gentamicin (Gibco, cat no: R-015-10) and seeded (1500 cells/well) in 384-well plates in a volume of 30 µl. Two hours post plating 10 µl of the test antibodies were added to the cells and incubated for 30 min. 10 µl of recombinant human IL-1α (*E.* coli derived, R&D Systems cat #200-LA) was added to the cells to a final concentration of 2 pM. Or 10 µl of recombinant human IL-1β (human IL-1β, R&D Systems cat #201-LB-010) was added to the cells to a final concentration of 1 pM. Or 10 µL of IL-36α, β, or γ (R&D Systems cat #6995-IL Cat #6834-ILB and Cat #6835-ILB, respectively) was added to the cells to a final concentration of 10, 3 and 1.5 nM, respectively. The plate was incubated for 24 hours at 37° C. in a humidified incubator. Subsequently, 2 µl of the supernatant was used to quantify IL-8 by HTRF (CisBio cat #62HIL08PEH), measuring FRET at 665 nm and normalized to the fluorescence of europium cryptate at 620 nm. The assay was modified from manufacture instructions. Briefly equal amounts of anti-IL8-XL conjugate and anti-IL8 cryptate conjugate were thawed and reconstitution buffer was added to dilute 20-fold. After reconstitution, the two reagents were mixed in a 50 ml centrifuge tube and an equal amount of media was added. 2 µl of supernatant per well was transferred to a detection plate and 4 µl of the freshly prepared mix was added. Plates were sealed, centrifuged for 30 seconds and incubated at room temperature for 2 hours. Readout was done in an Envision plate reader.

Cynomolgus: Cynomolgus Dermal Fibroblasts (cyDF) (Pelo Biotech cat #PB-CY-423-0811) were suspended in cynomolgus fibroblast growth medium (Pelo Biotech cat #PB-MY-400-900) and seeded (3500 cells/well) in collagen coated 384-well plates. 10 µl of the test antibodies were added to the cells and incubated for 30 min. Subsequently, 10 ul of cyno IL-10 was added to the cells. The final concentration of cytokine was 1 pM of recombinant cyno IL-1β (Sino Biological cat #90010-CNAE). The plate was incubated for 24 hours at 37° C. in a humidified incubator. 1 µl supernatant was used to quantify IL-8 by proximity Homogenous Time-resolved Fluorescence (HTRF, CisBio cat #62HIL08PEH) measuring FRET at 665 nm and normalized to the fluorescence of europium cryptate at 620 nm. The assay was modified from the manufacture instructions and run as follows: equal amounts of anti-IL-8-XL conjugate and anti-IL-8-Cryptate conjugate were thawed and reconstitution buffer was added to dilute 20-fold. After reconstitution, the two reagents were mixed in a 50 ml centrifuge tube and added in an equal amount of media. 1 µl of supernatant per well was transferred to a detection plate and 4 µl of freshly prepared mix was added. Plates were sealed, centrifuged for 30 seconds and incubated at room temperature for 2 hours. Readout in Envision plate reader. FIGS. 8A-8E showing exemplary results of cell based functional assays utilizing primary dermal fibroblasts, either human dermal fibroblasts stimulated with 10 nM, 3 nM or 1.5 nM of IL-36α, IL-360, or IL-36γ respectively and with 2 pM IL-1α or Cynomolgus dermal fibroblasts stimulated with 1 pM IL-1β.

Example 9 Signalling Measured in Keratinocytes

The Human Epidermal Keratinocytes from adult donor (HEKa) (ATCC®-RCS-200-011™) cells were suspended in EpiLife growth medium (EpiLife-Cascade Biologics, cat no: MEPI500CA) supplemented with HKGS without hydrocortisone (HKGS-kit, Gibco 5-001-K, 1819066) and seeded (6000 cells/well) in 384-well plates in a volume of 30 µL. Two hours post plating 10 µl of the test antibodies were added to the cells and incubated for 30 min. Subsequently 10 µL of IL-1β (R&D Systems cat #201-LB-010) was added to the cells to the final concentration of 0.06 nM. Or 10 µL of IL-36β (R&D Systems cat #6834-ILB) was added to the cells to the final concentration of 0.25 nM. The plate was incubated for 24 hours at 37° C. in a humidified incubator. 10 µl supernatant was used to quantify IL-8 levels by using a cytokine-specific detection antibody labelled with MSD SulfoTAG™ NHS-Ester ($C_{43}H_{41}N_7O_{16}RuS_4$) reagent (Mesoscale cat #K211ANB-2). The assay was run according to the manufacturer instructions.

Figure 9A:
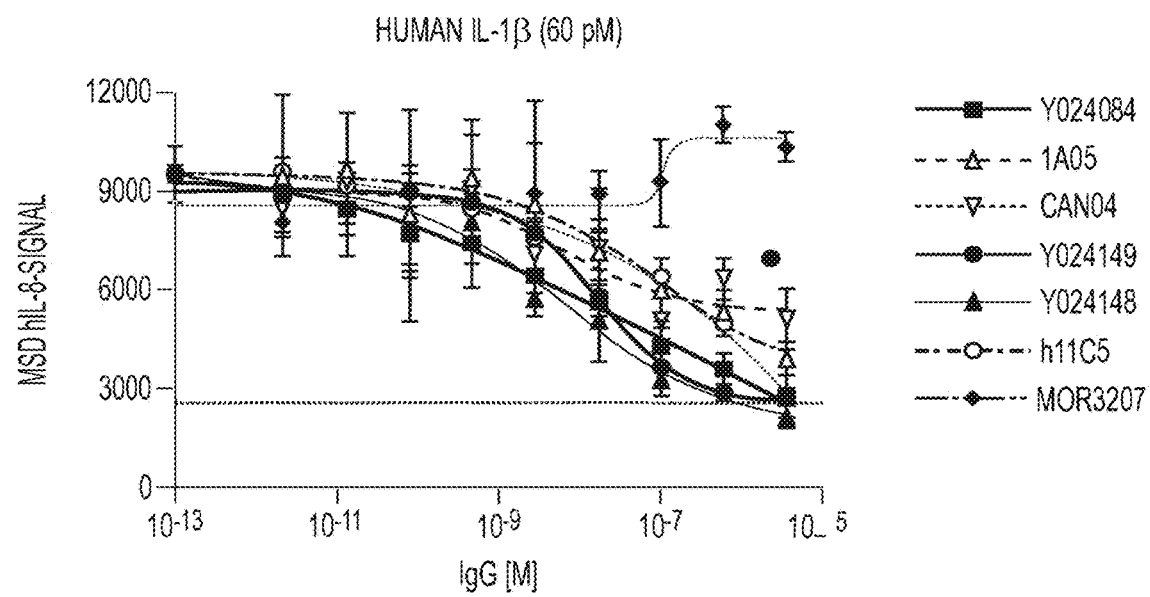
FIG. 9A: Inhibition of signalling by anti-IL1RAcP mAbs in primary human keratinocytes stimulated with 60 pM IL-1β.
Figure 9B:
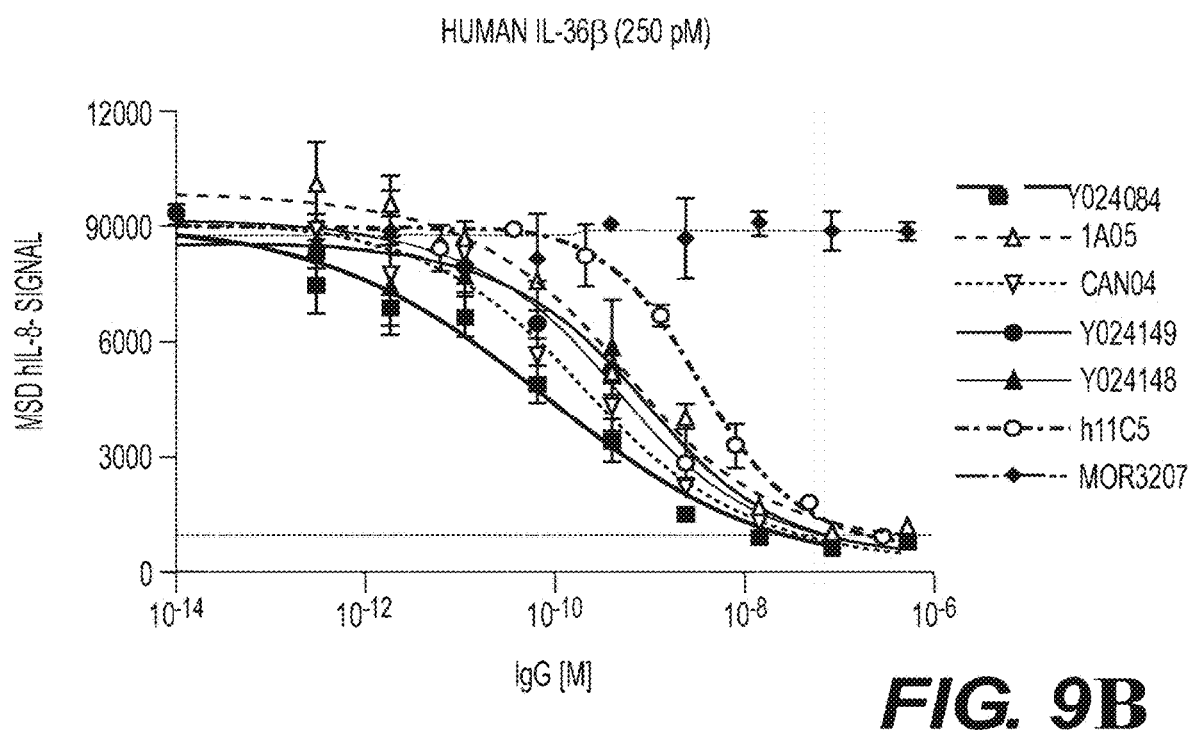
FIG. 9B: Inhibition of signalling by anti-IL1RAcP mAbs in primary human keratinocytes stimulated with 250 pM IL-36μ.

Results in FIGS. 9A and 9B of cell based functional assays utilizing primary human keratinocytes.

Example 10 Signalling in PBMCs

Human IL-1β Induced IFN-γ Release in Human PBMCs:

The human peripheral blood mononuclear cells (PBMCs) were isolated from buffy coats by density centrifugation using Lymphoprep™ (Stemcell cat #07851). On the assay day, cells were thawed and suspended in medium RPMI 1640 with FCS 10%, P/S 1% (both Life Technologies) and recombinant human IL-12 with a concentration of 0.6 nM (R&D Systems Cat #219-IL-025). Cells were seeded in 384-well plates (60000 cells/well) in a volume of 30 µl on the assay day. 10 µl of the test antibodies were added to the cells and incubated for 30 min. 10 µL of IL-1β was added to the cells to a final concentration of 0.05 nM (human IL-1β, R&D Systems cat #201-LB-010). The plate was incubated for 24 hours at 37° C. in a humidified incubator. 10 µl supernatant was used to quantify IFNγ levels by using a cytokine-specific detection antibody labelled with MSD SULFO-TAG™ reagent (Mesoscale cat #K211AEB-2; $C_{43}H_{41}N_7O_{16}RuS_4$). The assay was run according to the manufacturer instructions.

Human IL-33 Induced IFN-γ Release in Human PBMCs:

The cells were suspended in Medium RPMI 1640 (Life Technologies cat #M-106-500) with FCS 10%, P/S 1% (both Life Technologies) and recombinant human IL-12 to a final concentration of 0.6 nM (R&D Systems, Cat #219-IL-025) and seeded in 384-well plates (50000 cells/well) in a volume of 30 µl on the assay day. 10 µl of the test antibodies were added to the cells and incubated for 30 min. 10 uL of IL-33 was added to the cells in a final concentration of 0.05 nM (human IL-33, R&D Systems cat #3625-IL-010).

The plate was incubated for 24 hours at 37° C. in a humidified incubator. 10 µl supernatant was used to quantify IFNγ levels by using a cytokine-specific detection antibody labelled with MSD SULFO-TAG™ reagent (Mesoscale cat #K211AEB-2; $C_{43}H_{41}N_7O_{16}RuS_4$). The assay was run according to the manufacturer instructions.

Figure 10A:
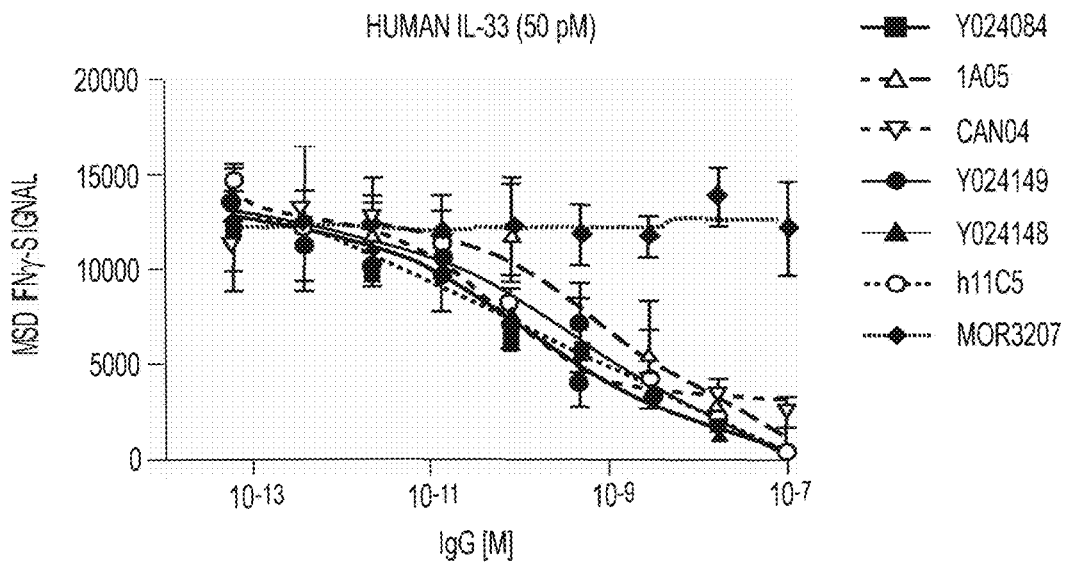
FIG. 10A: Inhibition of signalling by anti-IL1RAcP mAbs in human PBMCs stimulated with 50 pM IL-33.
Figure 10B:
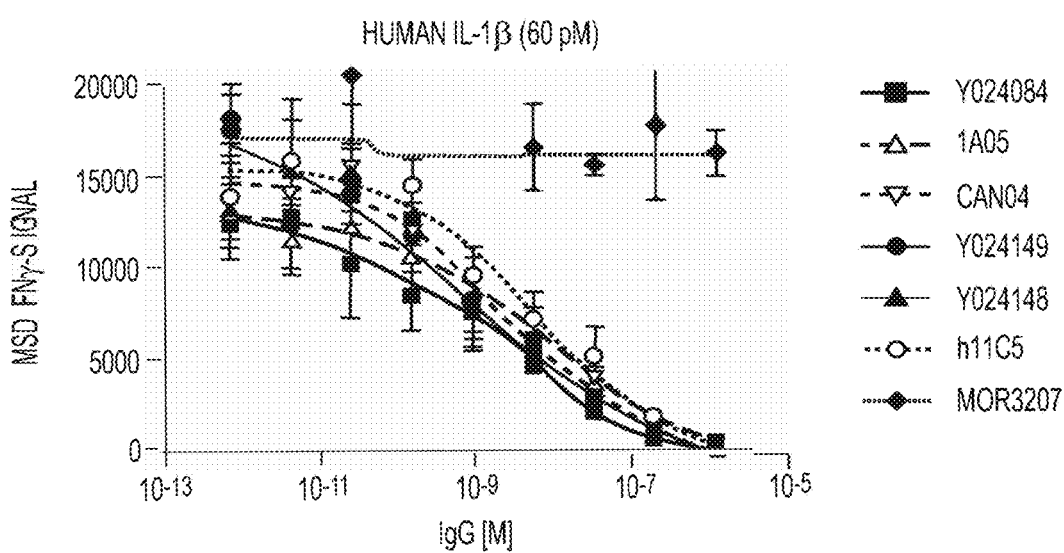
FIG. 10B: Inhibition of signalling by anti-IL1RAcP mAbs in human PBMCs stimulated with 60 pM IL-1β.

FIGS. 10A and 10B shows exemplary results of cell based functional assays utilizing human PBMCs, either stimulated with 50 pM IL-33 or 50 pM IL-1β.

Example 11 sIL-1RAcP

In vivo the extracellular soluble form of IL-1RAcP (sIL-1RAcP) also exists due to alternative splicing. It is abundantly present in circulation at levels around 8-15 nM. The anti-IL-1RAcP antibody will also bind the soluble form of IL-1RAcP. Therefore, the assessment of the functional inhibition of anti-IL-1RAcP antibody in PBMCs in the presence of low and high level of sIL1RAcP protein was performed and demonstrated that there was still full inhibition of the IL-33-mediated IFNγ release, and that the full inhibition happened at roughly the same concentration, even though the $IC_{50}$ values were higher with the presence of sIL1RAcP.

Figure 11A:
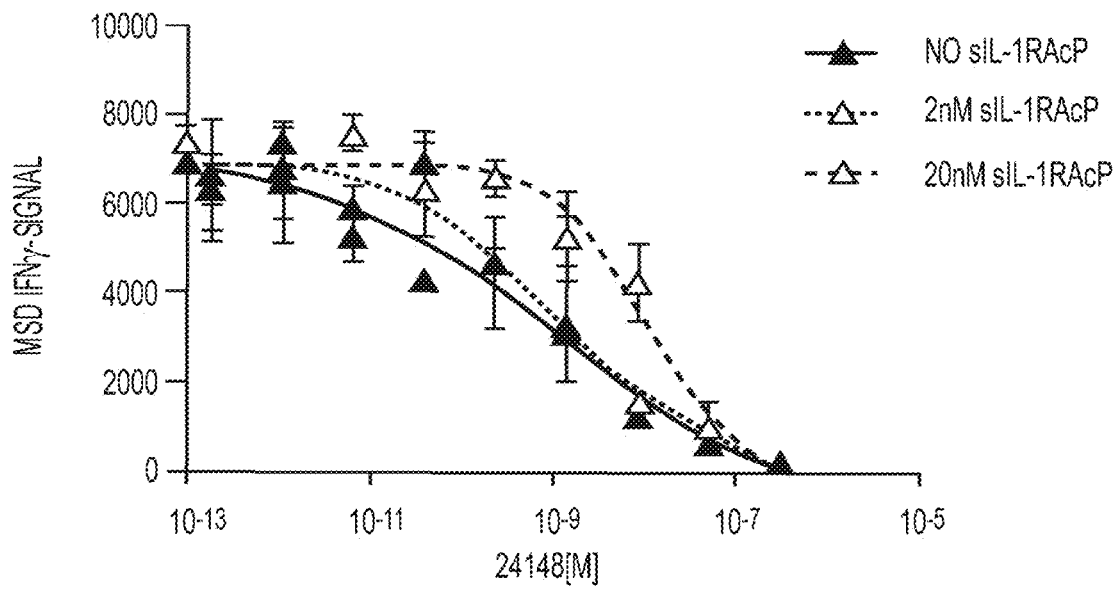
FIG. 11A: Inhibition of signalling by anti-IL1RAcP mAb Y024148, in human PBMC stimulated with 50 pM IL-33, in presence or absence of increasing concentration of exogenously added sIL-1RAcP.
Figure 11B:
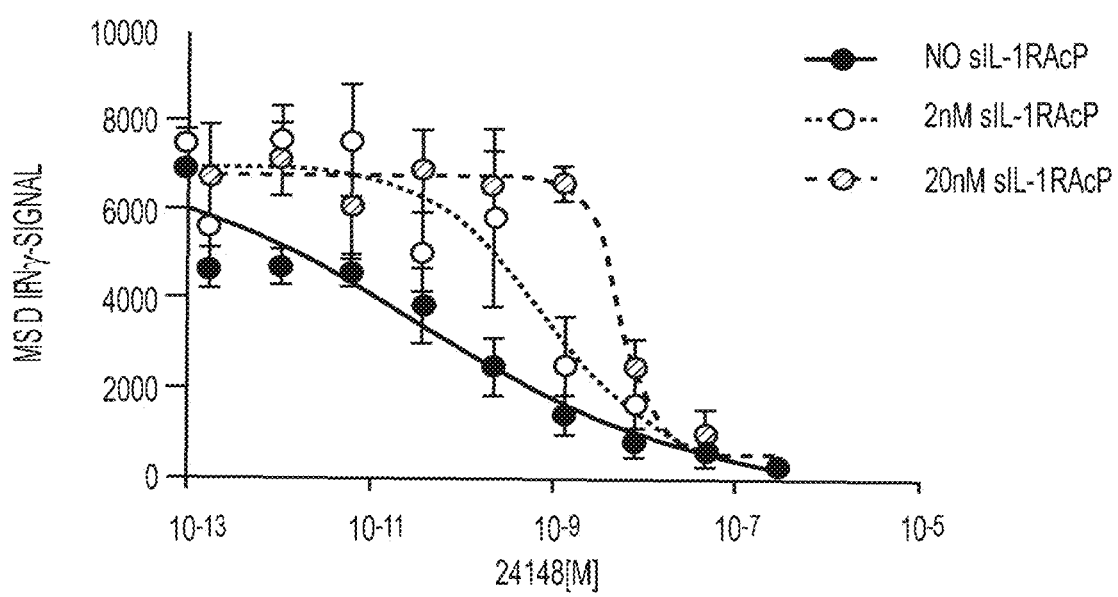
FIG. 11B: Inhibition of signalling by anti-IL1RAcP mAb Y024149, in human PBMC stimulated with 50 pM IL-33, in presence or absence of increasing concentration of exogenously added sIL-1RAcP.
Figure 12A:
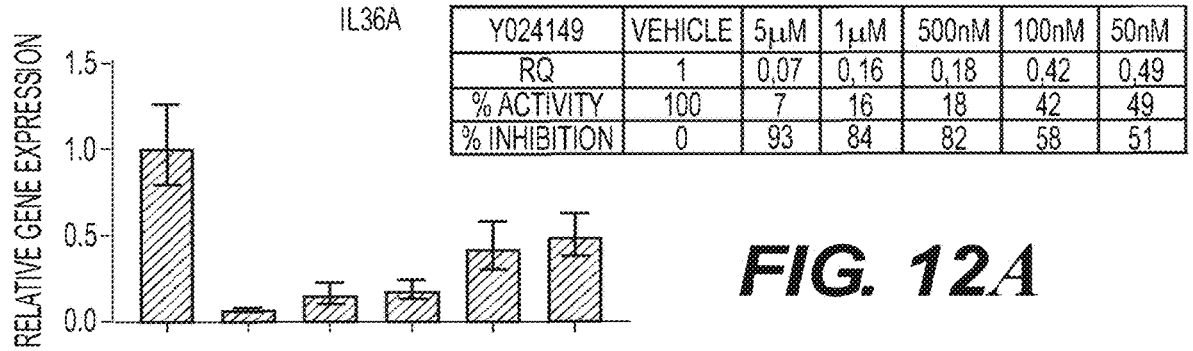
FIG. 12A: Inhibition of signal by anti-IL1RAcP mAb Y024149 in human skin explants stimulated with 50 ng/mL IL-1β. Inhibition of IL36A gene expression is expressed as relative gene expression level and percentage of inhibition.
Figure 12B:
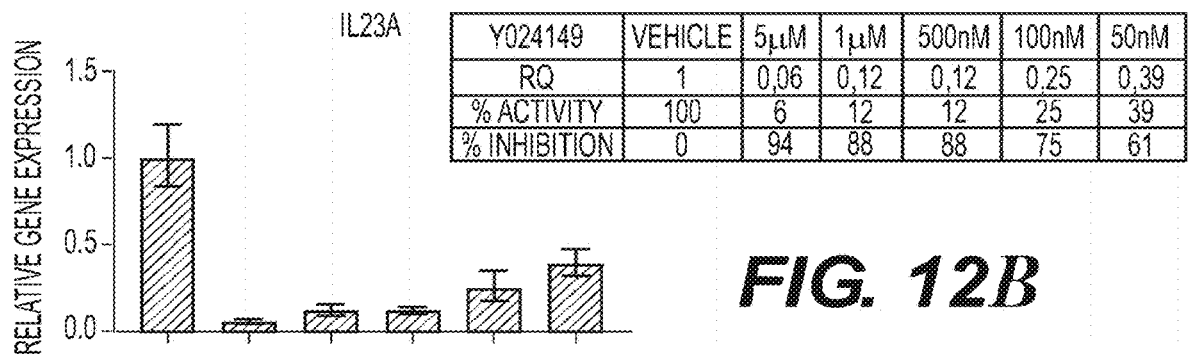
FIG. 12B: Inhibition of signal by anti-IL1RAcP mAb Y024149 in human skin explants stimulated with 50 ng/mL IL-1β. Inhibition of IL23A gene expression is expressed as relative gene expression level and percentage of inhibition.
Figure 12C:
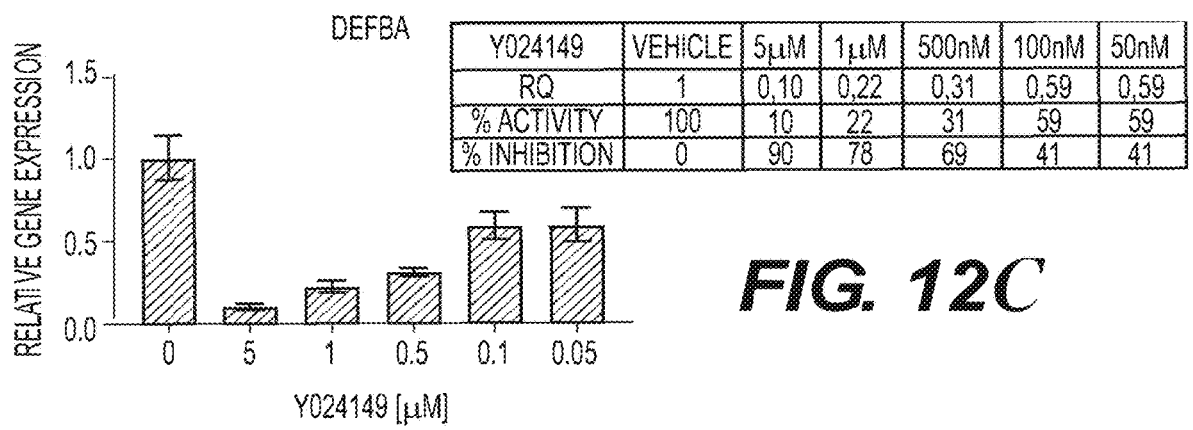
FIG. 12C: Inhibition of signal by anti-IL1RAcP mAb Y024149 in human skin explants stimulated with 50 ng/mL IL-1β. Inhibition of DEFB4 gene expression is expressed as relative gene expression level and percentage of inhibition

Exemplary results in FIGS. 11A and 11B of cell based functional assays utilizing human PBMCs, stimulated with 50 pM IL-33 in the presence of 0, 2 or 20 nM soluble IL-1RAcP (sIL-1RAcP).

The antibodies were compared in various assays side by side with the three reference antibodies CAN04, 1A05 and h11C5. Exemplary curves are displayed in FIGS. 8A-8E (assays using human or cynomolgus primary dermal fibroblasts stimulated with human IL-1α, human IL36g, and cynomolgus IL-1b) and FIGS. 9A and 9B (assays utilizing primary human keratinocytes stimulated with IL-1b and IL-36b). Additionally, the inhibitory effect in human PBMCs stimulated with IL-33 and IL-1b shown in FIGS. 10A and 10B. The overview of all assays with an average IC50 value (nM) is displayed in table. All present disclosure antibodies do inhibit signalling with an Emax of 100%. In most assays all present disclosure antibodies are superior or similar to the reference antibodies. The direct comparison of the IC50 values of the reference 1A05 and the project antibodies is displayed in Table 2.

followed by cDNA synthesis, and amplification of cDNA by quantitative real-time PCR using Taqman® Gene Expression Assays, accordingly to the manufacturer instruction. The level of IL-1β responsive genes, IL23A, IL36A and DEFB4, were quantified in all samples and normalized for the expression of housekeeping genes actb, ppia and rplp0.

Results

The functional blockade of IL-1β-induced IL23A, IL36A and DEFB4 gene expression in human skin samples was demonstrated for Y024149. Using skin punch biopsies from four different donors (n=4), Y024149 showed to inhibit IL23A, IL36A and DEFB4 gene expression in a concentration dependent manner reaching a ~90-95% inhibition at the highest concentration of 5 μM.

TABLE 2

| | HDFa | | | | | | | | CyDFa | | HBKa | | | | PBMC | | | |
|---|---|---|---|---|---|---|---|---|---|---|---|---|---|---|---|---|---|---|
| | IL-1α ± SD | | IL-36α ± SD | | IL-36β ± SD | | IL-36γ ± SD | | IL-1β ± SD | | IL-1β ± SD | | IL-36β ± SD | | IL-1β ± SD | | IL-33 ± SD | |
| | IC50 (nM) | SD (nM) | IC50 (nM) | SD (M) | IC50 (nM) | SD (nM) | IC50 (nM) | SD (nM) | IC50 (nM) | SD (nM) | IC50 (nM) | SD (nM) | IC50 (nM) | SD (nM) | IC50 (M) | SD (nM) | IC50 (nM) | SD (nM) |
| CAN04 | 3.6 | N/A | 0.019 | 0.01 | 0.024 | 0.012 | 0.008* | 0.002 | ~1 | N/A | 18* | 10 | 0.02 | 0.009 | 3.5 | 2.8 | 13 | 1.7 |
| 1A05 | 24 | 6 | 0.05 | 0.029 | 0.15 | 0.099 | 0.067 | 0.039 | 0.48 | 0.29 | 162 | 166 | 0.12 | 0.09 | 5 | 3 | 1.8 | 0.9 |
| h11C5 | 22 | 10 | 0.18 | 0.14 | 0.28 | 0.15 | 0.24 | 0.13 | 1 | 1.3 | 670 | 169 | 1.98 | 2 | 4.6 | 3 | 0.82 | 0.77 |
| Y024084 | 20 | 17 | 0.025 | 0.025 | 0.033 | 0.014 | 0.022 | 0.009 | 0.12 | 0.09 | 19 | 13 | 0.029 | 0.009 | 5.2 | 2.7 | 0.69 | 0.49 |
| Y024148 | 1.2 | 1.2 | 0.014 | 0.007 | 0.039 | 0.022 | 0.042 | 0.03 | 0.043 | 0.034 | 35 | 18 | 0.2 | 0.1 | 1.2 | 0.8 | 0.72 | 0.59 |
| Y024149 | 1.1 | 0.3 | 0.039 | 0.036 | 0.06 | 0.037 | 0.026 | 0.019 | 0.032 | 0.019 | 31 | 9 | 0.094 | 0.088 | 1.7 | 1.6 | 0.2 | 0.09 |

Summary of functional assays including antibodies and reference antibodies side by side. Values are average $IC_{50}$ (nM) values±standard deviation. Assays were performed utilizing: I. human dermal fibroblasts (HDFa) stimulated with IL-1α, IL-36α, IL-36β and IL-36γ. Stimulation with IL-1b was also assessed in HDFa and found fully inhibited, but no $IC_{50}$ values determined (not included). II. Cynomolgus dermal fibroblasts (CyDFa) stimulated with cynomolgus IL-1b. III. Human keratinocytes (HEKa) stimulated with IL-1b and IL-36β. 4. Human PBMCs stimulated with IL-1b and IL-33.

Example 12 Human IL-1β Induced Target Activation in Human Skin Explants

For human skin explant model, full thickness punch biopsies of 3 mm in diameter were generated from skin specimens from healthy subjects and placed in supplemented EpiLife™ medium (Gibco, Cat #M-EPI-500-CA) in 96 well culture plate (100 μL medium per well; one punch biopsy/well). Supplement without the addition of hydrocortisone are ready to use and consists of recombinant human insulin-like growth factor-I, bovine transferrin and human epidermal growth factor, as well as a vial of Gentamicin/Amphotericin solution (Gibco, Cat #S-001-K). Skin samples were treated with increasing concentration of test antibody Y024149 or vehicle control. The plate was cultured overnight at 37° C. in a humidified incubator (18-20 hours culture). Subsequently, the samples were stimulated by the addition of 5 μl/well of supplemented EpiLife™ medium conditioned with rhIL-1β at the final concentration of 50 ng/ml (rhIL-1β from R&D systems, Cat. #201-LB). Unstimulated vehicle control samples were also included. The samples were finally incubated for 6 hours at 37° C. in a humidified incubator. At the termination time point, skin samples were harvested and subjected to RNA extraction Example 13 Cynomolgus IL-1β Induced IL-6 Release in Cynomolgus Whole Blood Cynomolgus whole blood samples (100 μl) were seeded in a 96 well culture plate (100 μl/well) containing 50 μl/well of RPMI 1640 medium (Gibco, Cat #42401018) conditioned with +1% P/S and with increasing concentration of test antibody Y024149 or vehicle control. The plate was incubated for 30 minutes at 37° C. in a humidified incubator. Subsequently, the samples were stimulated by the addition of 50 μl/well of RPMI 1640 medium conditioned with 1% P/S and recombinant cyno IL-1 (Sino Biological Cat #90010-CNAE) at the final concentration of 50 ng/ml. Unstimulated vehicle control samples were also included. The samples were finally incubated for 22 hours at 37° C. in a humidified incubator. At the termination time point, 100 μl of diluted plasma samples were harvested for each sample by the means of centrifugation at 500×g for 10 minutes at room temperature and assayed for the level of IL-6 by using the specific U-plex NHP IL-6 MSD assay (Meso Scale Discovery, Cat #K156TXK-2) accordingly to the manufacturer instructions.

Figure 13A:
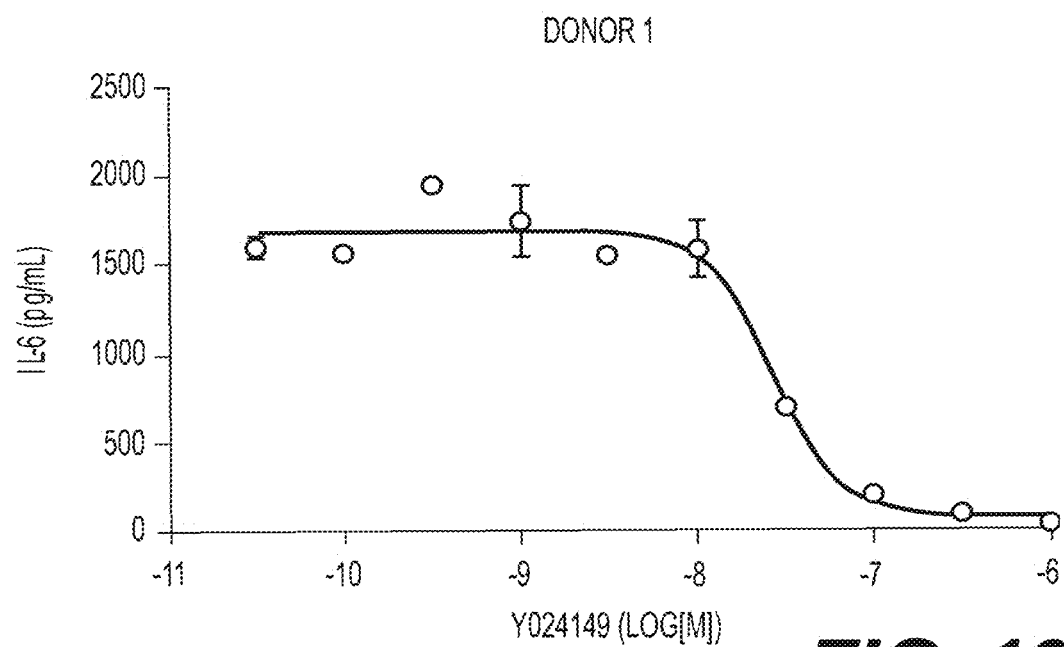
FIG. 13A: Inhibition of signal IL-1β induced IL-6 release by anti-IL1RAcP mAb Y024149 in cynomolgus whole blood stimulated with 50 ng/mL IL-1β. Donor 1.
Figure 13B:
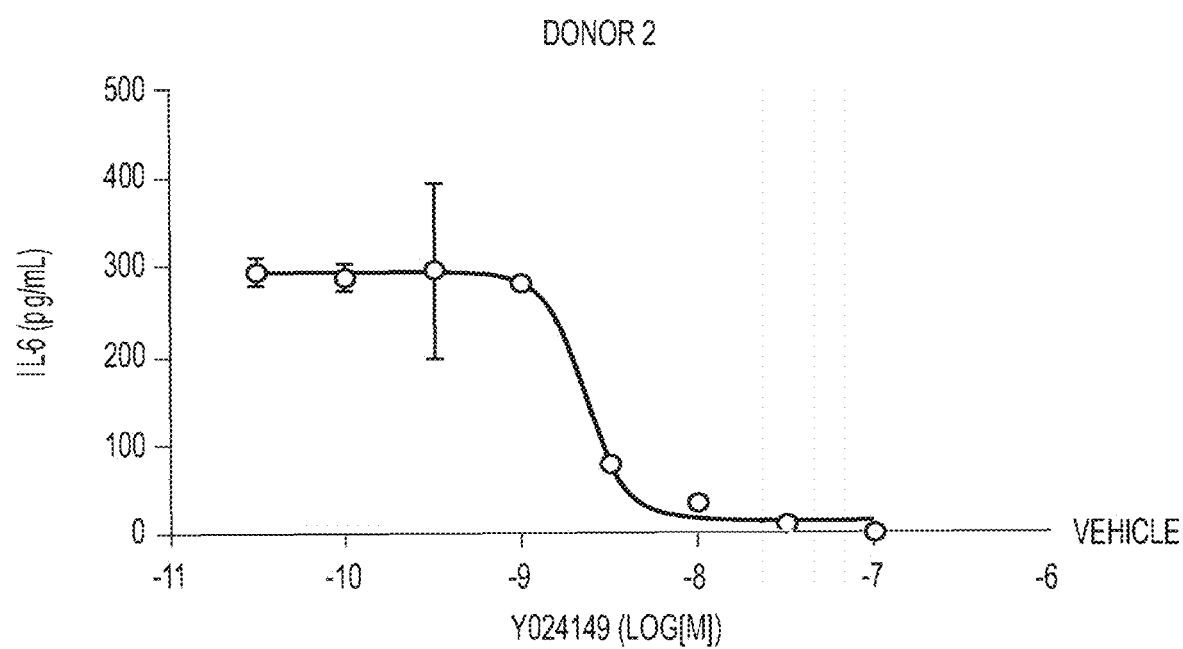
FIG. 13B: Inhibition of signal by anti-IL1RAcP mAb Y024149 in cynomolgus whole blood stimulated with 50 ng/mL IL-1β. Donor 2.

Results:

The functional blockade of IL-1β induced IL-6 release in cynomolgus whole blood was demonstrated for Y024149. Using whole blood from eight different donors (n=8), Y024149 showed to fully inhibit the release of IL-6 induced by stimulation with 50 ng/ml of rcIL-1β with an IC50 of ~50 nM, with maximal inhibition at ~100 nM (FIGS. 13A and 13B).

Example 14 Human IL-1β Induced IL-6 Release in Human Whole Blood

Human whole blood samples (100 μl) were seeded in a 96 well culture plate (100 μl/well) containing 50 μl/well of RPMI 1640 medium (Gibco, Cat #42401018) conditioned with 1% P/S and with increasing concentration of test antibody Y024149 or vehicle control. The plate was incubated for 30 minutes at 37° C. in a humidified incubator. Subsequently, the samples were stimulated by the addition of 50 µl/well of RPMI 1640 medium conditioned with 1% P/S and rhIL-1β at the final concentration of 1 ng/ml, 5 ng/ml and 10 ng/ml (rhIL-1β from R&D systems, Cat. #201-LB). Unstimulated vehicle control samples were also included. The samples were finally incubated for 22 hours at 37° C. in a humidified incubator. At the termination time point, 100 µl of diluted plasma samples were harvested for each sample by the means of centrifugation at 500×g for 10 minutes at room temperature and assayed for the level of IL-6 by using the specific U-plex Human IL-6 MSD assay (Meso Scale Discovery, Cat #K151TXK) accordingly to the manufacturer instructions.

Figure 14A:
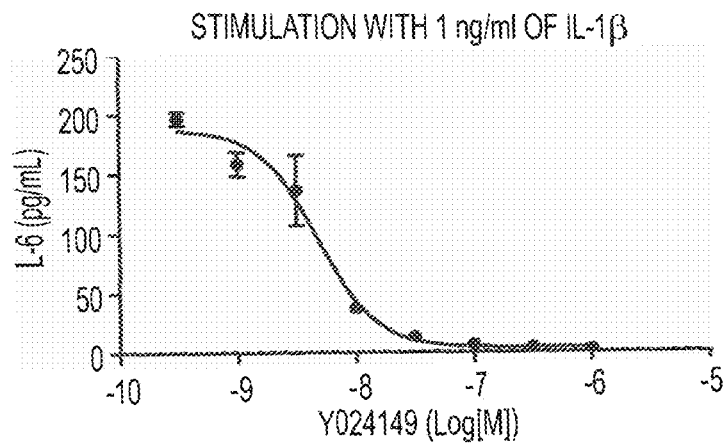
FIG. 14A: Inhibition of signal by anti-IL1RAcP mAb Y024149 in human whole blood stimulated with 1 ng/mL IL-1β.
Figure 14B:
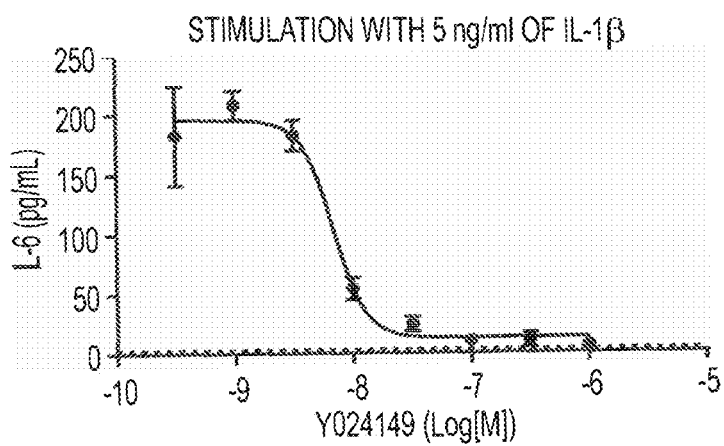
FIG. 14B: Inhibition of signal by anti-IL1RAcP mAb Y024149 in human whole blood stimulated with 5 ng/mL IL-1
Figure 14C:
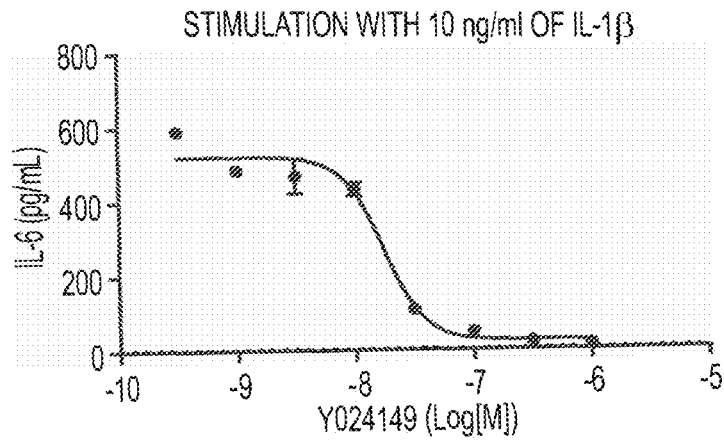
FIG. 14C: Inhibition of signal by anti-IL1RAcP mAb Y024149 in human whole blood stimulated with 10 ng/mL IL-1β

Results:

The functional blockade of IL-1β induced IL-6 release in human whole blood was demonstrated for Y024149. Using whole blood from three different donors (n=3), Y024149 showed to fully inhibit the release of IL-6 induced by stimulation with 1 ng/ml, 5 ng/ml and 10 ng/ml of rhIL-1β with an IC50 of ~10 nM, ~8 nM and ~20 nM, respectively, with maximal inhibition at 50-100 nM (FIGS. 14A, 14B, and 14C).

Example 15: Cynomolgus IL-33 Induced IFN-γ Release in Cynomolgus Whole Blood Cynomolgus whole blood samples (100 µl) were seeded in a 96 well culture plate (100 µl/well) containing 50 µl/well of RPMI 1640 medium (Gibco, Cat #42401018) conditioned with 1% P/S and with increasing concentration of test antibody Y024149 or vehicle control. The plate was incubated for 30 minutes at 37° C. in a humidified incubator. Subsequently, the samples were stimulated by the addition of 50 µl/well of RPMI 1640 medium conditioned with 1% P/S, ascorbic acid, rhIL-12 (R&D Systems, Cat #219-IL-005) and rcIL-33 (Sino Biological Cat #90912-CNAE) at the final concentration of 9 µg/ml, 150 ng/ml and 300 ng/ml, respectively. Unstimulated vehicle control samples were also included. The samples were finally incubated for 22 hours at 37° C. in a humidified incubator. At the termination time point, 100 µl of diluted plasma samples were harvested for each sample by the means of centrifugation at 500×g for 10 minutes at room temperature and assayed for the level of IFN-γ by using the specific customized U-plex HNP IFN-γ MSD assay (Meso Scale Discovery, Cat #K15068L) accordingly to the manufacturer instructions.

Figure 15A:
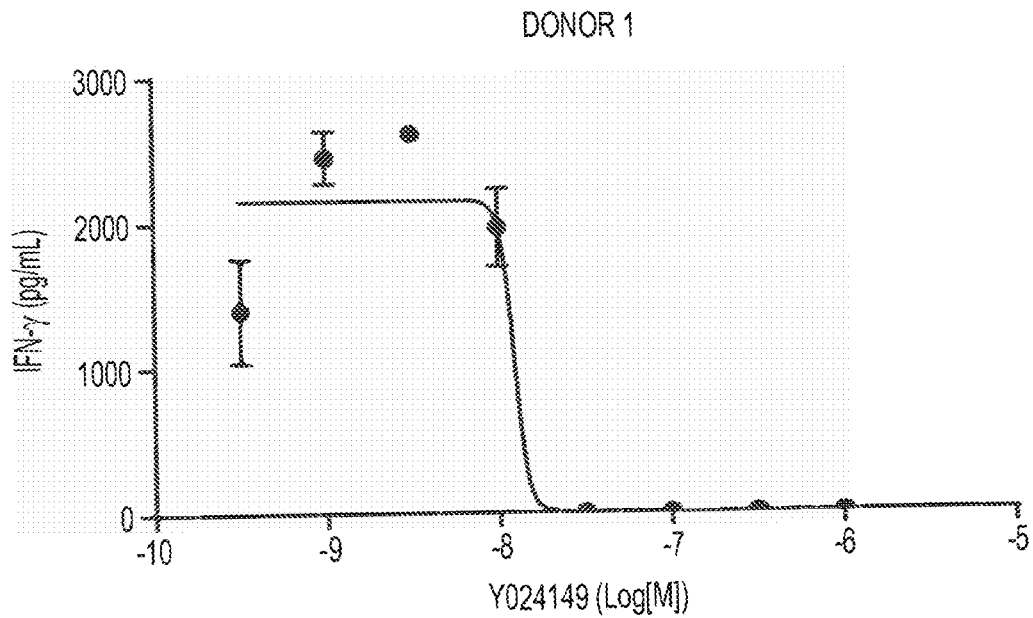
FIG. 15A: Inhibition of signal by anti-IL1RAcP mAb Y024149 in cynomolgus whole blood stimulated with 300 ng/mL IL-33. Donor 1
Figure 15B:
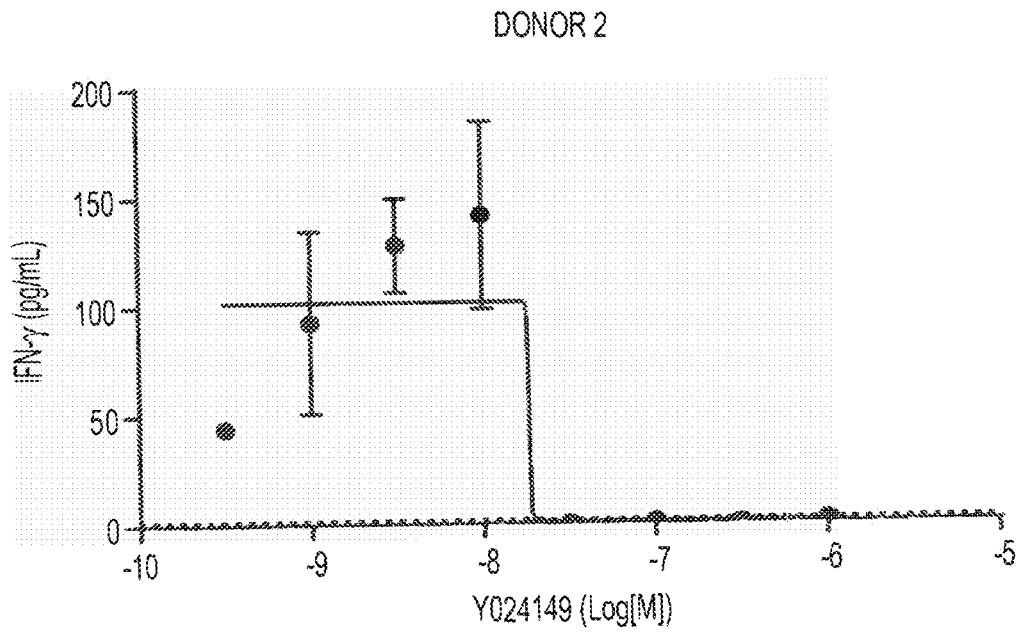
FIG. 15B: Inhibition of signal by anti-IL1RACP mAb Y024149 in cynomolgus whole blood stimulated with 300 ng/mL IL-33. Donor 2

Results:

The functional blockade of IL-33 induced IFN-γ release in cynomolgus whole blood was demonstrated for Y024149. Using whole blood from two different donors (n=2), Y024149 showed to fully inhibit the release of IFN-γ induced by stimulation with 300 ng/ml of rcIL-33 with an IC50 of ~15 nM, with maximal inhibition at 30 nM. (FIGS. 15A and 15B; Functional concentration dependent blockade of cynomolgus IL-33 induced IFN-γ release in cynomolgus whole blood from two donors.)

Example 16 Cynomolgus PK Included on CAN04, 084 and Antibodies of the Disclosure The monkeys were dosed IV with vehicle (n=2), 0.6, 2.0, 6.0, 20 and 60 mg/kg respectively (all n=1) as well as SC with 20 mg/kg (n=2). The formulations were made in PBS pH 7.1 and given as a slow bolus over 5 minutes. Four different ligand binding assays were used for PK analysis of the soluble target and soluble drug candidate.

Target mediated drug disposition (TMDD) dominated the clearance/distribution of drug especially at plasma concentrations of Y024149 below 100 nM in the cynomolgus monkeys, whereas a long half-life was seen for the linear phase when the target was saturated.

Figure 16A:
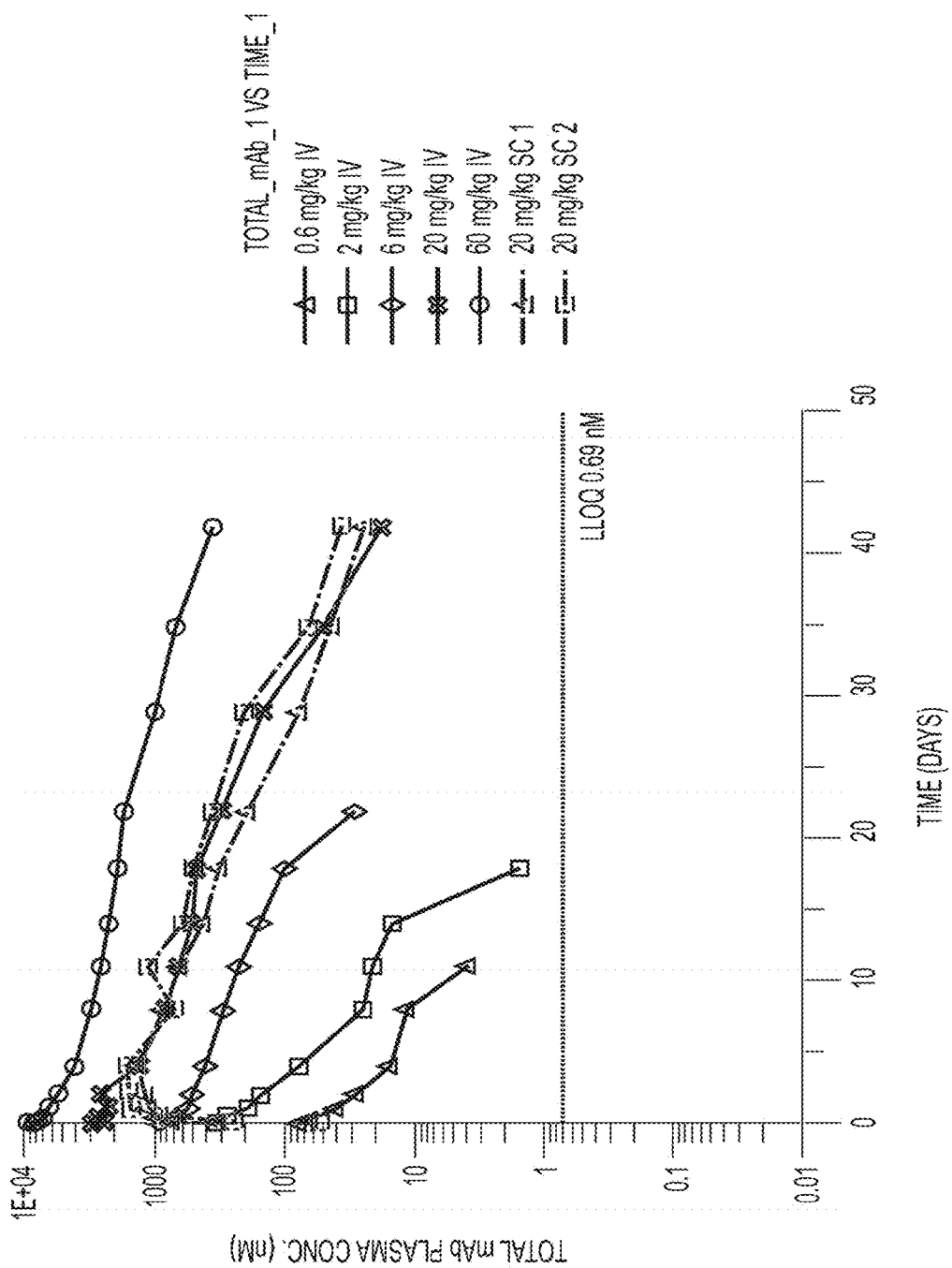
FIG. 16A: Plasma concentrations of Y024149 versus time profiles for each of the 9 monkeys during the first dose. Plasma concentration (nM) shown are total soluble mAb Y024149
Figure 16B:
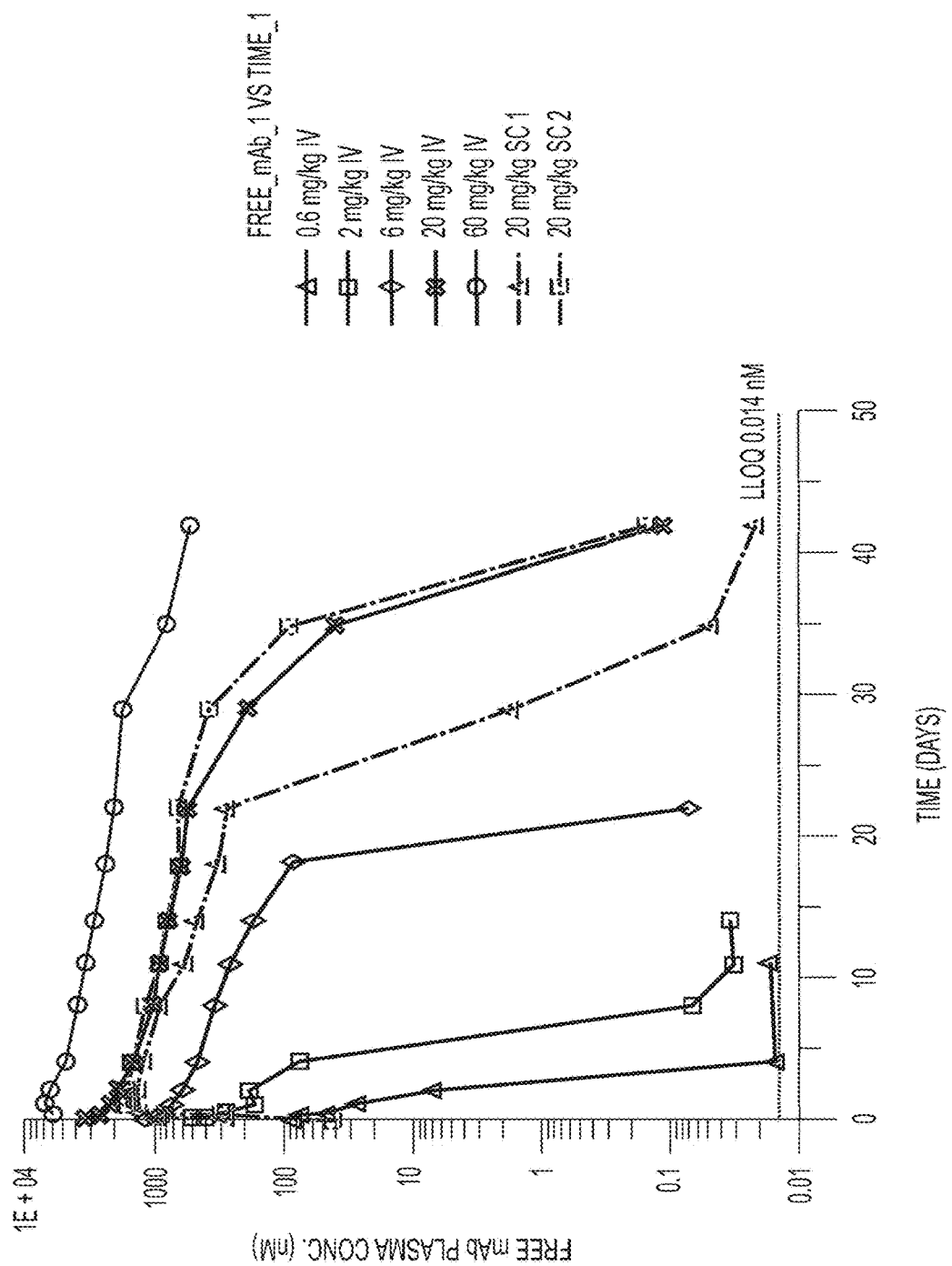
FIG. 16B: Plasma concentrations of Y024149 versus time profiles for each of the 9 monkeys during the first dose. Data shown are free/unbound soluble Y024149
Figure 16C:
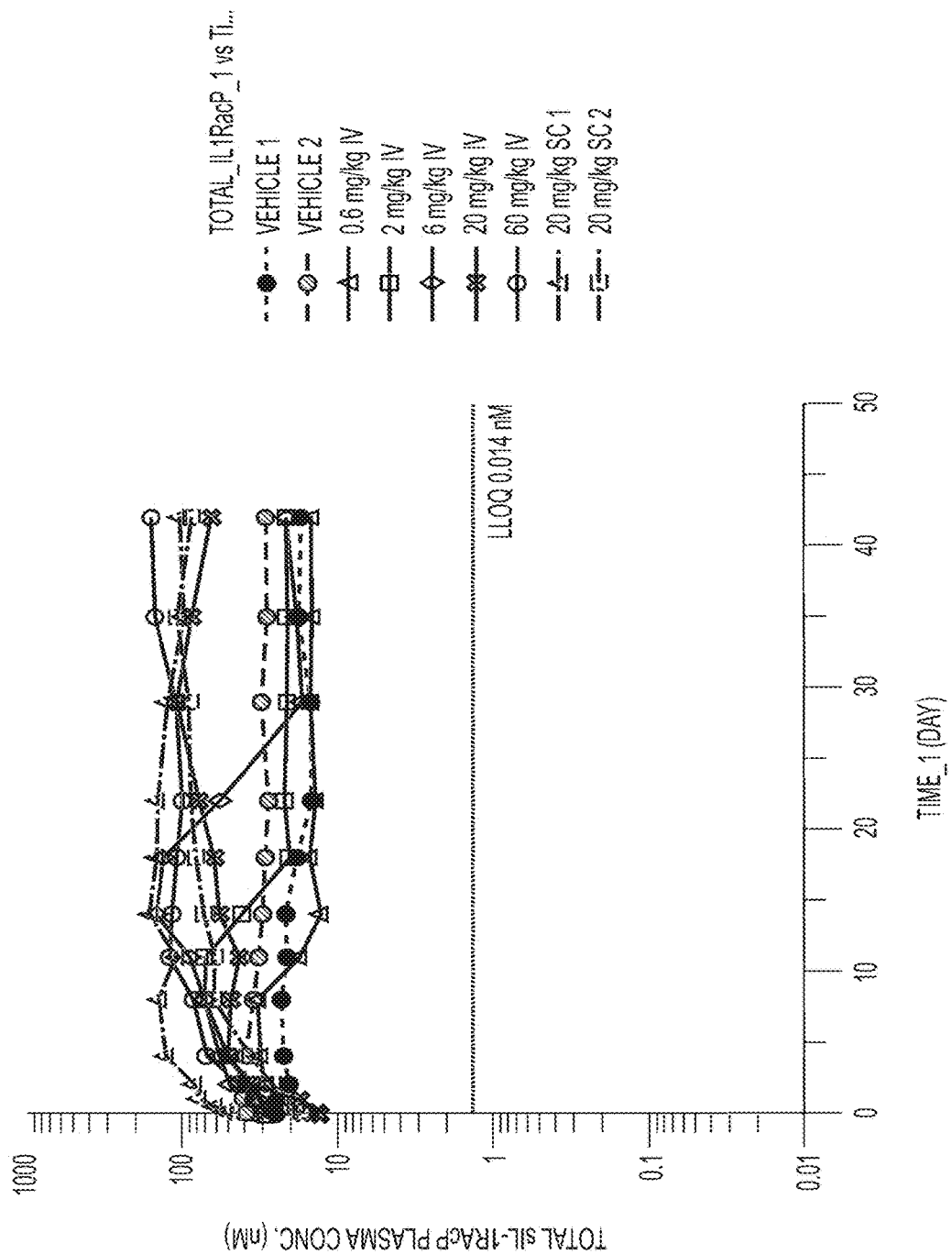
FIG. 16C: Plasma concentrations of Y024149 versus time profiles for each of the 9 monkeys during the first dose. Data shown are total soluble IL-1RAcP
Figure 16D:
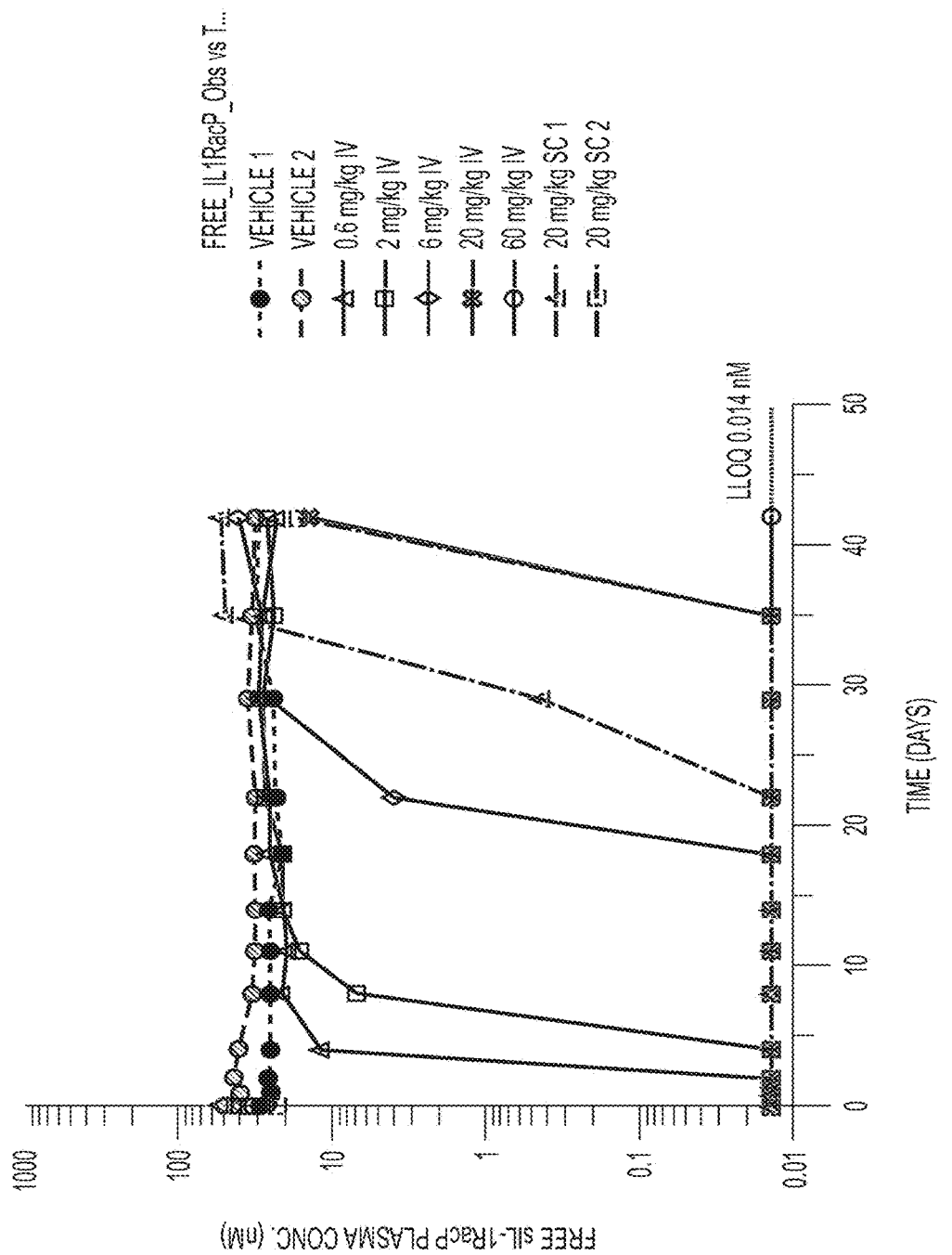
FIG. 16D: Plasma concentrations of Y024149 versus time profiles for each of the 9 monkeys during the first dose. Data shown are free/unbound soluble IL-1RAcP.

Plasma concentrations of Y024149 versus time profiles for each of the 9 monkeys during the first dose. Plasma concentration (nM) shown are total soluble mAb Y024149 (FIG. 16A), free/unbound soluble Y024149 (FIG. 16B), total soluble IL-1RAcP (FIG. 16C) and free/unbound soluble IL-1RAcP (FIG. 16D).

Comparison In Vivo

The monkeys were dosed IV with vehicle (n=2), 6.0 mg/kg of different antibodies, Y024149, or Morphosys 24084 or CAN04 on a Morphosys IgG backbone (all n=1). The formulations were made in PBS pH 7.1 and given as a slow bolus over 5 minutes. Four different ligand binding assays were used for PK analysis of the soluble target and soluble drug candidate. This clearly demonstrates a better exposure and occupancy of the soluble target by Y024149 compared to both CAN04 (R001031) and Mor Y024084. Additionally when compared to the data published for the antibody h11C5 the exposure and occupancy of Y024149 is similar to the data for the half life extended version of the h11C5 antibody (YTE).

Figure 16E:
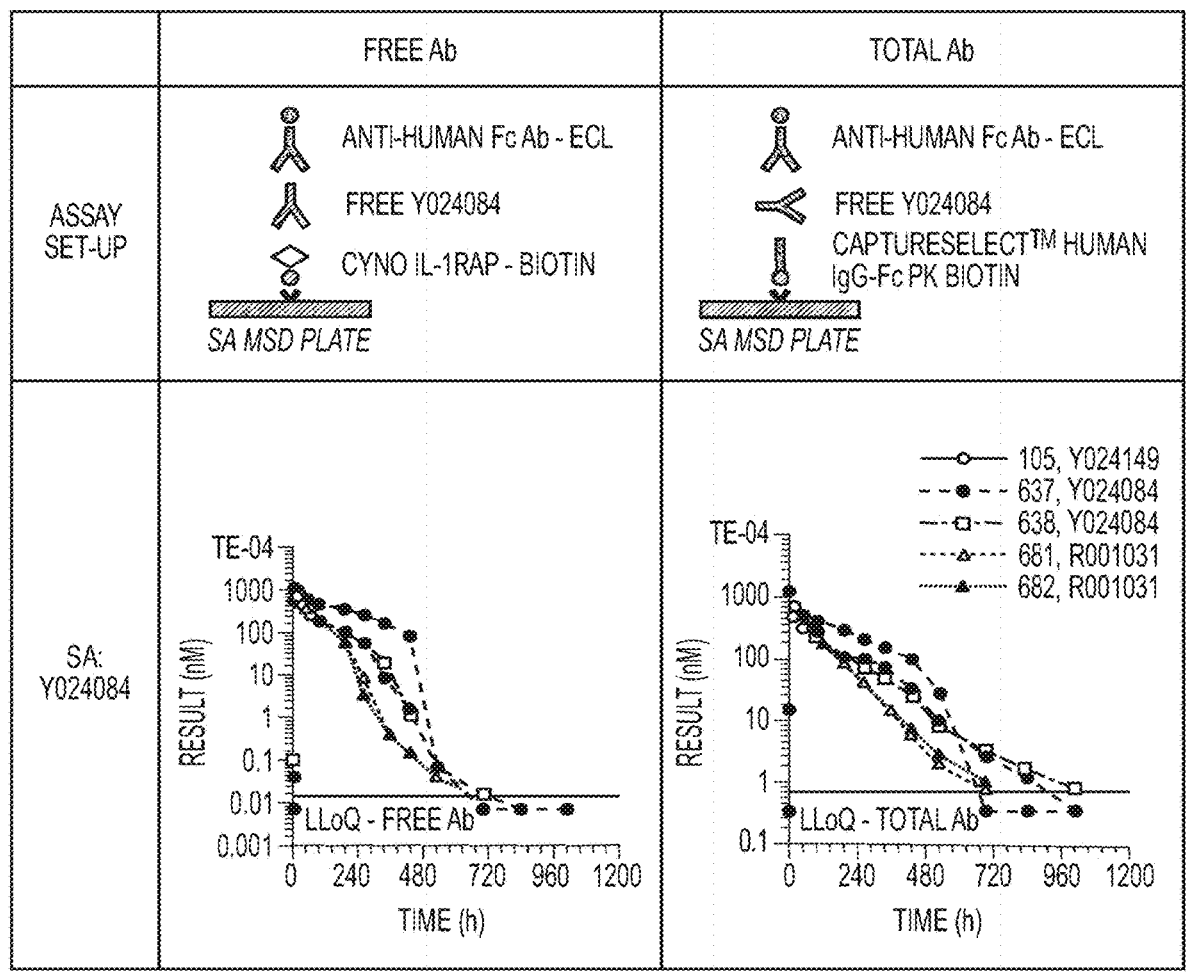
FIG. 16E: Data from in vivo i.v. dosing of 6 mg/kg of antibodies to cynomolgus monkeys. Top: Cartoons describing the assay set ups for the different assays used in the cynomolgus PK/PD study. Bottom: Curves showing the data on the amount of free antibody, total antibody and the free soluble IL-1RAcP and total sIL-1RAcP for Y024149 and reference R001031 (CAN04 in IgG1f_AEASS format) mAbs.
Figure 16F:
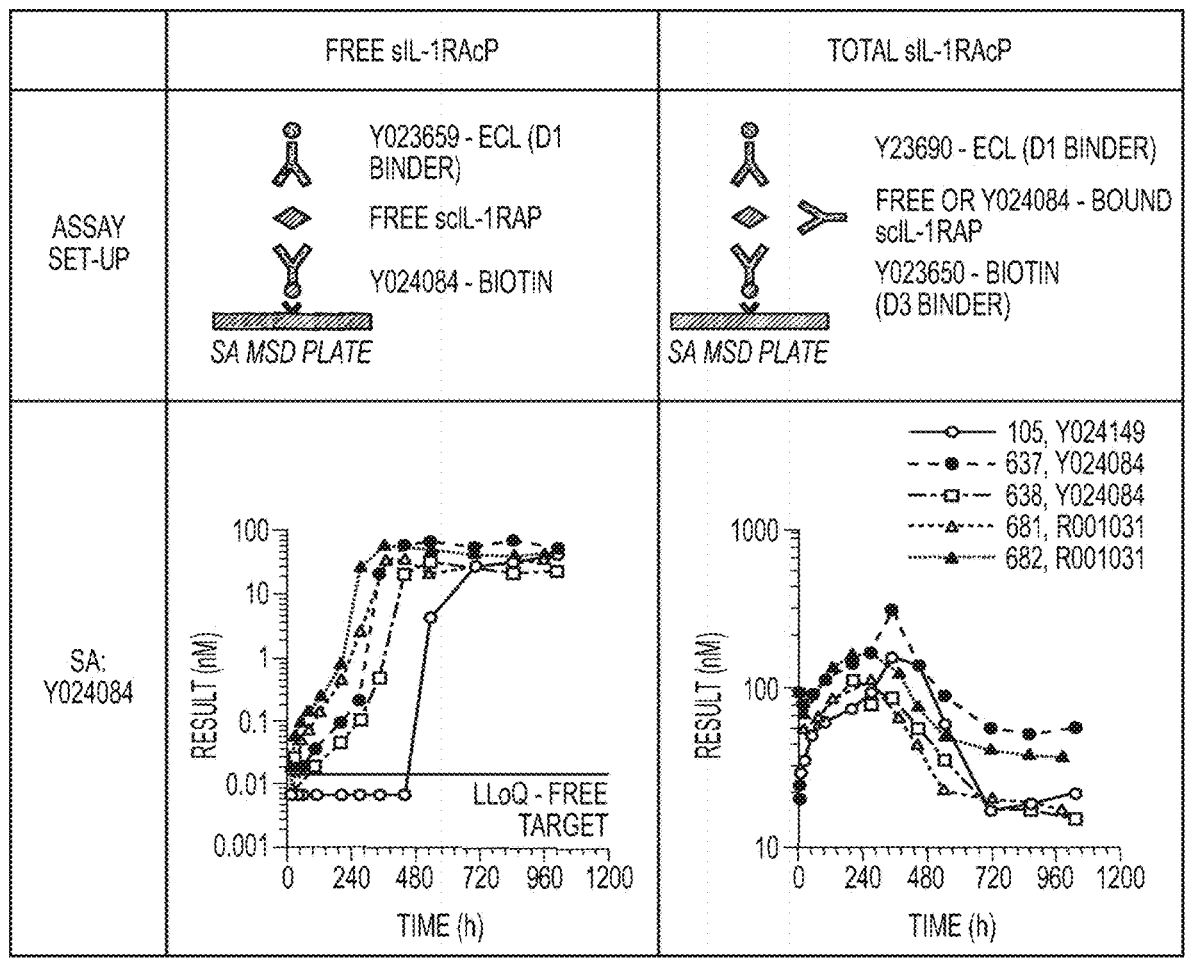
FIG. 16F: Data from in vivo i.v. dosing of 6 mg/kg of antibodies to cynomolgus monkeys. Top: Cartoons describing the assay set ups for the different assays used in the cynomolgus PK/PD study. Bottom: Curves showing the data on the amount of free antibody, total antibody and the free soluble IL-1RAcP and total sIL-1RAcP for Y024084 and reference R001031 (CAN04 in IgG1f_AEASS format) mAbs.

Results in FIGS. 16E and 16F.

INCORPORATION BY REFERENCE

Various publications are cited in the current description and throughout the examples. The content of each publication is incorporated by reference herein in its entirety.

The present disclosure is not to be limited in scope by the specific embodiments or examples described herein. Indeed, various modifications of the disclosure in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

REFERENCES

Palomo et al., Cytokine 76, 2015, 25-37.
Dinarello et al., NRDrug Discov 11(8), 2012, 633-652.
Buhl et. al., Frontiers in Immunology, May 2019, 10, 2019, 1-11.
Xu et. al., Frontiers in Immunology, September 2019, 10, 2019, 1-8.
Tsang et. al., Current Allergy and Asthma Report, 2020, 20-40.
Boraschi et. al., Immunological Reviews, 232, 2018, 197-232.
Khazim et. Al., Immunological Reviews, 281. 2018, 40-56.
Striz et. al., Clinical Science, 131, 2017, 2241-2256.
Jensen et al., Curr. Opin. Investig. Drugs. 11(11), 2010, 1211-1220.
Tavakolpour et al., Cytokine, 129, 2020, 1-8.
Wolk et al., Br. J. Deramtol. 183 (6), 2020, 999-1010.
Morea et al., Methods 20:267-279 (2000).
Machura et al., BioMed Research International 2013: 605262 (2013).

Kabat et al., Sequences of Proteins of Immunological Interest, 5th Ed. Public Health Service, National Institutes of Health, Bethesda, MD., 1983.

Kabat et al., Sequences of Proteins of Immunological Interest, 5th Ed. Public Health Service, National Institutes of Health, Bethesda, MD. (1991).

Chothia et al., J. Mol. Biol. 227: 799-817 (1992); Tramontano et al., J. Mol. Biol, 215:175-182 (1990).

MacCallum et al., J. Mol. Biol. 262:732-745 (1996).

Tatusova et al., "Blast 2 sequences—a new tool for comparing protein and nucleotide sequences", FEMS Microbiol Lett. 174:247-250.

Graham et al., J. Gen. Virol. 36:59 (1977).

Urlaub et al., Proc. Natl. Acad. Sci. USA 77:4216 (1980).

Mather, Biol. Reprod. 23:243-251 (1980).

Wang et al., Journal of Pharmaceutical Sciences, Vol. 96, pp 1-26, 2007.

van den Brulle, J.; Fischer, M.; Langmann, T.; Horn, G.; Waldmann, T.; Arnold, S. et al. (2008): A novel solid phase technology for high-throughput gene synthesis. In Biotechniques 45 (3), pp. 340-343.

Tiller, T.; Schuster, I.; Deppe, D.; Siegers, K.; Strohner, R.; Herrmann, T. et al. (2013): A fully synthetic human Fab antibody library based on fixed VH/VL framework pairings with favorable biophysical properties. In mAbs 5 (3), pp. 445-470.

Friguet, B.; Chaffotte, A. F.; Djavadi-Ohaniance, L.; Goldberg, M. E. (1985): Measurements of the true affinity constant in solution of antigen-antibody complexes by enzyme-linked immunosorbent assay. In *J immunol methods* 77 (2), pp. 305-319.

Haenel, C.; Satzger, M.; Ducata, D. D.; Ostendorp, R.; Brocks, B. (2005): Characterization of high-affinity antibodies by electrochemiluminescence-based equilibrium titration. In *anal biochem* 339 (1), pp. 182-184.

Abraham, R.; Buxbaum, S.; Link, j.; Smith, R.; Venti, C.; Darsley, M.: Determination of Binding Constants of Siaboidies directed against Prostate-specific Antigen using Electrochemiluminescence-based immunoassays (9) (5-6), pp. 456-461.

Piehler, J.; Brecht, A.; Giersch, T.; hock, b.; Gauglitz, G. (1997): Assessment of affinity conatants by rapid solid phase detection of equilibrium binding in a flow system. In *Journal of Immunological Methods* 201, pp. 189-206.

Della Ducata, Daniela; Jaehrling, Jan; Hänel, Cornelia; Satzger, Marion; Wolber, Meike; Ostendorp, Ralf et al. (2015): Solution Equilibrium Titration for High-Throughput Affinity Estimation of Unpurified Antibodies and Antibody Fragments. In *Journal of Biomolecular Screening. DOI:* 10.1177/1087057115595002.

The invention claimed is:

1. An antibody or antigen-binding fragment thereof that binds specifically to IL-1 RAcP, wherein the antibody or antigen-binding fragment comprises an HCDR1 comprising the amino acid sequence of SEQ ID NO: 12, an HCDR2 comprising the amino acid sequence of SEQ ID NO: 13, an HCDR3 comprising the amino acid sequence of SEQ ID NO: 14, an LCDR1 comprising the amino acid sequence of SEQ ID NO: 9, an LCDR2 comprising the amino acid sequence of SEQ ID NO: 10, and an LCDR3 comprising the amino acid sequence of SEQ ID NO: 11.

2. The antibody or antigen-binding fragment of claim 1, wherein the antibody or antigen-binding fragment comprises:
   at least one heavy chain variable domain (VH) comprising the amino acid sequence of SEQ ID NO: 15 or an amino acid sequence that is at least 90% identical to SEQ ID NO: 15; and
   at least one light chain variable domain (VL) comprising the amino acid sequence of SEQ ID NO: 16, or an amino acid sequence that is at least 90% identical to SEQ ID NO: 16.

3. The antibody or antigen-binding fragment of claim 1, wherein the antibody or antigen-binding fragment comprises at least one VH comprising the amino acid sequence of SEQ ID NO: 15 and at least one VL comprising the amino acid sequence of SEQ ID NO: 16.

4. The antibody or antigen-binding fragment of claim 1, wherein the antibody or antigen-binding fragment comprises:
   a heavy chain comprising the amino acid sequence of SEQ ID NO: 19 or an amino acid that is at least 90% identical to SEQ ID NO: 19; and
   a light chain comprising the amino acid sequence of SEQ ID NO: 20 or an amino acid that is at least 90% identical to SEQ ID NO: 20.

5. The antibody or antigen-binding fragment of claim 1, wherein the antibody or antigen-binding fragment comprises a heavy chain comprising the amino acid sequence of SEQ ID NO: 19 and a light chain comprising the amino acid sequence of SEQ ID NO: 20.

6. The antibody or antigen-binding fragment of claim 1, wherein the antibody or antigen-binding fragment is an isolated antibody or antigen-binding fragment.

7. A pharmaceutical composition comprising the antibody or antigen-binding fragment of claim 1 and a pharmaceutically acceptable carrier or excipient.

8. The antibody or antigen-binding fragment of claim 1, wherein the antibody or antigen-binding fragment is a chimeric antibody or antigen-binding fragment.

9. The antibody or antigen-binding fragment of claim 1, wherein the antibody or antigen-binding fragment is a humanized antibody or antigen-binding fragment.

* * * * *